United States Patent
Yang et al.

(10) Patent No.: US 11,453,650 B2
(45) Date of Patent: Sep. 27, 2022

(54) HETEROCYCLIC COMPOUND AND ORGANIC LIGHT EMITTING DEVICE COMPRISING THE SAME

(71) Applicant: LG CHEM, LTD., Seoul (KR)

(72) Inventors: Junghoon Yang, Daejeon (KR); Dong Hoon Lee, Daejeon (KR); Jung Oh Huh, Daejeon (KR); Boon Jae Jang, Daejeon (KR); Dong Uk Heo, Daejeon (KR); Mi Yeon Han, Daejeon (KR); Min Woo Jung, Daejeon (KR)

(73) Assignee: LG CHEM, LTD., Seoul (KR)

( * ) Notice: Subject to any disclaimer, the term of this patent is extended or adjusted under 35 U.S.C. 154(b) by 449 days.

(21) Appl. No.: 16/609,199

(22) PCT Filed: May 31, 2018

(86) PCT No.: PCT/KR2018/006240
§ 371 (c)(1),
(2) Date: Oct. 28, 2019

(87) PCT Pub. No.: WO2018/221985
PCT Pub. Date: Dec. 6, 2018

(65) Prior Publication Data
US 2020/0181096 A1     Jun. 11, 2020

(30) Foreign Application Priority Data

May 31, 2017 (KR) .................. 10-2017-0067648
May 30, 2018 (KR) .................. 10-2018-0062154

(51) Int. Cl.
*C07D 213/16* (2006.01)
*C07D 251/24* (2006.01)
(Continued)

(52) U.S. Cl.
CPC ......... *C07D 251/24* (2013.01); *C07D 213/16* (2013.01); *C07D 239/26* (2013.01);
(Continued)

(58) Field of Classification Search
CPC .. C07D 251/14; C07D 213/16; C07D 239/26; C07D 239/74; C07D 487/04; H01L 51/0067; H01L 51/0072
See application file for complete search history.

(56) References Cited

U.S. PATENT DOCUMENTS

2004/0251816 A1   12/2004   Leo et al.
2006/0013566 A1   1/2006   Nakamura
(Continued)

FOREIGN PATENT DOCUMENTS

JP         2010-111621       5/2010
KR   10-2000-0051826       8/2000
(Continued)

*Primary Examiner* — Vu A Nguyen
(74) *Attorney, Agent, or Firm* — Dentons US LLP

(57) ABSTRACT

Provided is a heterocyclic compound of Chemical Formula 1:

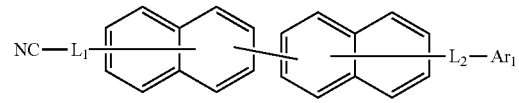

where $L_1$ is a single bond or a substituted or unsubstituted $C_{6-60}$ arylene; $L_2$ is a single bond, a substituted or unsubstituted $C_{6-60}$ arylene, or a substituted or unsubstituted $C_{5-60}$ heteroarylene, and $Ar_1$ is one of the following Chemical Formulas 2, 3, 4, or 5:

[Chemical Formula 2]

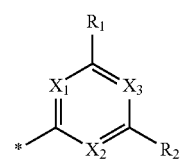

[Chemical Formula 3]

[Chemical Formula 4]

(Continued)

-continued

[Chemical Formula 5]

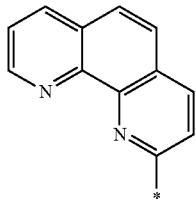

and an organic light emitting device including the same.

12 Claims, 1 Drawing Sheet

(51) Int. Cl.
- *C07D 239/26* (2006.01)
- *C07D 239/74* (2006.01)
- *C07D 487/04* (2006.01)
- *H01L 51/00* (2006.01)
- *H01L 51/50* (2006.01)
- *C07D 401/14* (2006.01)

(52) U.S. Cl.
CPC ......... *C07D 239/74* (2013.01); *C07D 401/14* (2013.01); *C07D 487/04* (2013.01); *H01L 51/0067* (2013.01); *H01L 51/0072* (2013.01)

(56) References Cited

U.S. PATENT DOCUMENTS

| | | |
|---|---|---|
| 2007/0108892 A1 | 5/2007 | Bae et al. |
| 2010/0108989 A1 | 5/2010 | Busing et al. |
| 2010/0109555 A1 | 5/2010 | Ichimura et al. |
| 2015/0001479 A1 | 1/2015 | Lee et al. |
| 2015/0060787 A1* | 3/2015 | Park .................. H01L 51/0067 546/276.7 |
| 2015/0090965 A1 | 4/2015 | Park et al. |
| 2017/0077414 A1 | 3/2017 | Kim et al. |

FOREIGN PATENT DOCUMENTS

| | | |
|---|---|---|
| KR | 10-2007-0091293 | 9/2007 |
| KR | 10-2008-0103953 | 11/2008 |
| KR | 10-2012-0051598 | 5/2012 |
| KR | 10-2012-0061056 | 6/2012 |
| KR | 10-2015-0003564 | 1/2015 |
| KR | 10-2015-0025259 | 3/2015 |
| KR | 10-2015-0039486 | 4/2015 |
| KR | 10-2017-0033482 | 3/2017 |
| KR | 10-2017-0058618 | 5/2017 |
| WO | 2003/012890 | 2/2003 |
| WO | 2004/077885 | 9/2004 |
| WO | 2017/099430 | 6/2017 |

* cited by examiner

[FIG. 1]
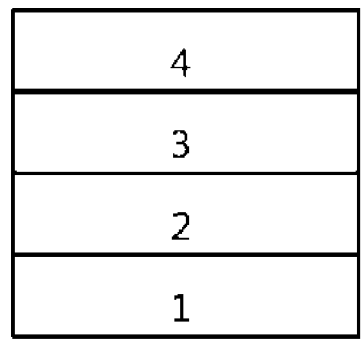
[FIG. 2]
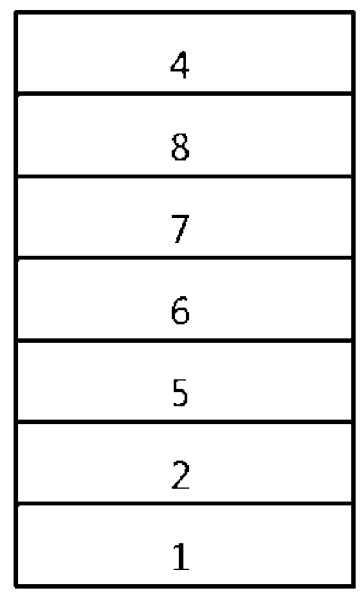

HETEROCYCLIC COMPOUND AND ORGANIC LIGHT EMITTING DEVICE COMPRISING THE SAME

CROSS-REFERENCE TO RELATED APPLICATION(S)

This application is a National Stage Application of International Application No. PCT/KR2018/006240 filed on May 31, 2018, which claims the benefits of the filing dates of Korean Patent Application No. 10-2017-0067648 filed with Korean Intellectual Property Office on May 31, 2017, and Korean Patent Application No. 10-2018-0062154 filed with Korean Intellectual Property Office on May 30, 2018, the entire contents of which are incorporated herein by reference.

TECHNICAL FIELD

The present invention relates to a novel heterocyclic compound and to an organic light emitting device including the same.

BACKGROUND

In general, an organic light emitting phenomenon refers to a phenomenon where electrical energy is converted into light energy by using an organic material. The organic light emitting device using the organic light emitting phenomenon has characteristics such as a wide viewing angle, excellent contrast, a fast response time, and excellent luminance, driving voltage, and response speed, and thus many studies have proceeded thereon.

The organic light emitting device generally has a structure which includes an anode, a cathode, and an organic material layer interposed between the anode and the cathode.

The organic material layer frequently has a multilayered structure that includes different materials in order to enhance efficiency and stability of the organic light emitting device, and for example, the organic material layer can be formed of a hole injection layer, a hole transport layer, a light emitting layer, an electron transport layer, an electron injection layer, and the like. In the structure of the organic light emitting device, if a voltage is applied between two electrodes, the holes are injected from an anode into the organic material layer and the electrons are injected from the cathode into the organic material layer, and when the injected holes and electrons meet each other, an exciton is formed, and light is emitted when the exciton falls to a ground state again.

There is a continuing need for the development of new materials for the organic materials used in these organic light emitting devices.

BACKGROUND ART LITERATURE

Patent Literature (Patent Literature 0001) Korean Patent Laid-open Publication No. 10-2000-0051826.

DETAILED DESCRIPTION

Technical Problem

It is an object of the present invention to provide a novel heterocyclic compound and an organic light emitting device including the same.

Technical Solution

In one aspect of the invention, a binaphthalene compound of the following Chemical Formula 1 is provided.

[Chemical Formula 1]

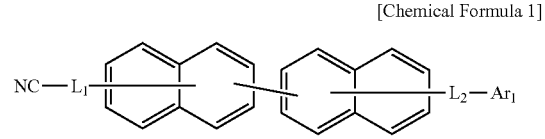

wherein, in Chemical Formula 1:

$L_1$ is a single bond, or a substituted or unsubstituted $C_{6-60}$ arylene;

$L_2$ is a single bond, a substituted or unsubstituted $C_{6-60}$ arylene, or a substituted or unsubstituted $C_{5-60}$ heteroarylene; and $Ar_1$ is one of the following Chemical Formulas 2, 3, 4, or 5:

[Chemical Formula 2]

[Chemical Formula 3]

[Chemical Formula 4]

[Chemical Formula 5]

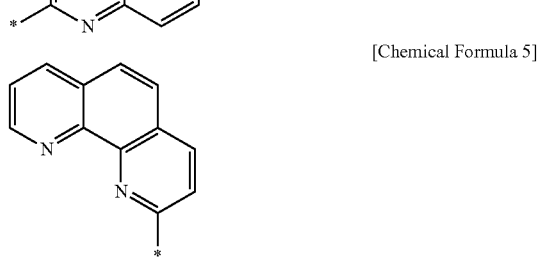

wherein, in Chemical Formulas 2 to 5, $X_1$, $X_2$, and $X_3$ are each independently N or $CR_4$, where there is at least one N;

$X_4$, and $X_5$ are each independently N or $CR_5$, where there is at least one N;

$R_1$, $R_2$, and $R_3$ are each independently a substituted or unsubstituted $C_{1-40}$ alkyl, a substituted or unsubstituted $C_{6-60}$ aryl, or a substituted or unsubstituted $C_{5-60}$ heteroaryl, or $R_1$, $R_2$, and $R_3$ are each independently those in which a hydrogen atom of the alkyl, the aryl, or the heteroaryl is substituted with deuterium or CN; and $R_4$ and $R_5$ are each independently hydrogen, deuterium, a substituted or unsubstituted $C_{1-40}$ alkyl, a substituted or unsubstituted $C_{6-60}$ aryl, or a substituted or unsubstituted $C_{5-60}$ heteroaryl.

In another aspect of the invention, an organic light emitting device is provided, including: a first electrode; a second electrode provided opposite to the first electrode; and one or more organic material layers provided between the first electrode and the second electrode, wherein one or more layers of the organic material layers includes the compound of Chemical Formula 1.

Advantageous Effects

The compound of Chemical Formula 1 described above can be used as a material of an organic material layer of an organic light emitting device, and may improve efficiency, achieve a low driving voltage, and/or improve lifetime characteristics in the organic light emitting device. In particular, the compound of Chemical Formula 1 described above can be used as a material for hole injection, hole transport, hole injection and transport, light emitting, electron transport, or electron injection.

BRIEF DESCRIPTION OF DRAWINGS

FIG. 1 shows an example of an organic light emitting device including a substrate 1, an anode 2, a light emitting layer 3, and a cathode 4.

FIG. 2 shows an example of an organic light emitting device including a substrate 1, an anode 2, a hole injection layer 5, a hole transport layer 6, a light emitting layer 7, an electron transport layer 8, and a cathode 4.

DETAILED DESCRIPTION OF THE EMBODIMENTS

Hereinafter, the present invention will be described in more detail to help understanding of the present invention.

As used herein, the term "substituted or unsubstituted" means being unsubstituted or substituted with one or more substituents selected from the group consisting of deuterium; a halogen group; a nitrile group; a nitro group; a hydroxy group; a carbonyl group; an ester group; an imide group; an amino group; a phosphine oxide growl; an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylphosphine group; and a heterocyclic group containing at least one of N, O, and S atoms, or being unsubstituted or substituted with a substituent to which two or more substituents are linked among the substituents exemplified above. For example, "the substituent to which two or more substituents are linked" can be a biphenyl group. That is, the biphenyl group can also be an aryl group, and can be interpreted as a substituent to which two phenyl groups are linked.

In the present specification, the number of carbon atoms of a carbonyl group is not particularly limited, but is preferably 1 to 40. Specifically, the carbonyl group can be a compound having the following structural formulae, but is not limited thereto:

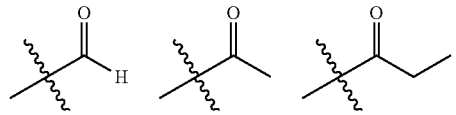

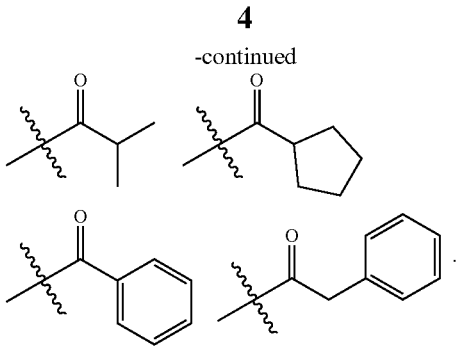

In the present specification, for an ester group, the oxygen of the ester group can be substituted with a straight-chain, branched-chain, or cyclic alkyl group having 1 to 25 carbon atoms, or an aryl group having 6 to 25 carbon atoms.

Specifically, the ester group can be a compound having the following structural formulae, but is not limited thereto:

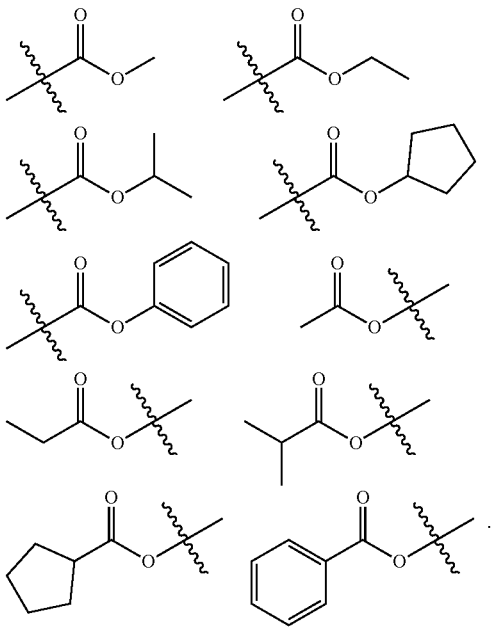

In the present specification, the number of carbon atoms of an imide group is not particularly limited, but is preferably 1 to 25. Specifically, the imide group can be a compound having the following structural formulae, but is not limited thereto:

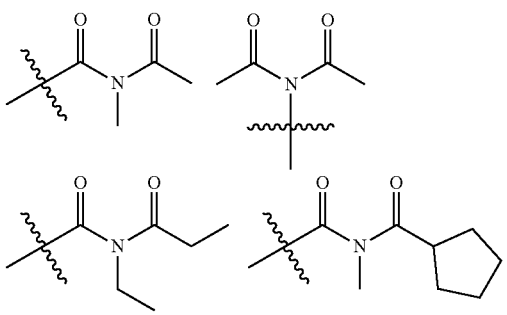

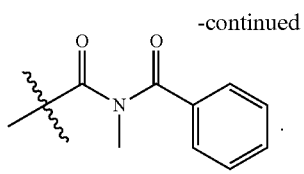

In the present specification, a silyl group specifically includes a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like, but is not limited thereto.

In the present specification, a boron group specifically includes a trimethylboron group, a triethylboron group, a t-butyldimethylboron group, a triphenylboron group, and a phenylboron group, but is not limited thereto.

In the present specification, examples of a halogen group include fluorine, chlorine, bromine, and iodine.

In the present specification, the alkyl group can be a straight chain or branched chain, and the number of carbon atoms thereof is not particularly limited, but is preferably 1 to 40. According to one embodiment, the number of carbon atoms of the alkyl group is 1 to 20. According to another embodiment, the number of carbon atoms of the alkyl group is 1 to 10. According to another embodiment, the number of carbon atoms of the alkyl group is 1 to 6. Specific examples of the alkyl group include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cycloheptylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, iso-hexyl, 2-methylpentyl, 4-methylhexyl, 5-methylhexyl, and the like, but are not limited thereto.

In the present specification, the alkenyl group can be a straight chain or branched chain, and the number of carbon atoms thereof is not particularly limited, but is preferably 2 to 40. According to one embodiment, the number of carbon atoms of the alkenyl group is 2 to 20. According to another embodiment, the number of carbon atoms of the alkenyl group is 2 to 10. According to still another embodiment, the number of carbon atoms of the alkenyl group is 2 to 6. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present specification, a cycloalkyl group is not particularly limited, but the number of carbon atoms thereof is preferably 3 to 60. According to one embodiment, the number of carbon atoms of the cycloalkyl group is 3 to 30. According to another embodiment, the number of carbon atoms of the cycloalkyl group is 3 to 20. According to still another embodiment, the number of carbon atoms of the cycloalkyl group is 3 to 6. Specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethyl-cyclohexyl, 4-tert-butylcyclohexyl, cycloheptyl, cyclooctyl, and the like, but are not limited thereto.

In the present specification, an aryl group is not particularly limited, but preferably has 6 to 60 carbon atoms, and can be a monocyclic aryl group or a polycyclic aryl group. According to one embodiment, the number of carbon atoms of the aryl group is 6 to 30. According to one embodiment, the number of carbon atoms of the aryl group is 6 to 20. The aryl group can be a phenyl group, a biphenyl group, a terphenyl group, or the like as the monocyclic aryl group, but is not limited thereto. Examples of the polycyclic aryl group include a naphthyl group, an anthracenyl group, a phenanthryl group, a pyrenyl group, a perylenyl group, a chrysenyl group, a fluorenyl group, or the like, but are not limited thereto.

In the present specification, a fluorenyl group can be substituted, and two substituent groups can be bonded to each other to form a spiro structure. In the case where the fluorenyl group is substituted,

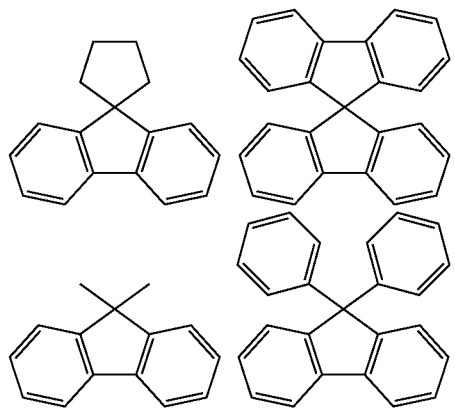

and the like can be formed. However, the structure is not limited thereto.

In the present specification, a heterocyclic group is a heterocyclic group including one or more of O, N, Si, and S as a heteroatom, and the number of carbon atoms thereof is not particularly limited, but is preferably 2 to 60. Examples of the heterocyclic group include a thiophene group, a furan group, a pyrrole group, an imidazole group, a thiazole group, an oxazole group, an oxadiazole group, a triazole group, a pyridyl group, a bipyridyl group, a pyrimidyl group, a triazine group, an acridyl group, a pyridazine group, a pyrazinyl group, a quinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzimidazole group, a benzothiazole group, a benzocarbazole group, a benzothiophene group, a dibenzothiophene group, a benzofuranyl group, a phenanthroline group, an isoxazolyl group, a thiadiazolyl group, a phenothiazinyl group, a dibenzofuranyl group, and the like, but are not limited thereto.

In the present specification, the aryl group in the aralkyl group, the aralkenyl group, the alkylaryl group, and the arylamine group is the same as the aforementioned examples of the aryl group. In the present specification, the alkyl group in the aralkyl group, the alkylaryl group, and the alkylamine group is the same as the aforementioned examples of the alkyl group. In the present specification, the heteroaryl in the heteroarylamine can be applied to the aforementioned description of the heterocyclic group. In the present specification, the alkenyl group in the aralkenyl group is the same as the aforementioned examples of the alkenyl group. In the present specification, the aforementioned description of the aryl group can be applied except that the arylene is a divalent group. In the present specification, the aforementioned description of the heterocyclic group can be applied except that the heteroarylene is a divalent group. In the present specification, the aforementioned description of the aryl group or cycloalkyl group can be applied except that the hydrocarbon ring is not a monovalent group but is formed by combining two substituent groups. In the present specification, the aforementioned description of the heterocyclic group can be applied, except that the heterocycle is not a monovalent group but is formed by combining two substituent groups.

In Chemical Formula 1, depending on the structure in which a binaphthalene group bonded with a specific cyano group is bonded with Ar$_1$, Chemical Formula 1 can be represented by the following Chemical Formulas 1-1, 1-2, 1-3, 1-4, 1-5, 1-6, or 1-7:

[Chemical Formula 1-1]

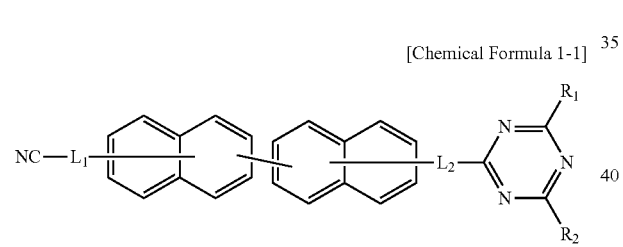

[Chemical Formula 1-2]

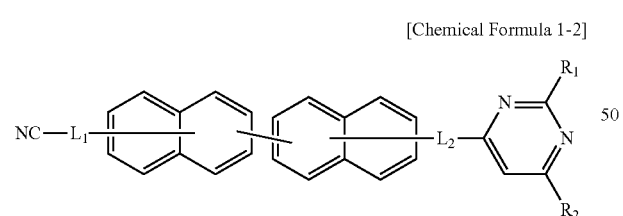

[Chemical Formula 1-3]

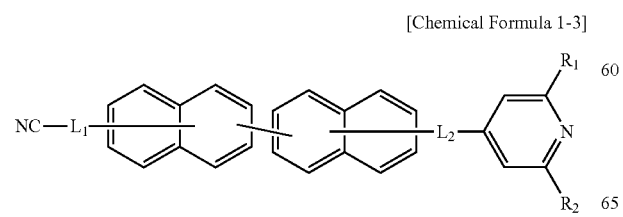

[Chemical Formula 1-4]

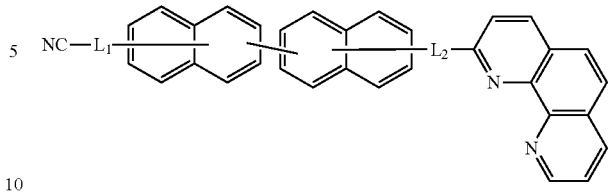

[Chemical Formula 1-5]

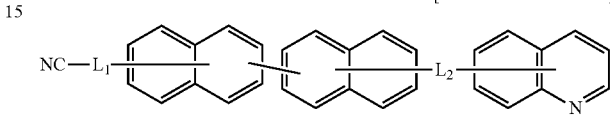

[Chemical Formula 1-6]

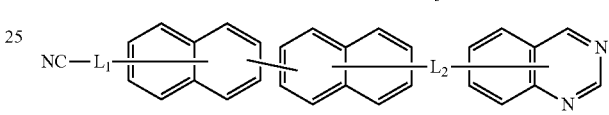

[Chemical Formula 1-7]

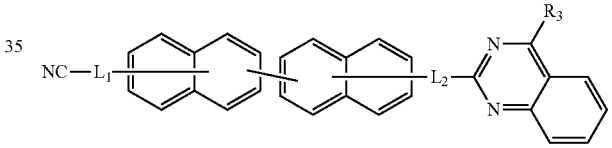

wherein, in Chemical Formulas 1-1, 1-2, 1-3, 1-4, 1-5, 1-6, and 1-7, $L_1$, $L_2$, $R_1$, $R_2$, and $R_3$ are as defined in Chemical Formula 1.

Preferably, $L_1$ and $L_2$ are each independently phenylene or biphenylene.

Preferably, $X_1$, $X_2$, $X_3$, $X_4$, and $X_5$ are each independently N.

Preferably, $R_1$, $R_2$, $R_3$, $R_4$, and $R_5$ are hydrogen, a phenyl group, or a pyridinyl group.

Thus, when two functional groups bonded with a binaphthalene group have different structures, electron transport capability, band gap, energy level, and thermal properties can be more easily controlled. In addition, the electrical and thermal properties can be easily predicted depending on the substitution position of naphthalene. In particular, the transport properties of holes and electrons can be actively controlled. Furthermore, such asymmetrical structural features make it possible to synthesize various derivatives when compared with a symmetrical structure, thereby allowing active improvement of the efficiency and lifetime characteristics of the device.

Representative examples of the compound represented by Chemical Formula 1 are as follows.

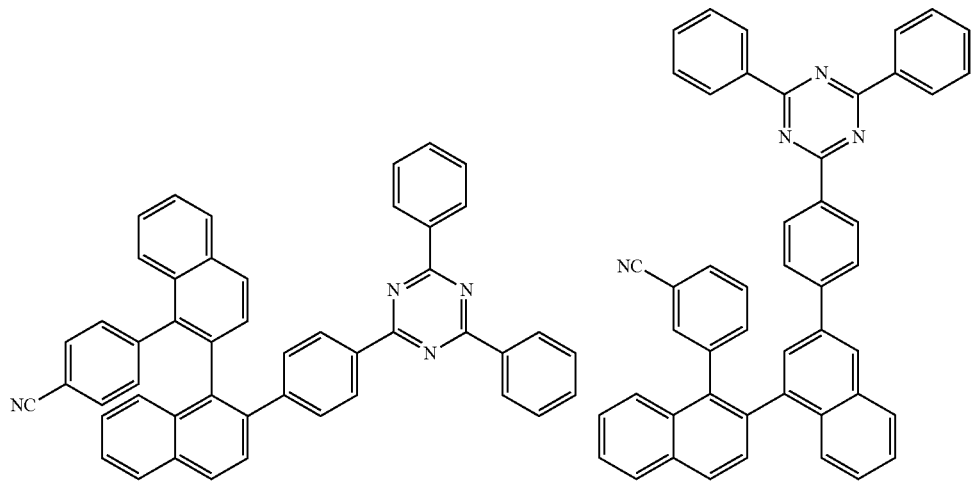
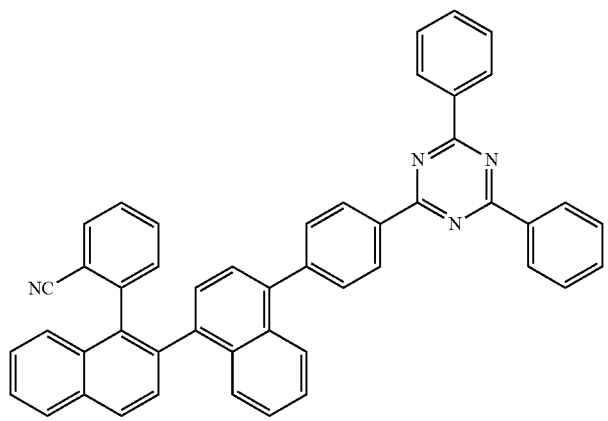
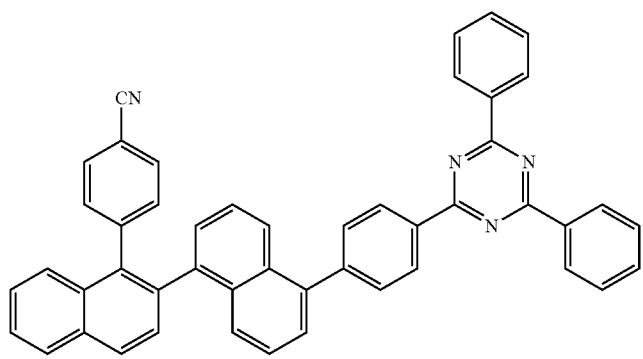

11
12
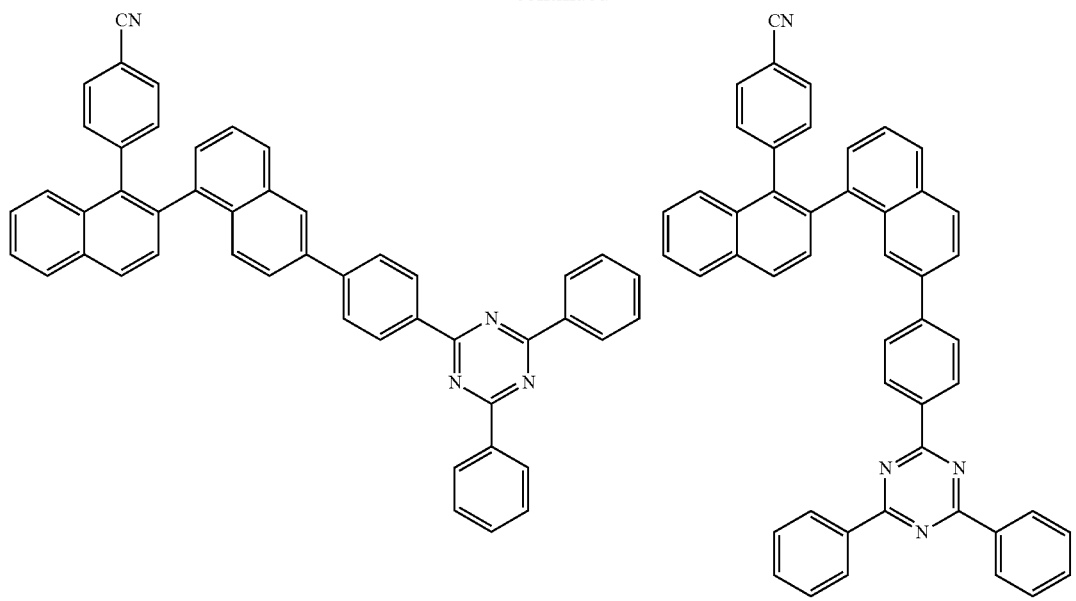
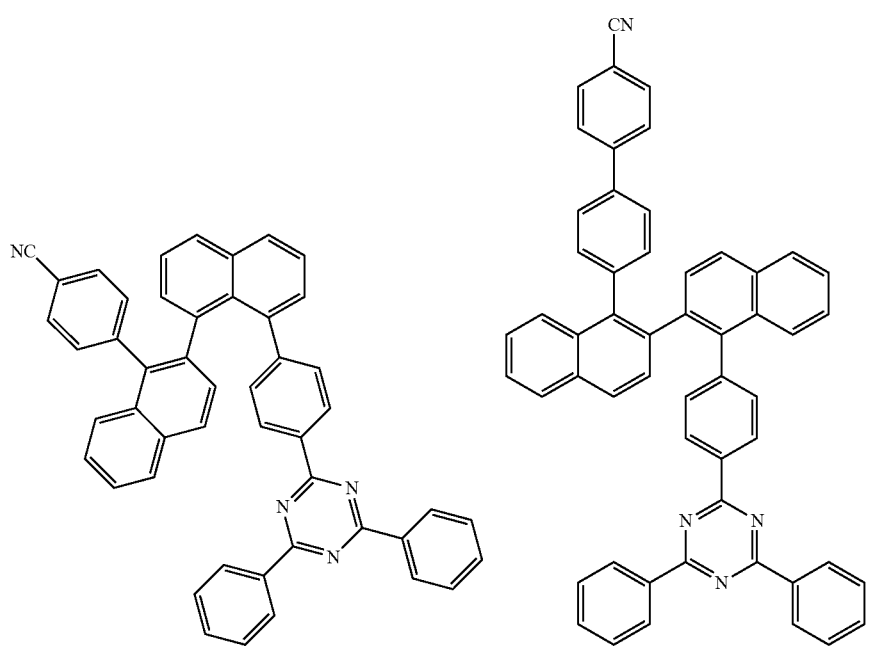

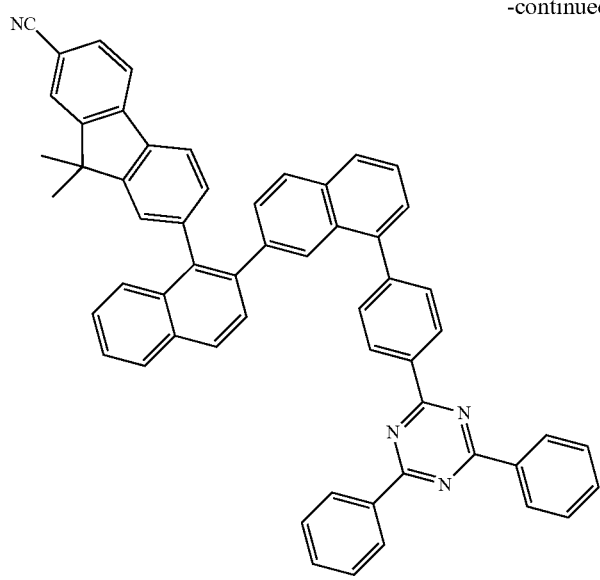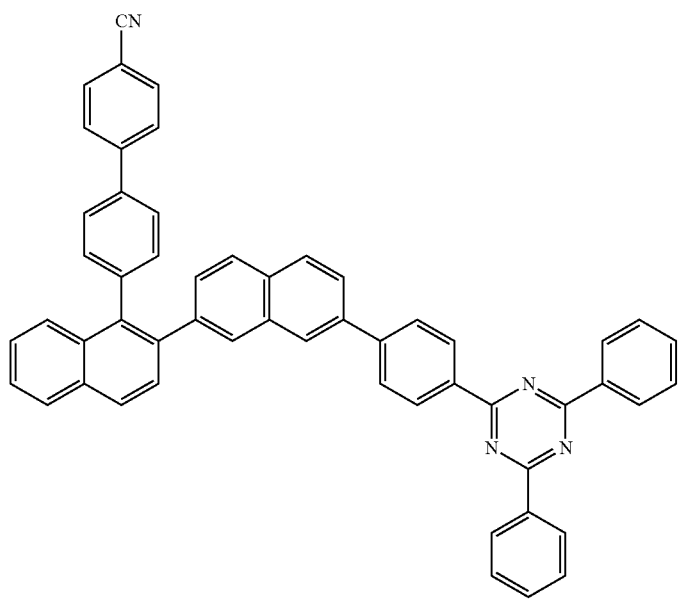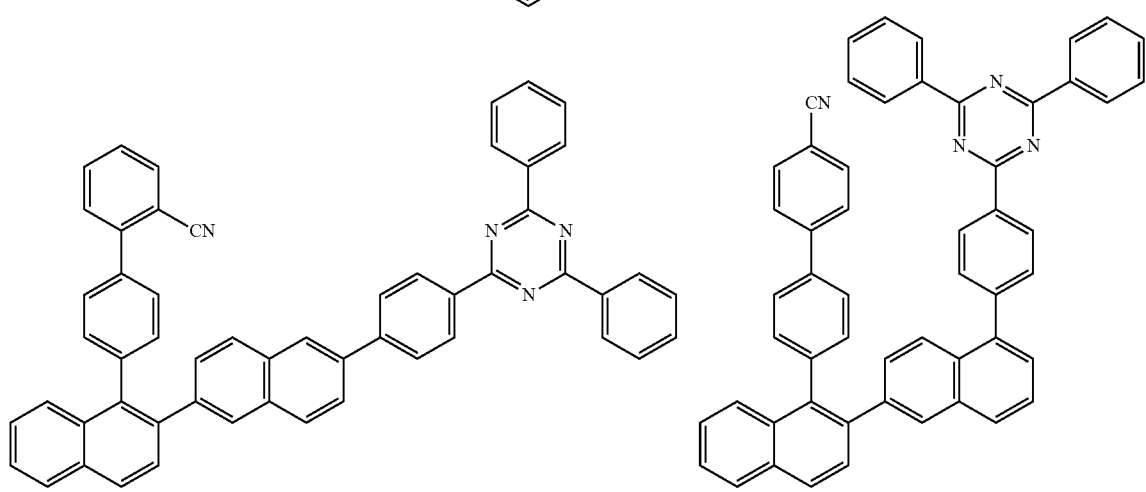

-continued
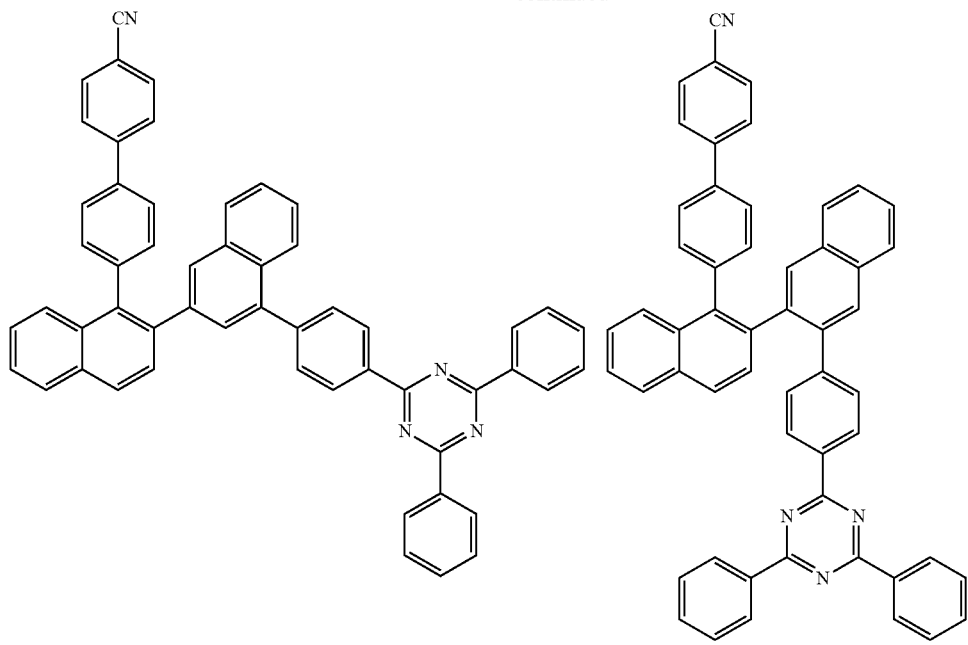
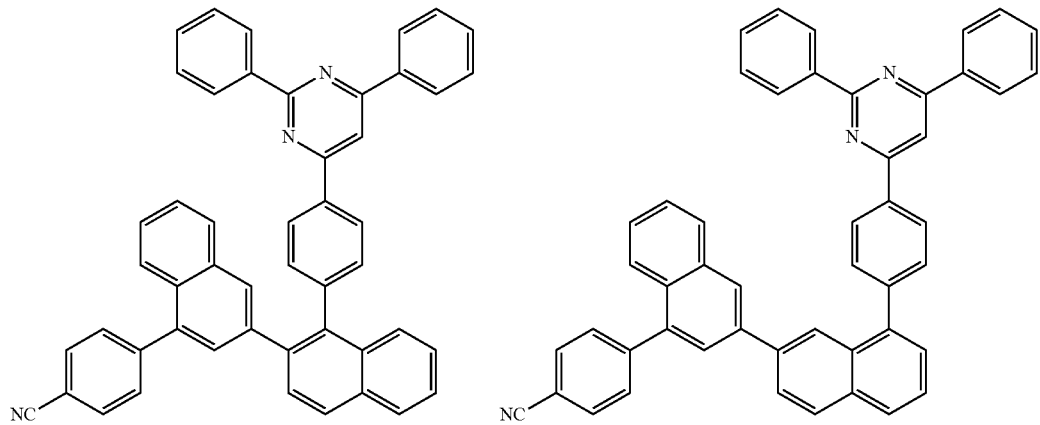
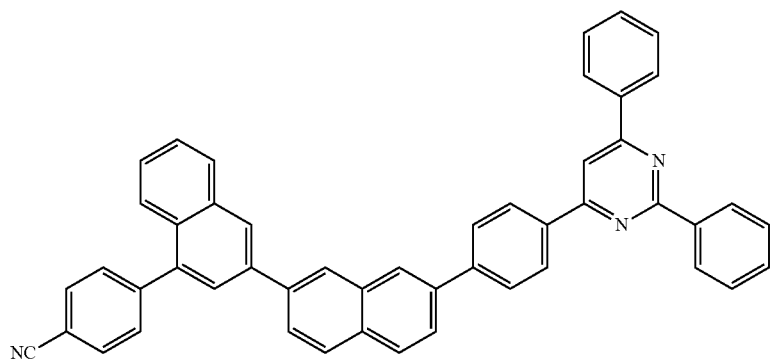

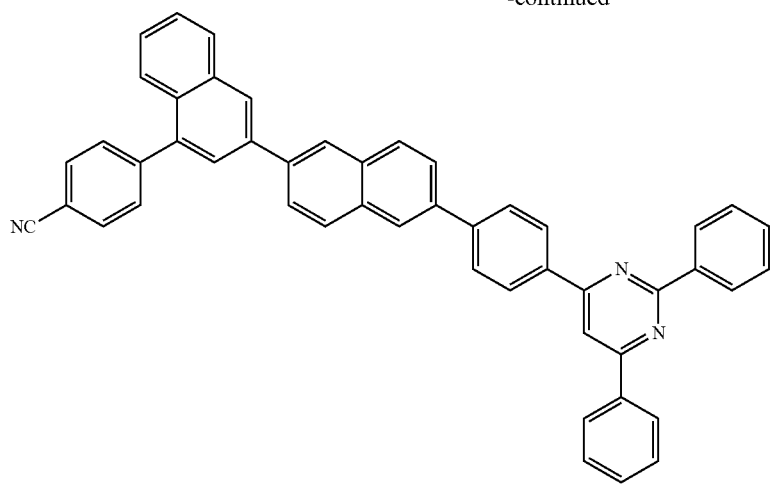
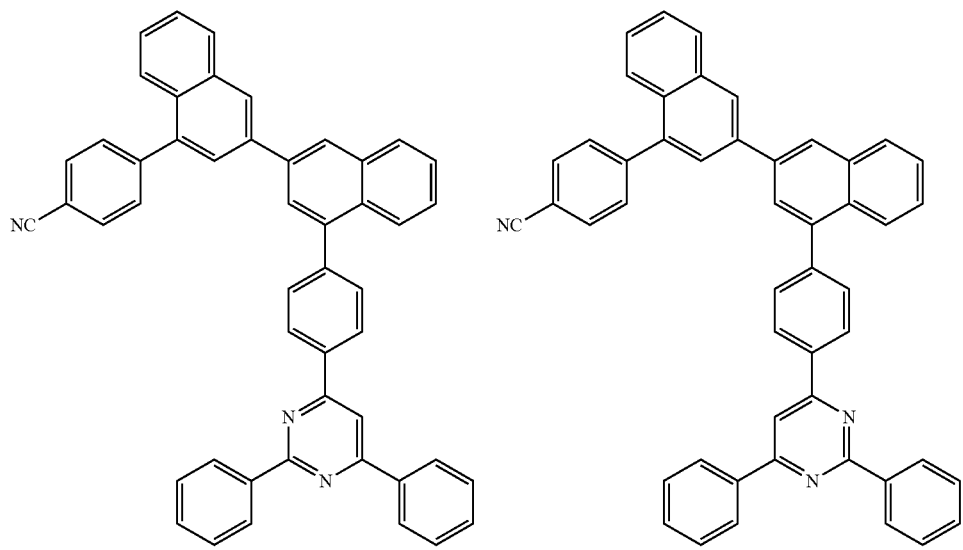
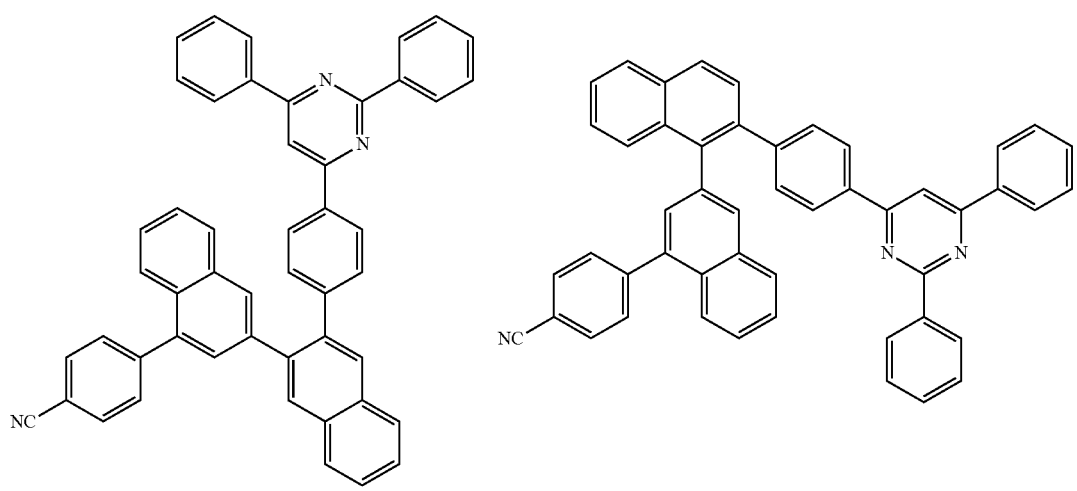

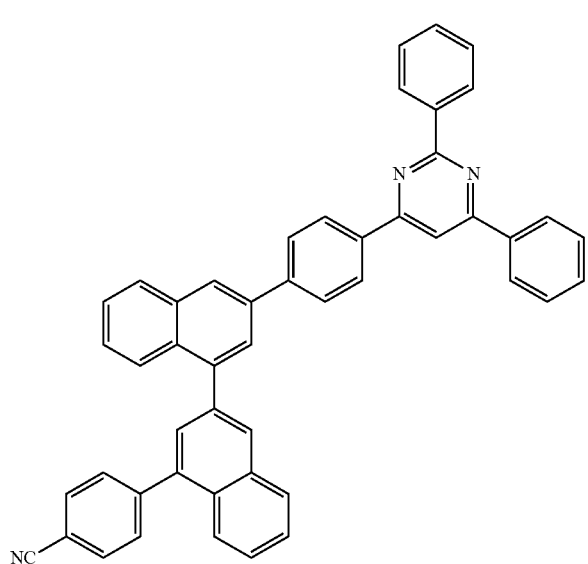
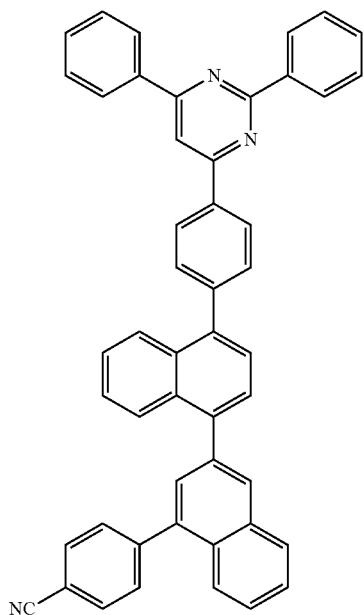
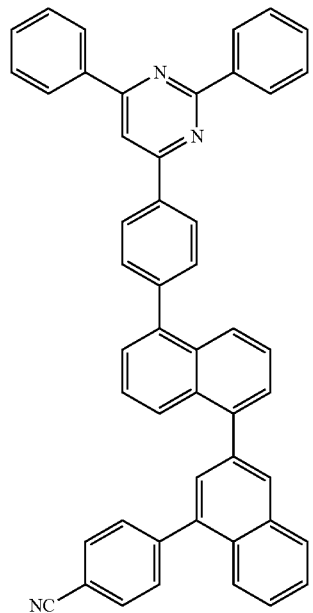
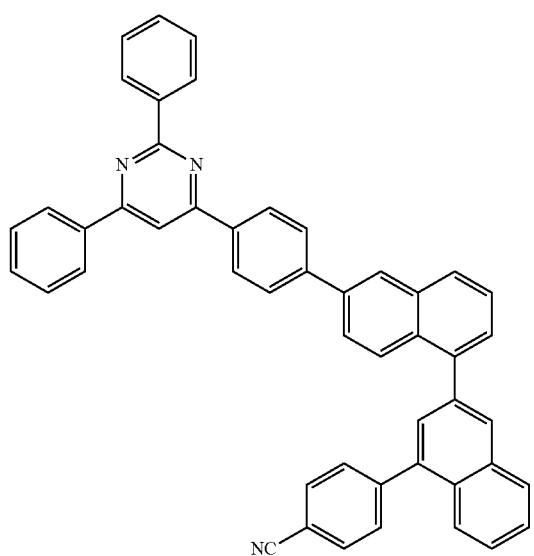

-continued
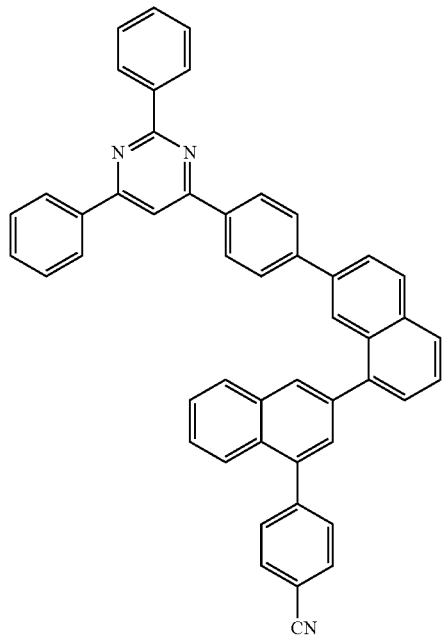
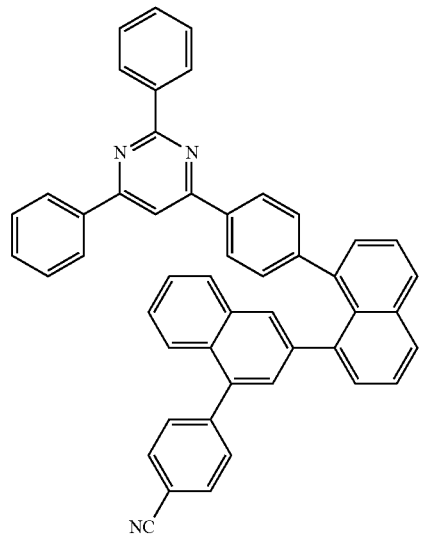
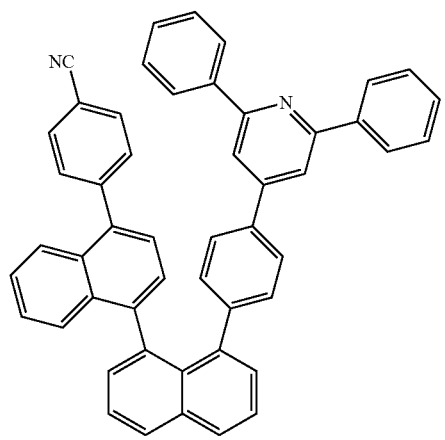
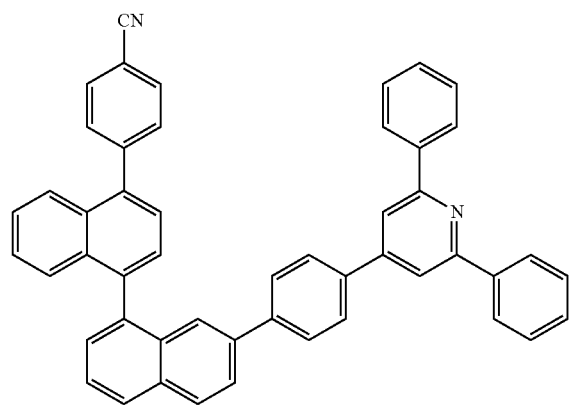
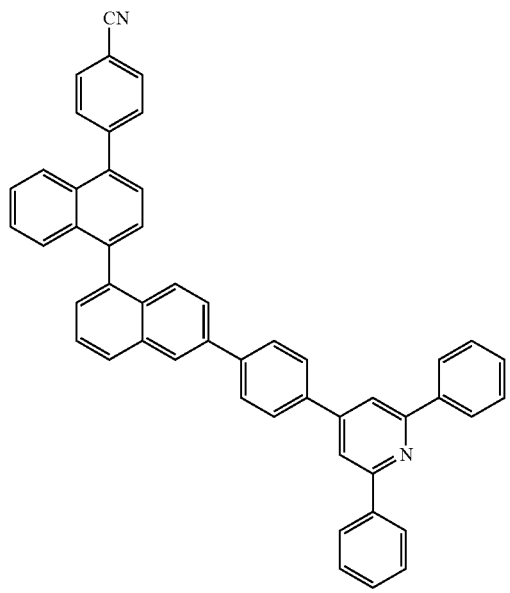
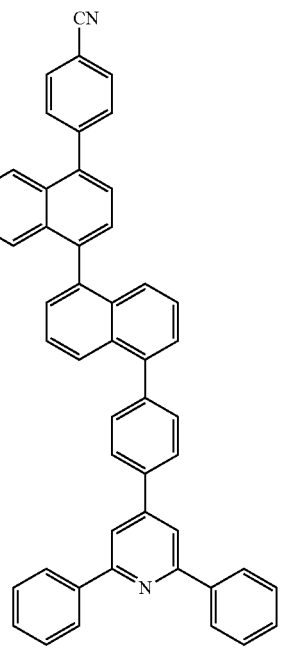

-continued
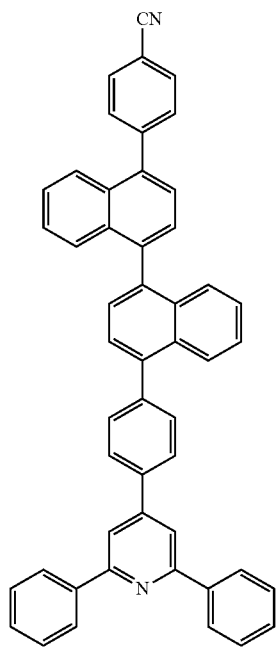
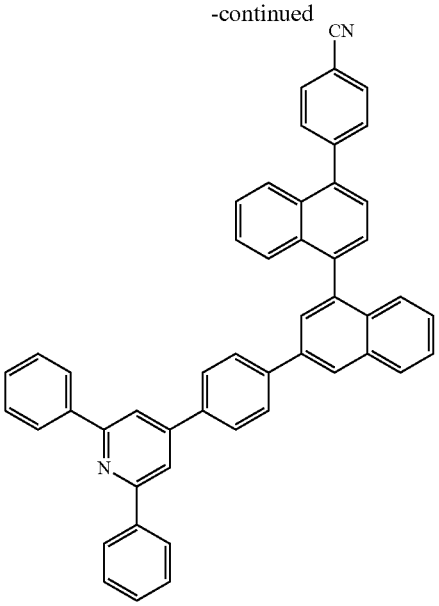
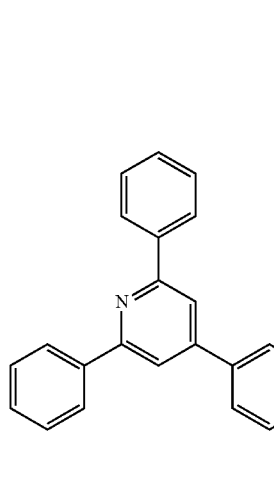
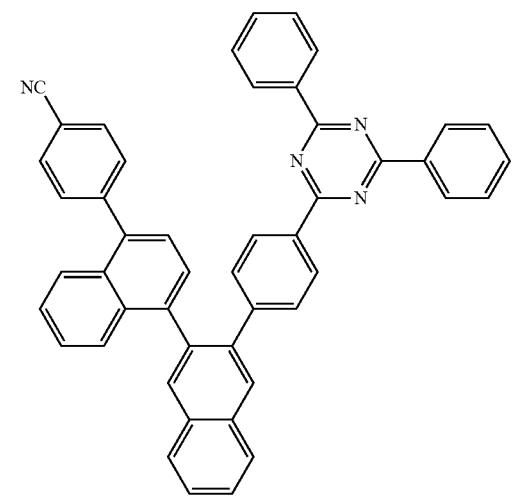
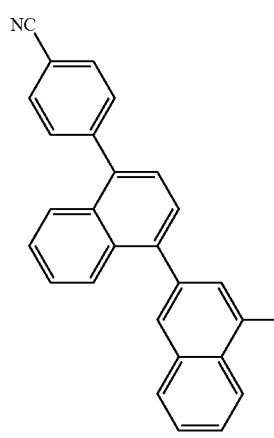
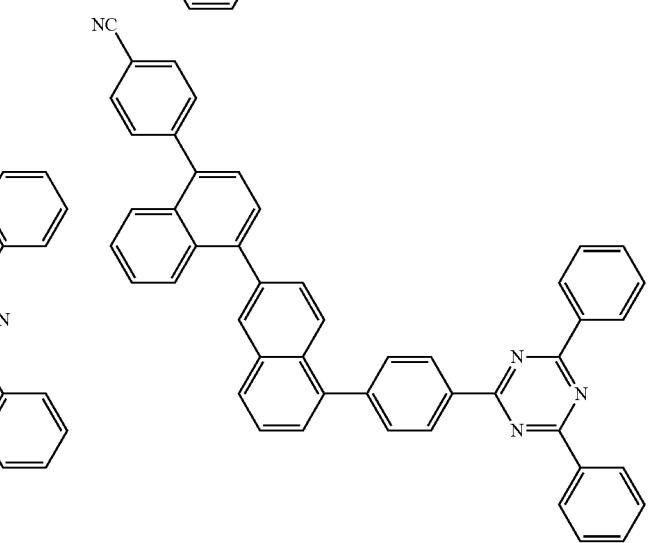

-continued
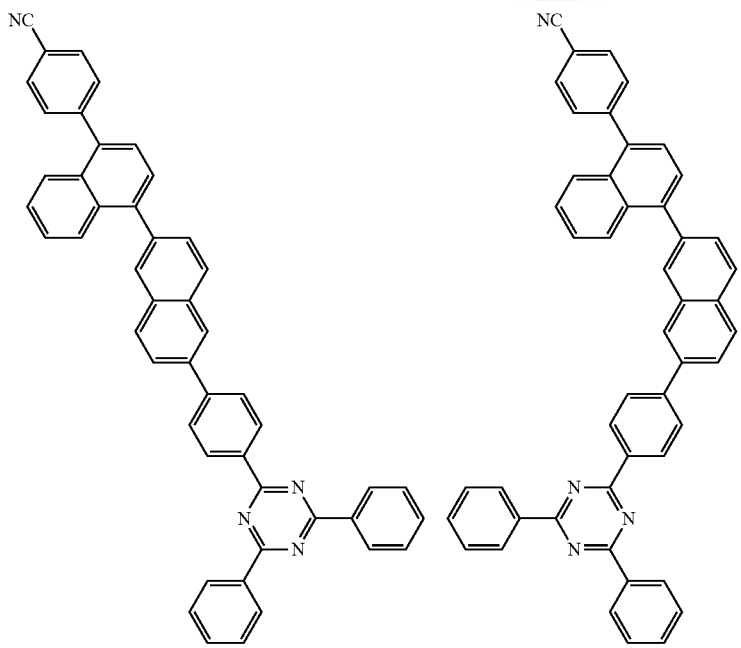
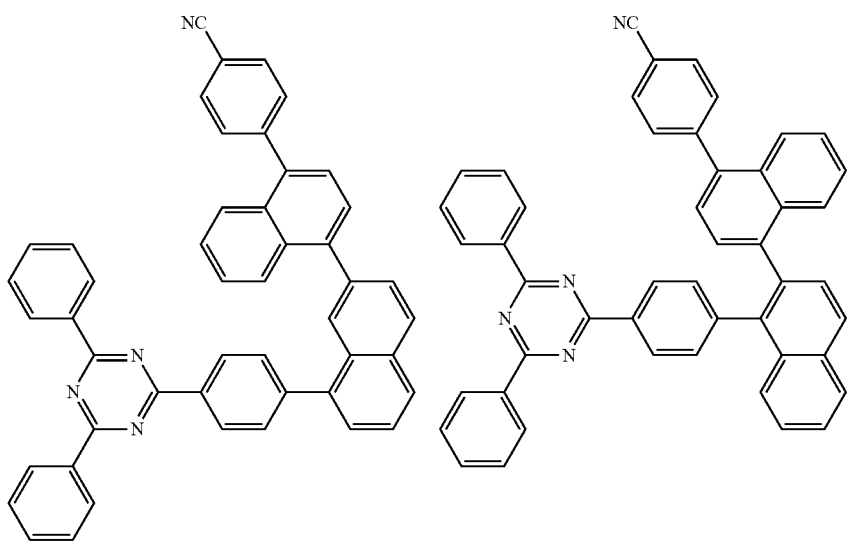
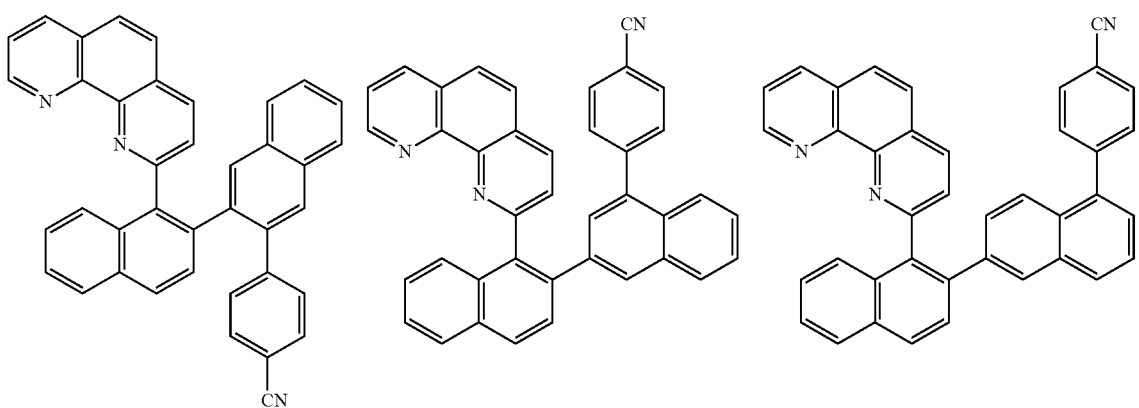

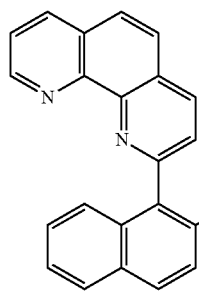
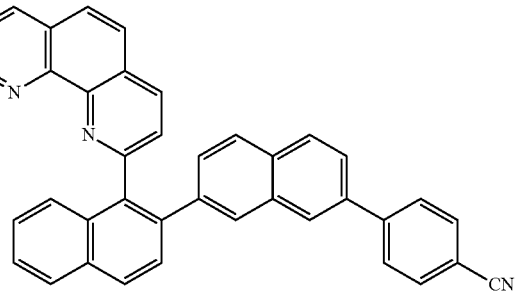
-continued
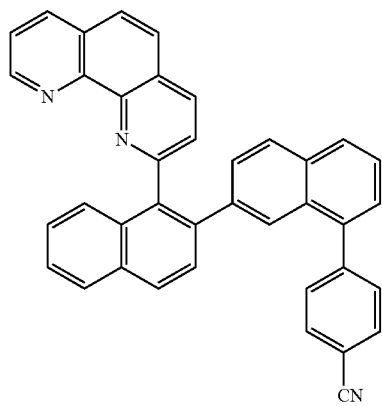
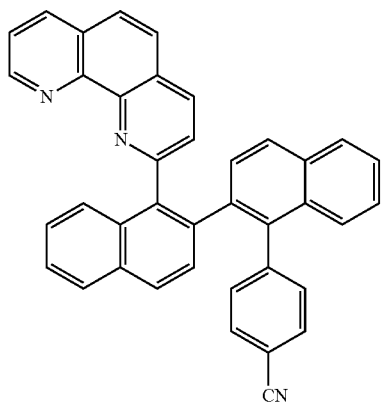
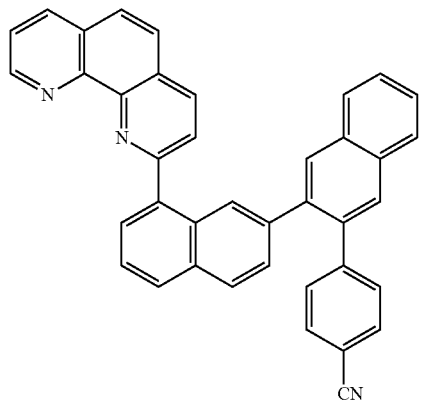
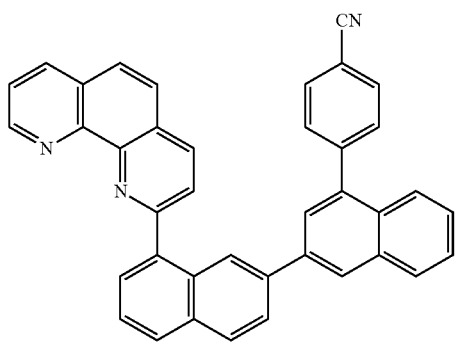
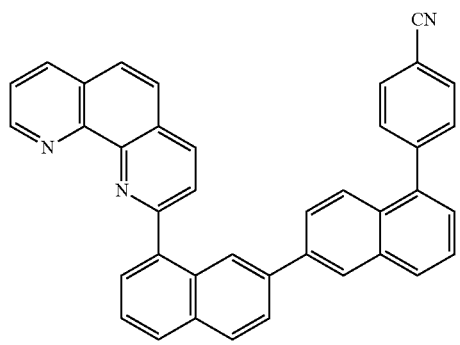
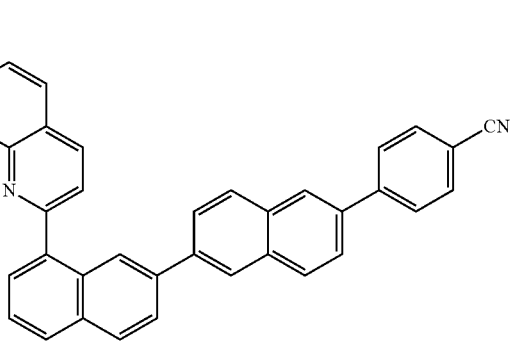

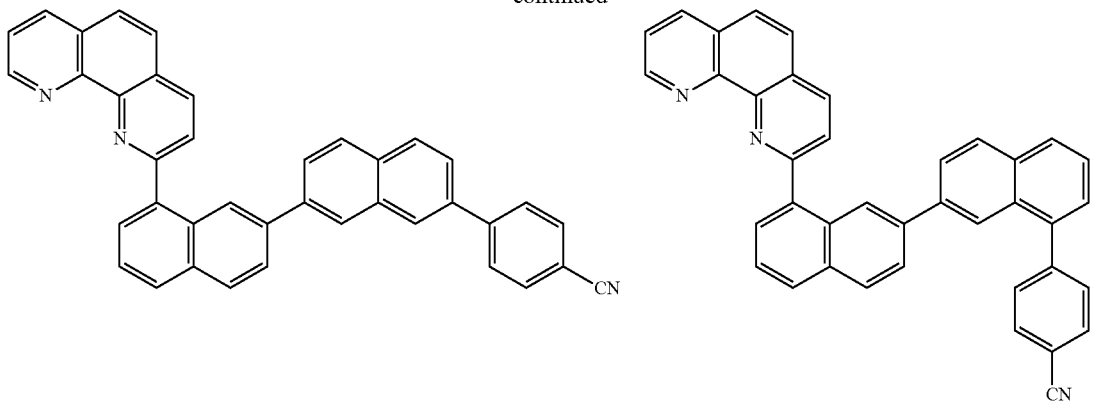
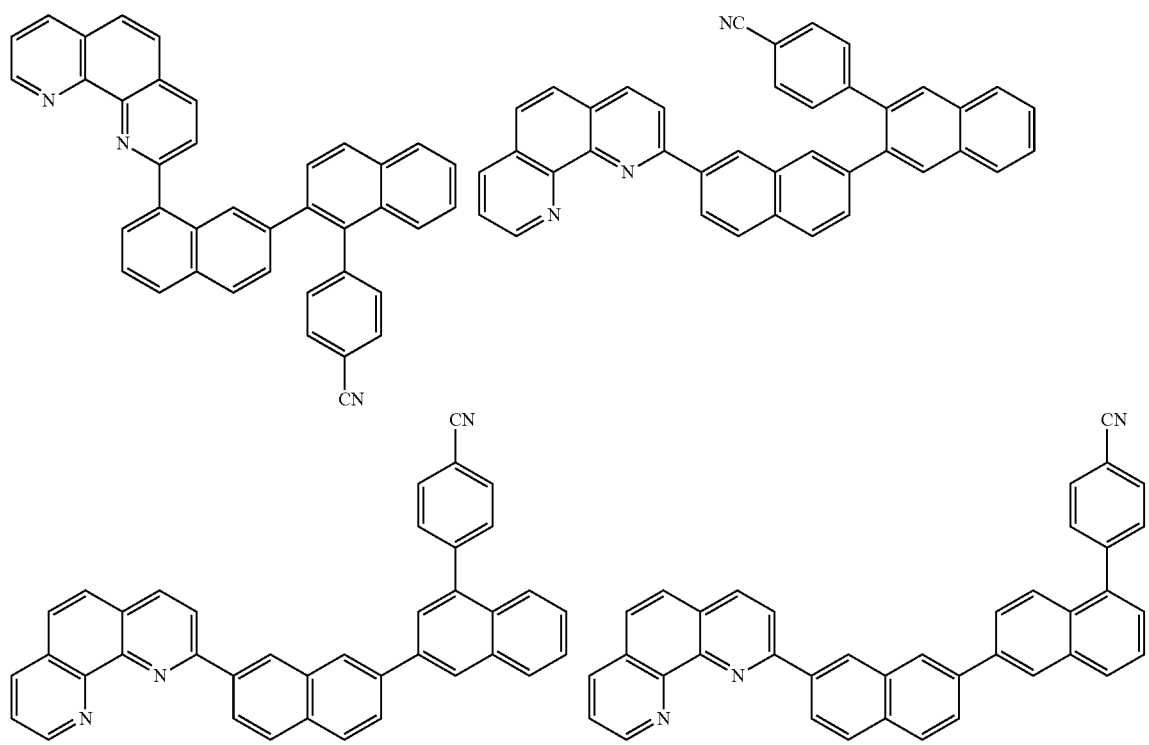
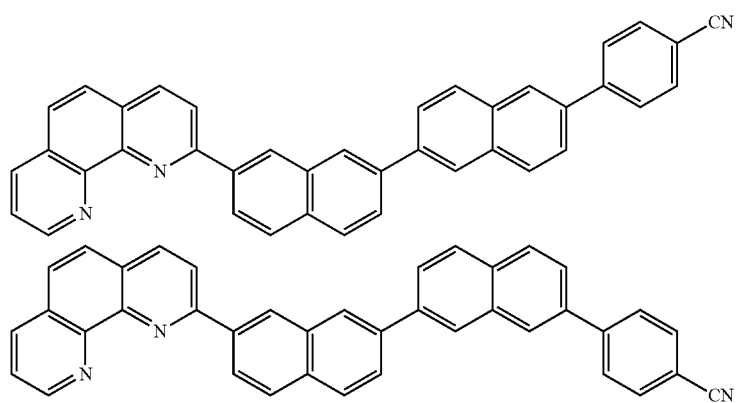

-continued
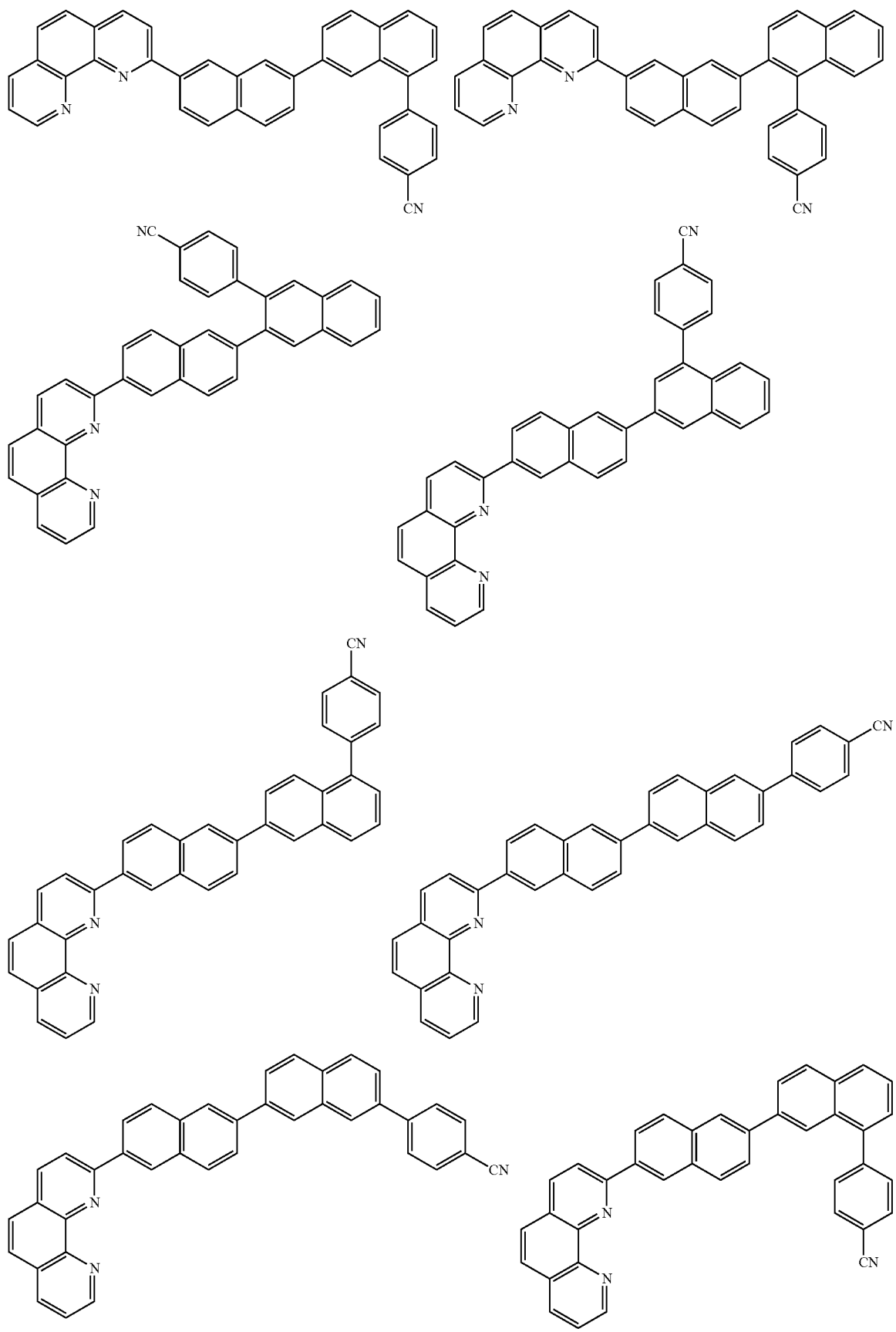

-continued
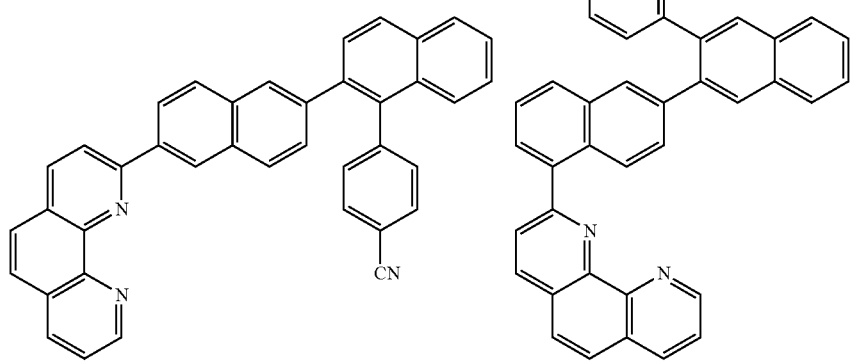
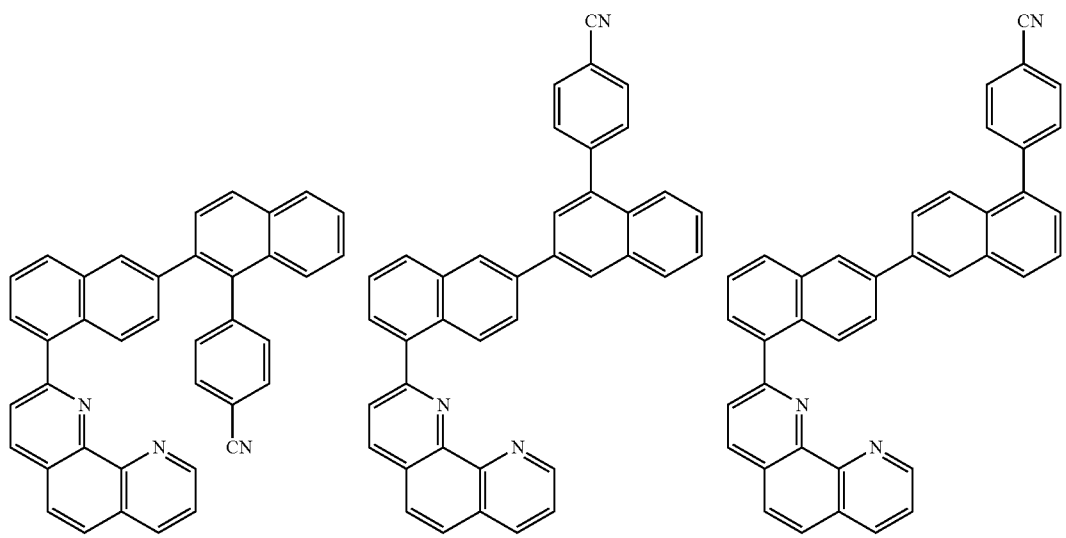
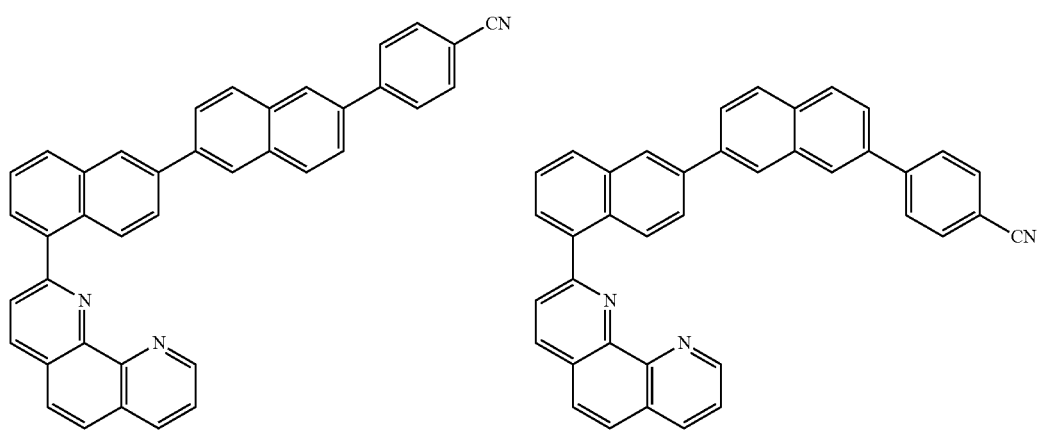

-continued
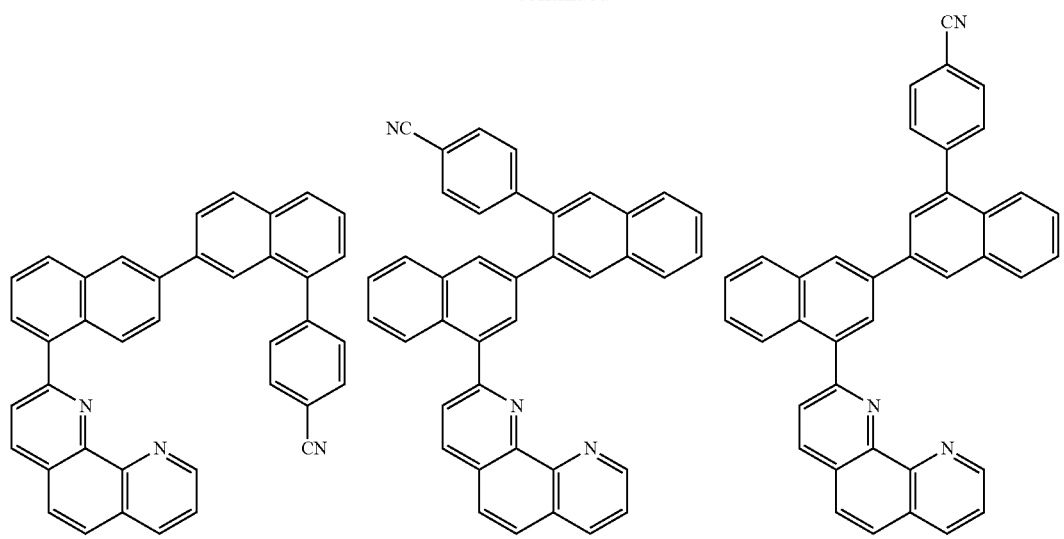
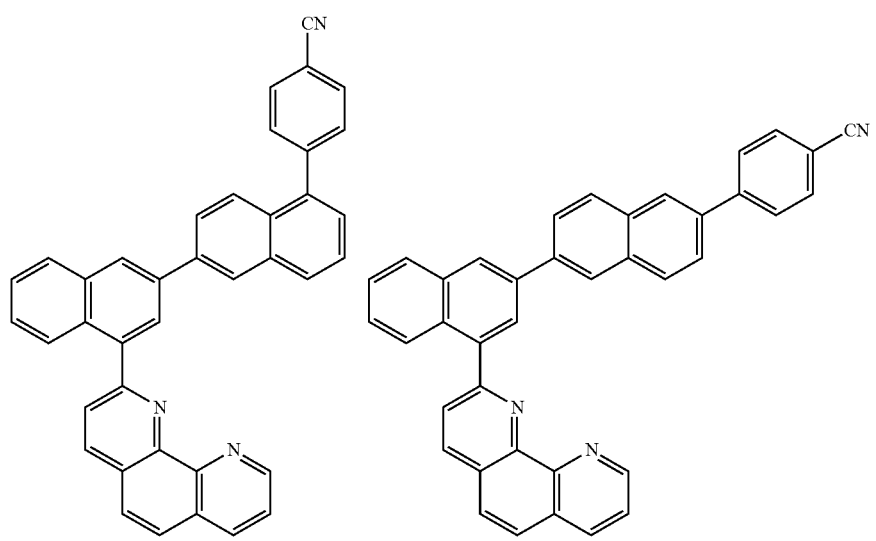
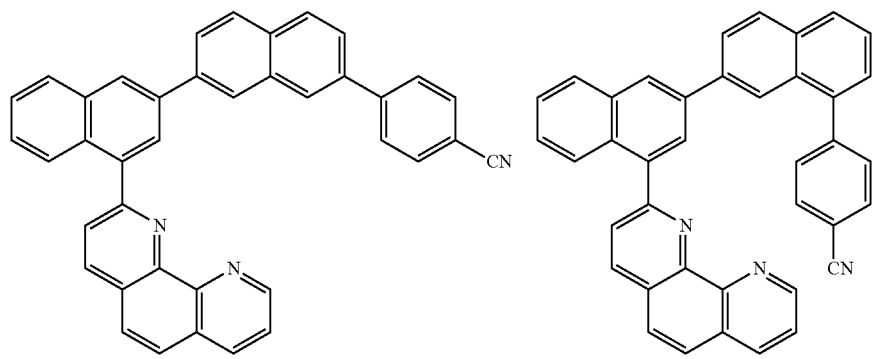

-continued
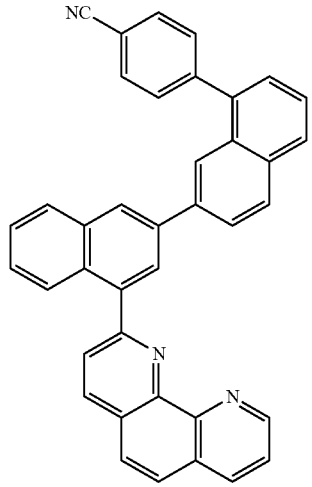
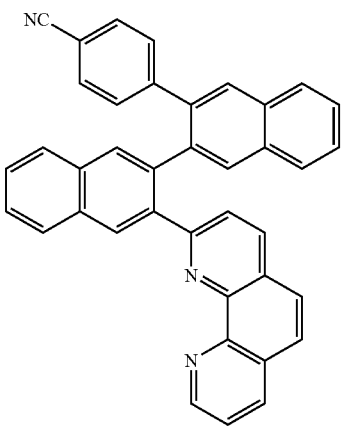
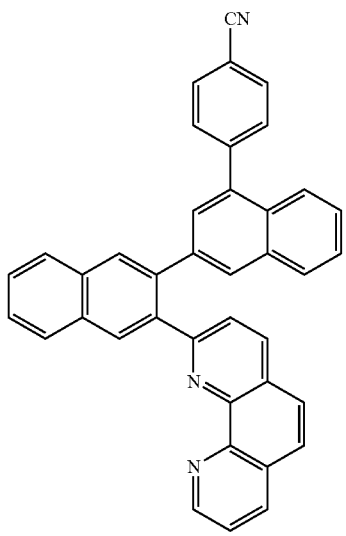
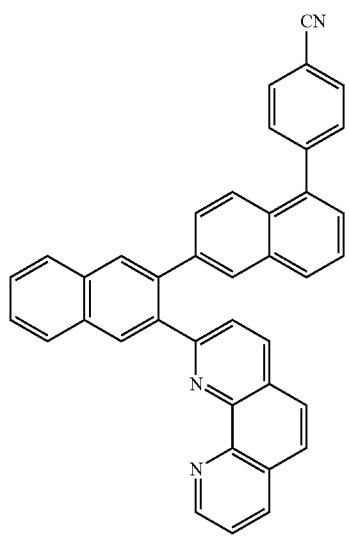
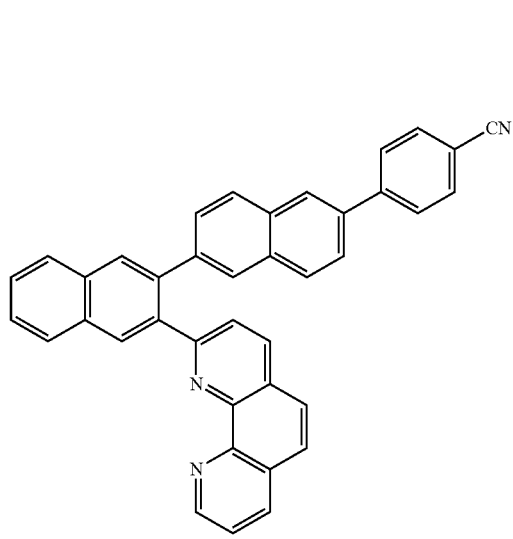
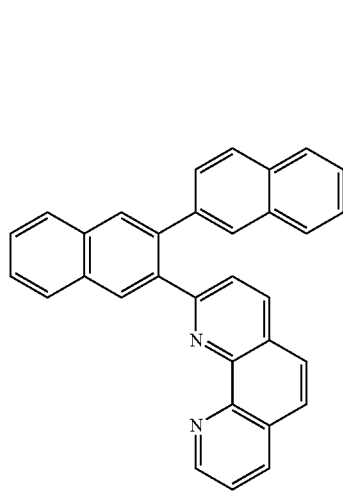
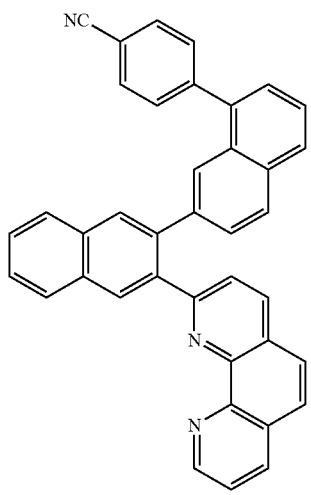
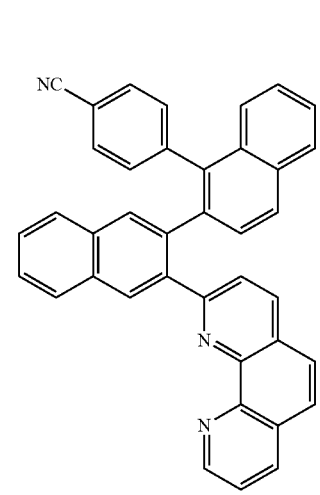

-continued
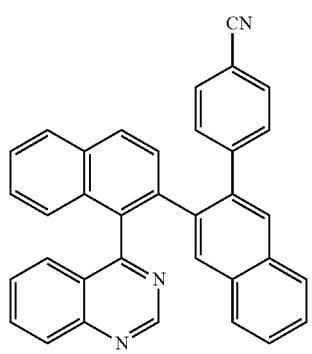
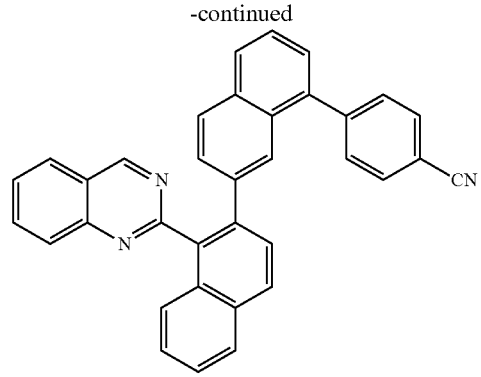
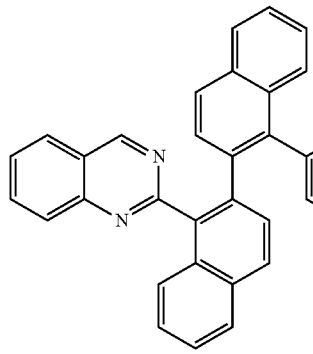
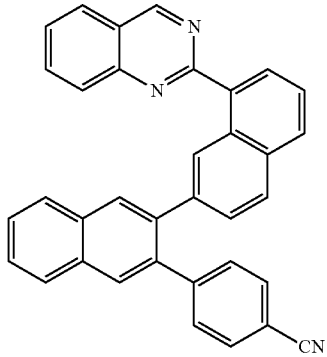
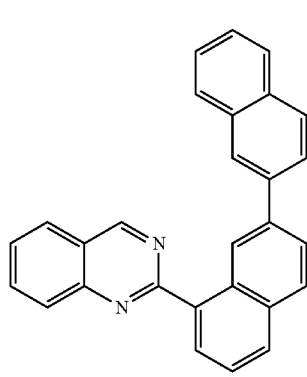
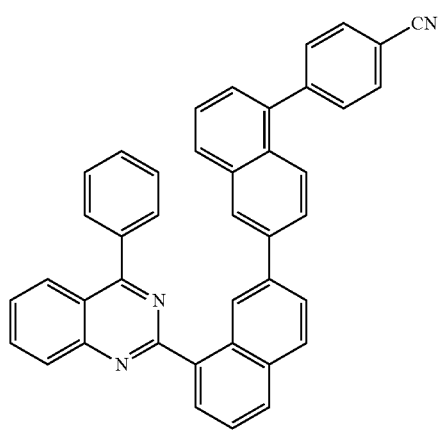
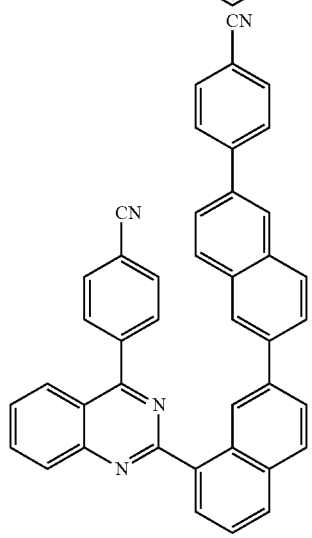
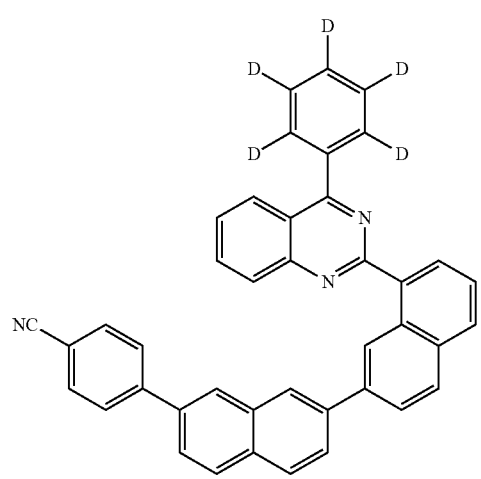
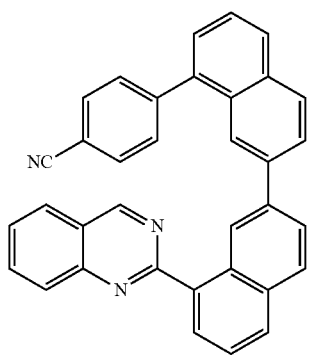

-continued
41 42
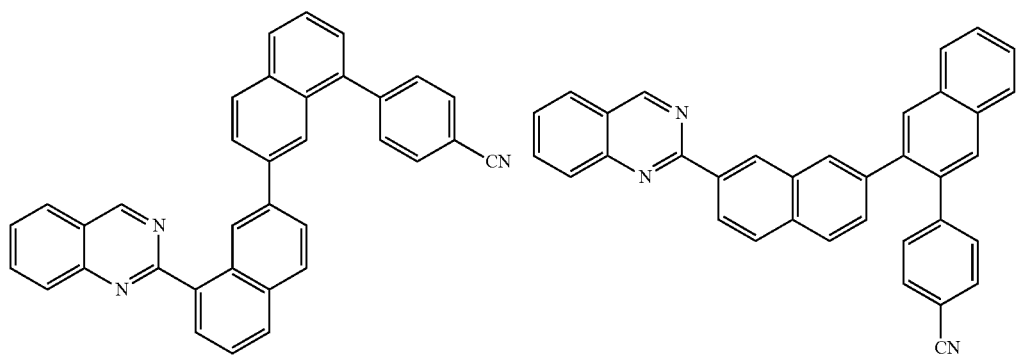
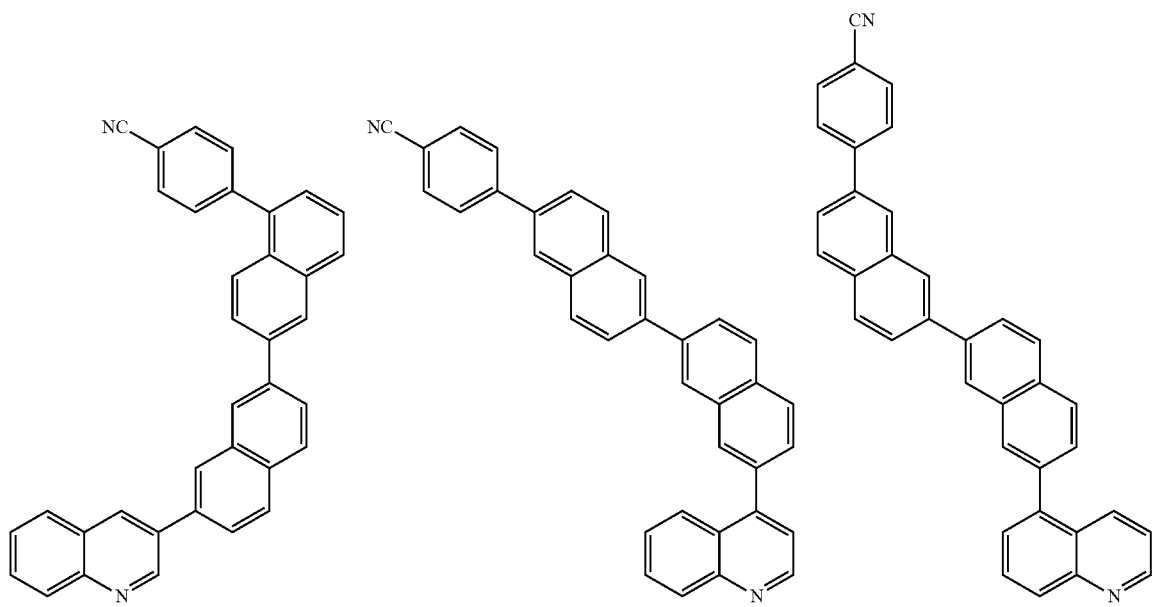
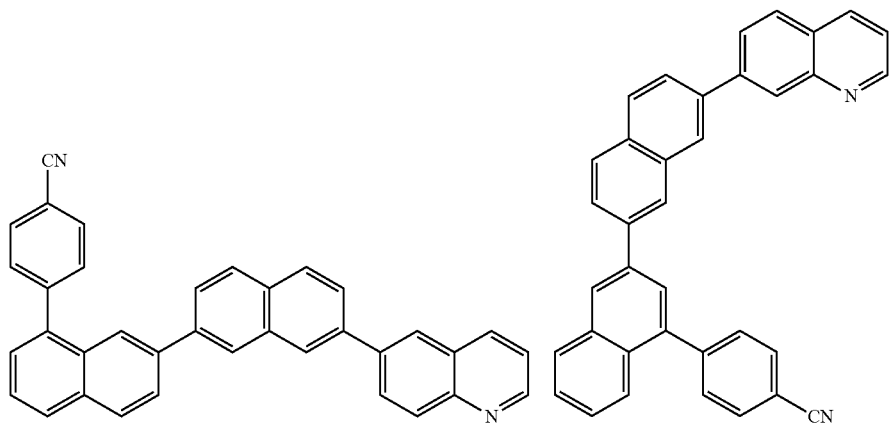

-continued
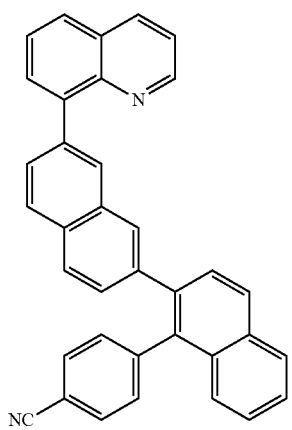
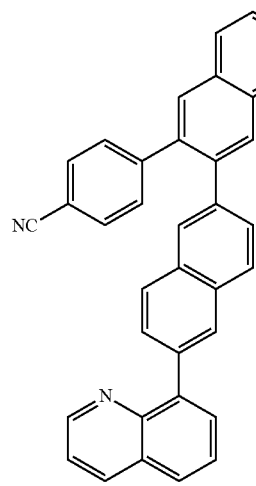
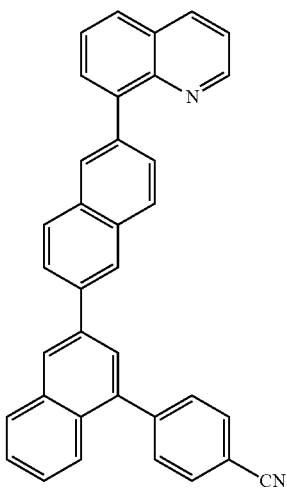
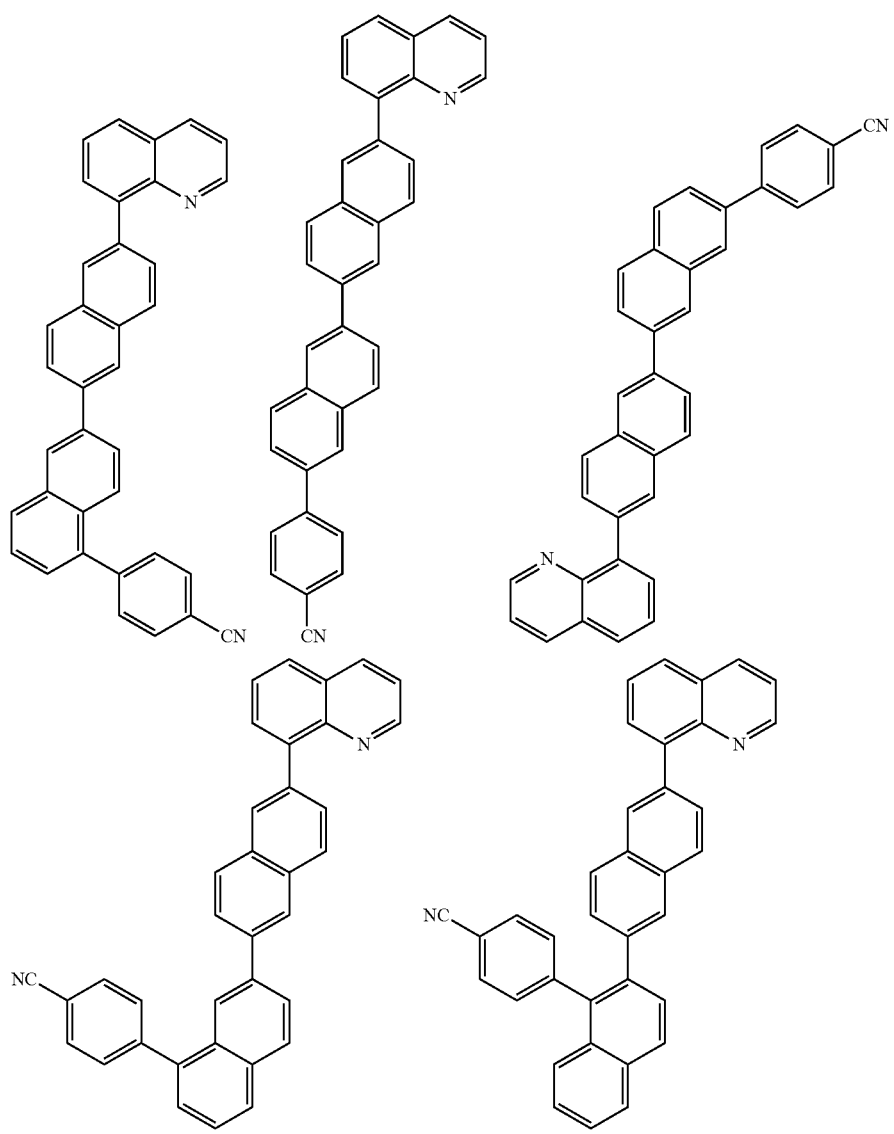

-continued
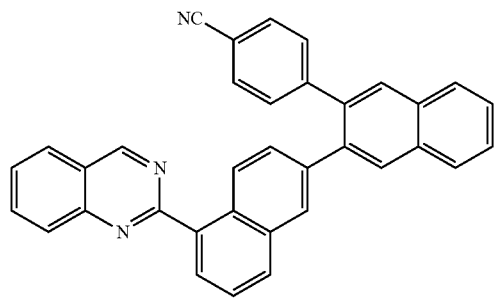
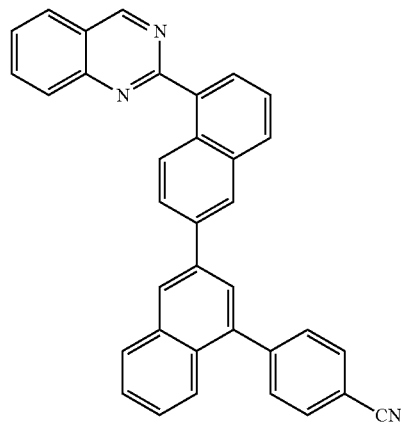
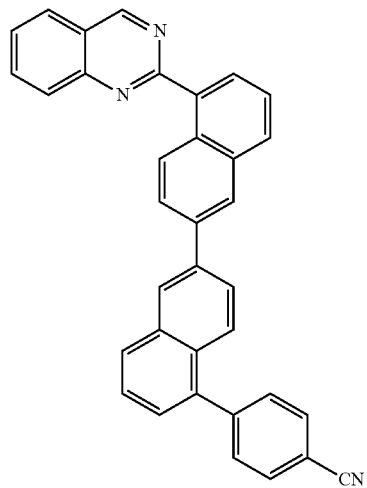
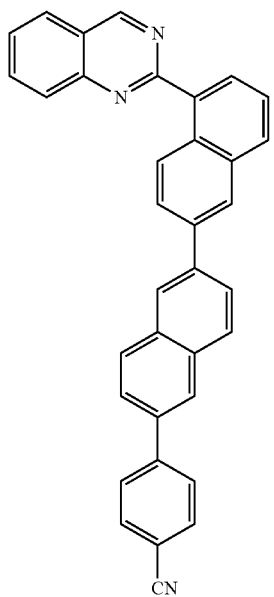
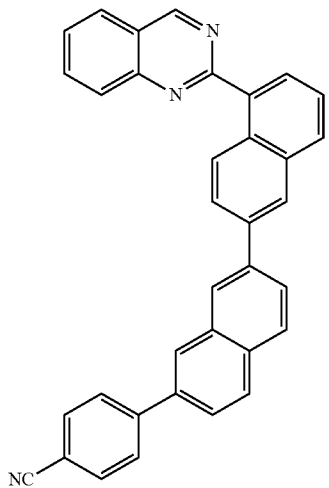
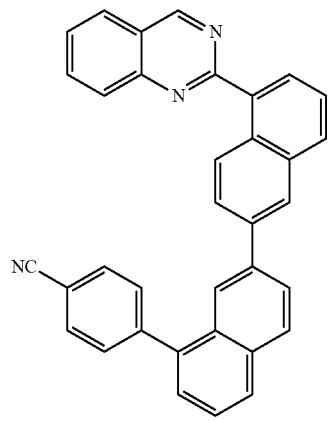
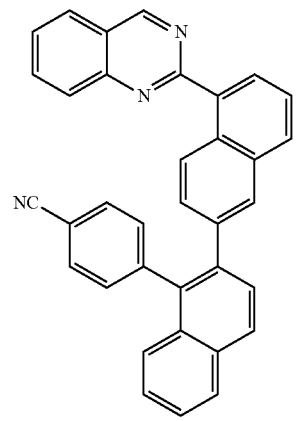
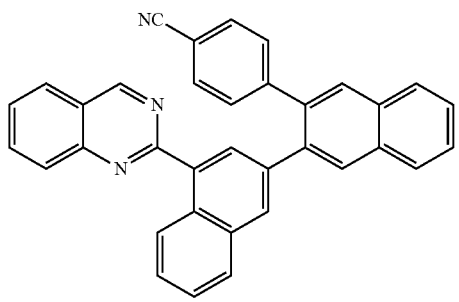

47
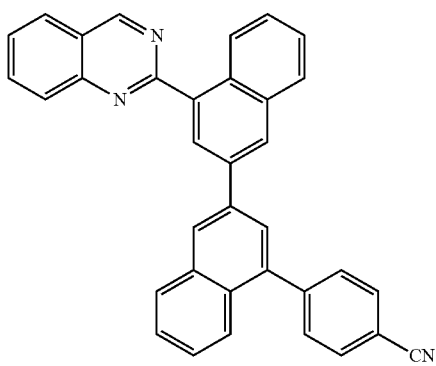
-continued
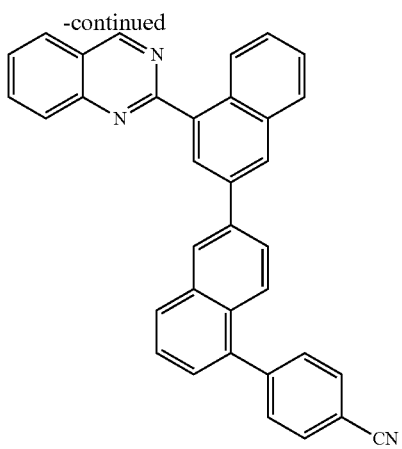
48
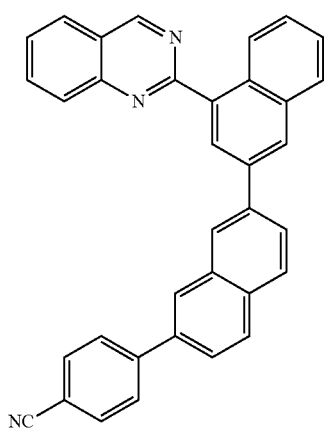
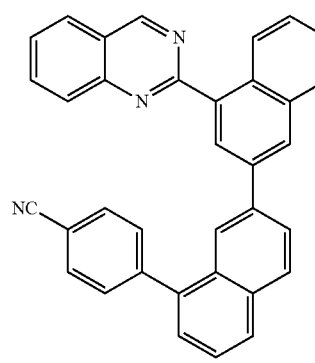
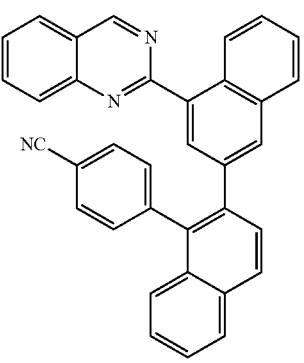
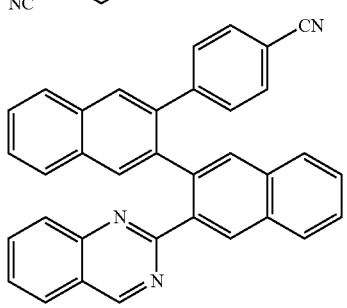
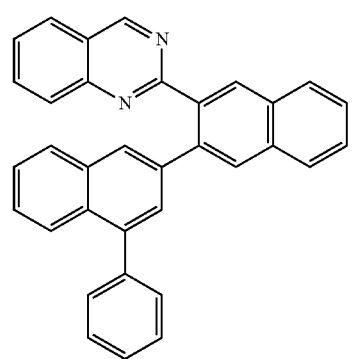
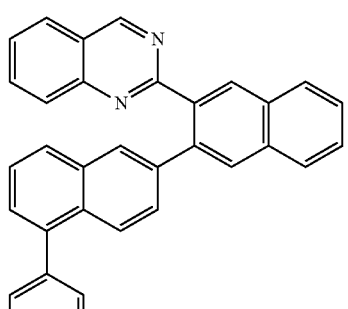
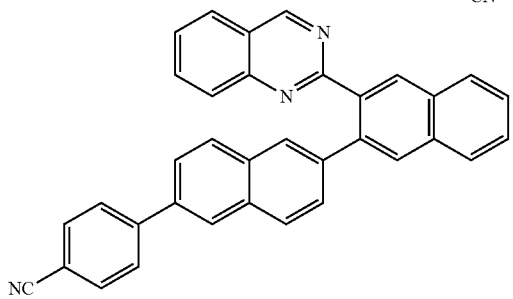
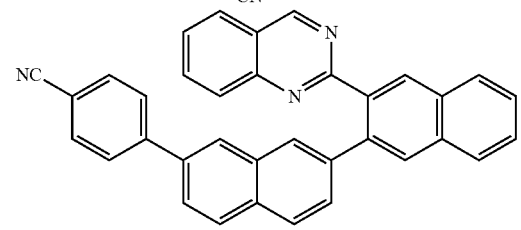

-continued
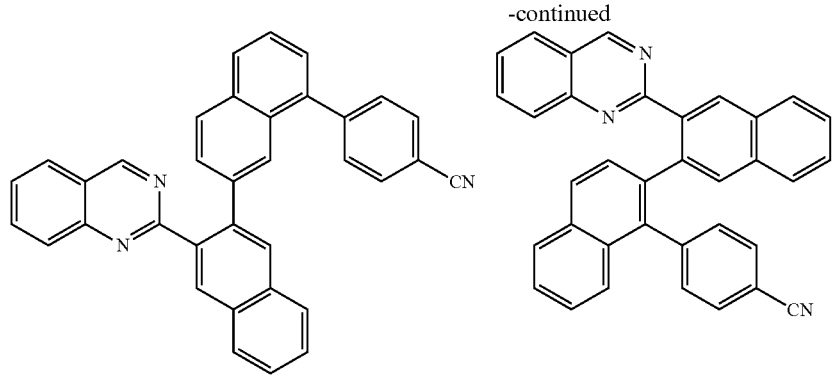
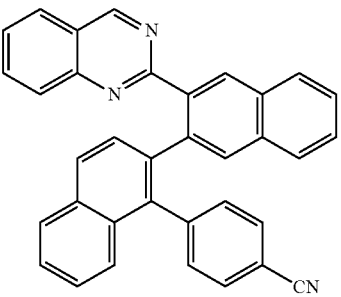
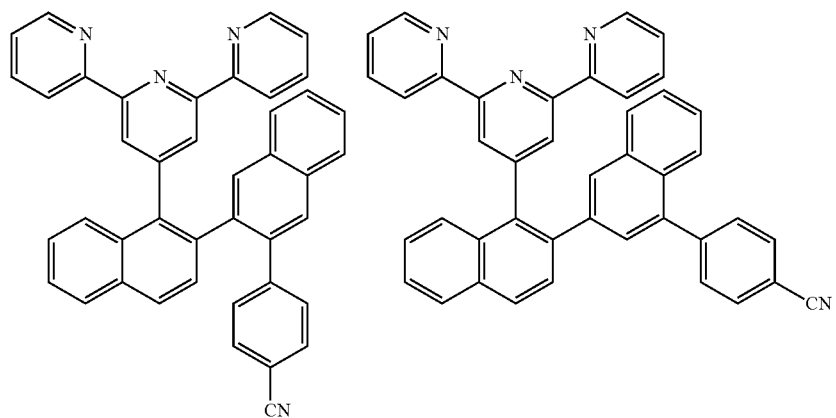
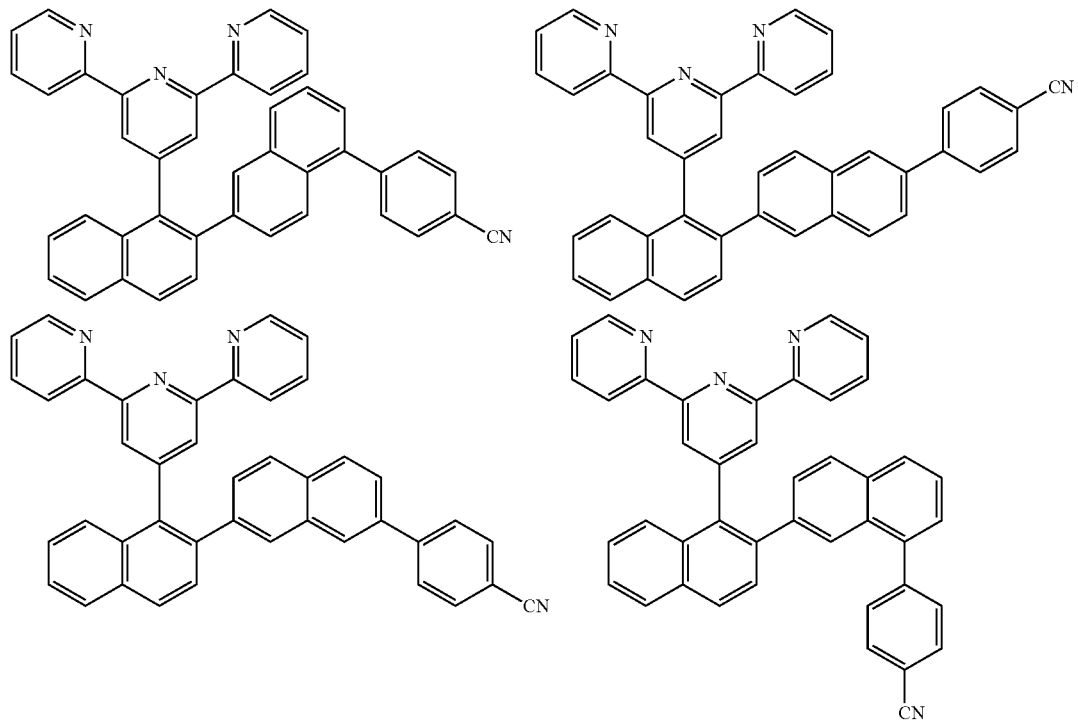

-continued
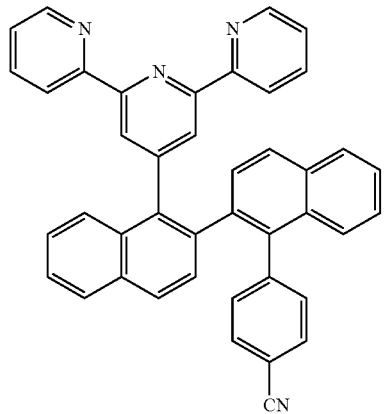
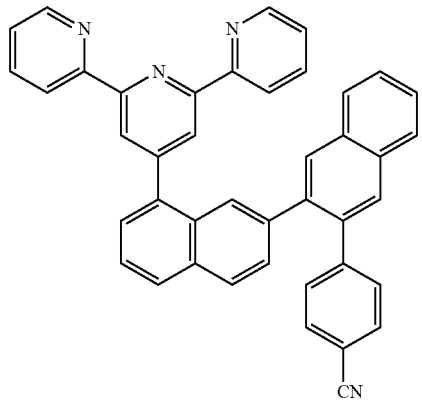
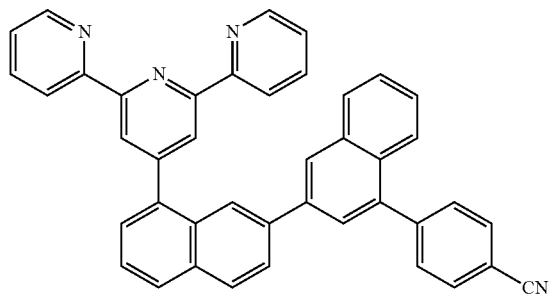
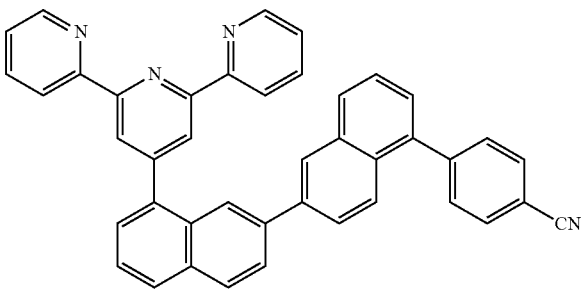
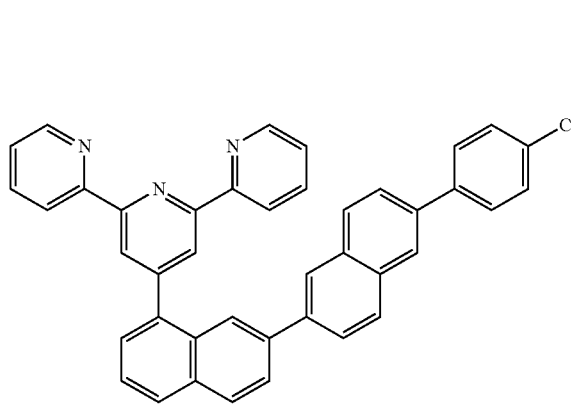
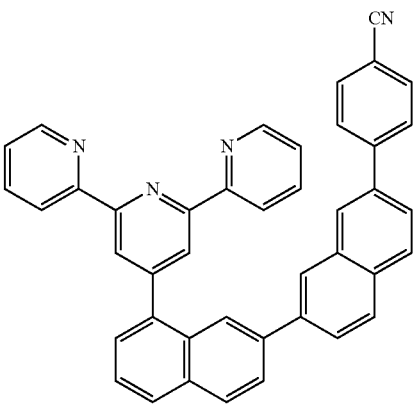
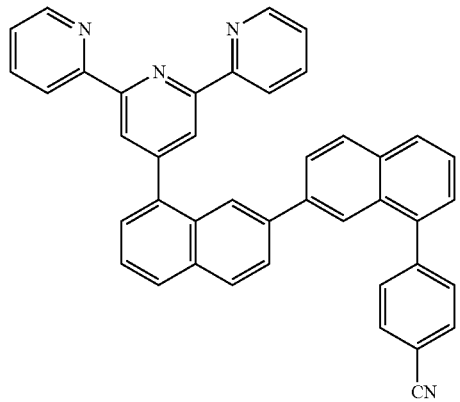
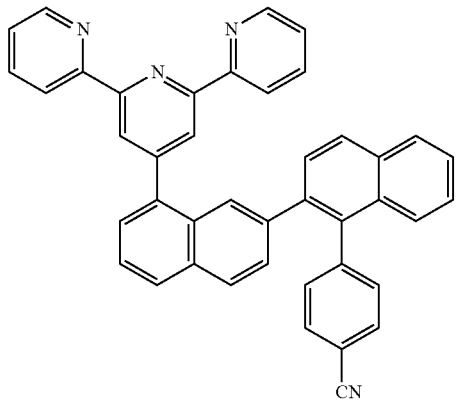

-continued
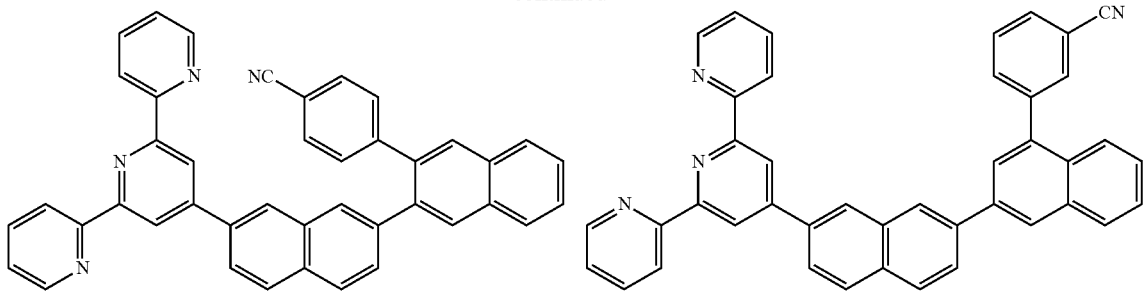
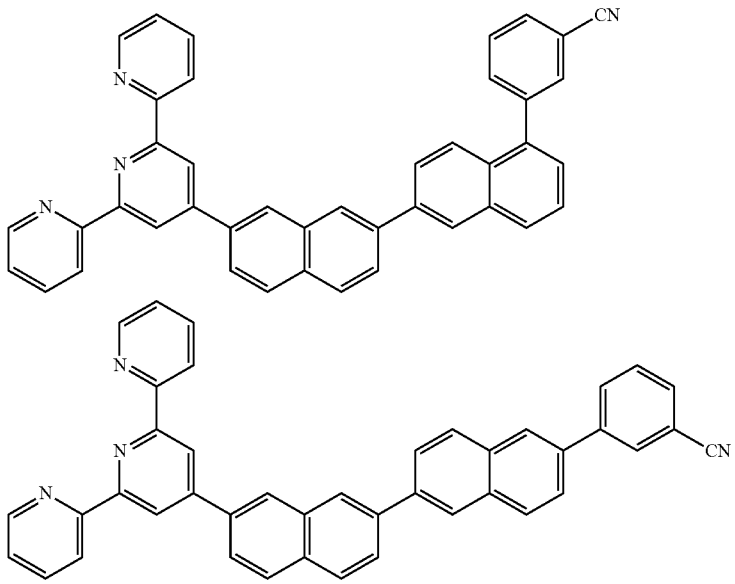
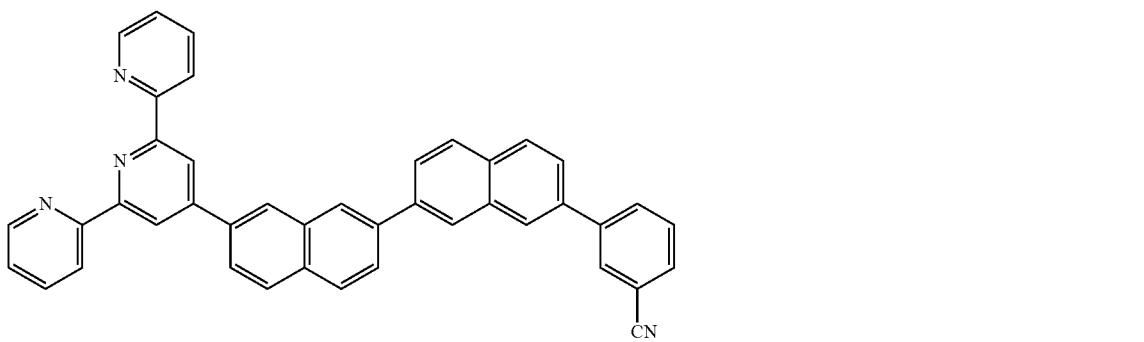
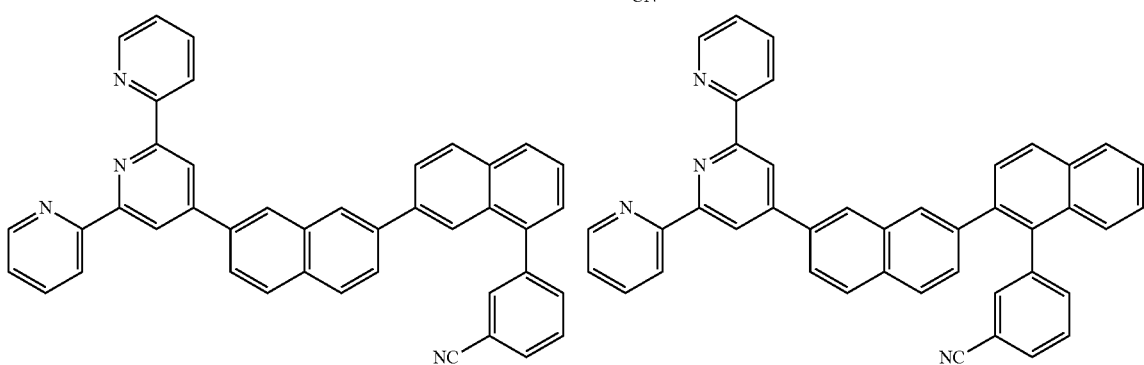

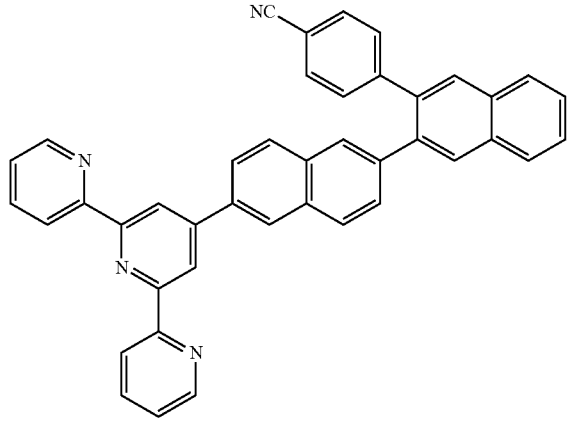
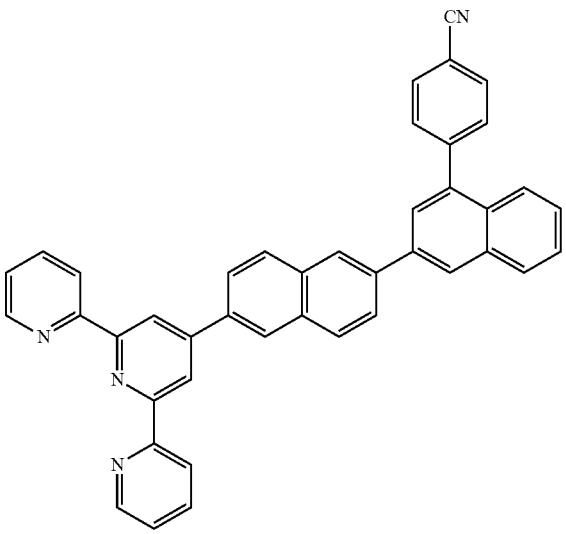
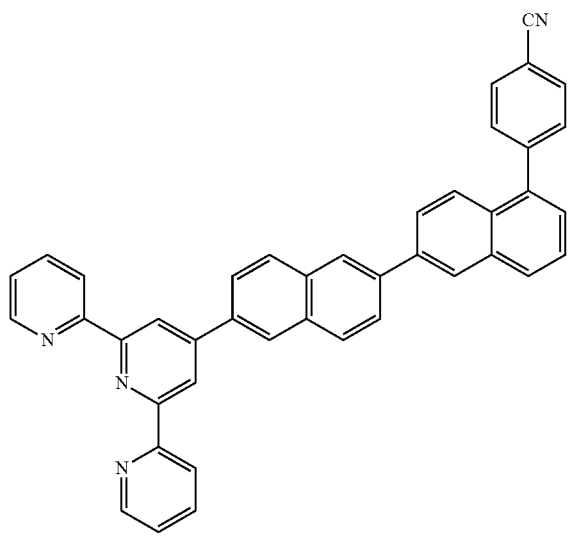
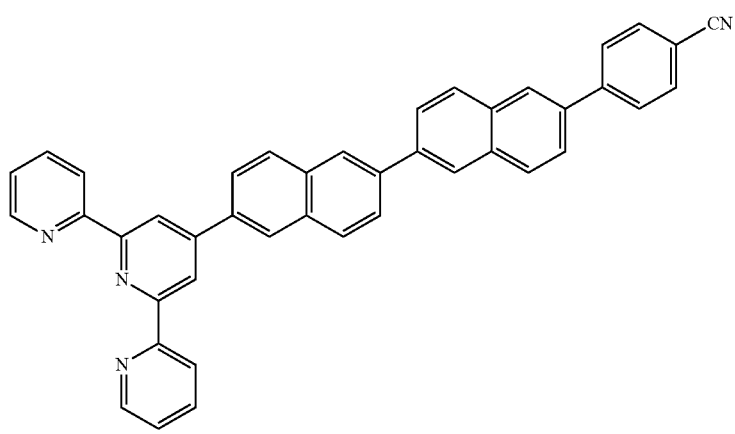

-continued
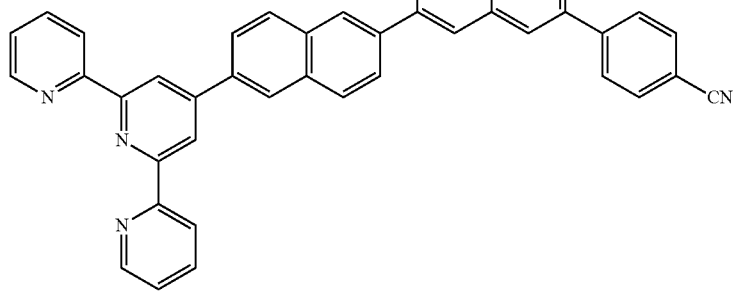
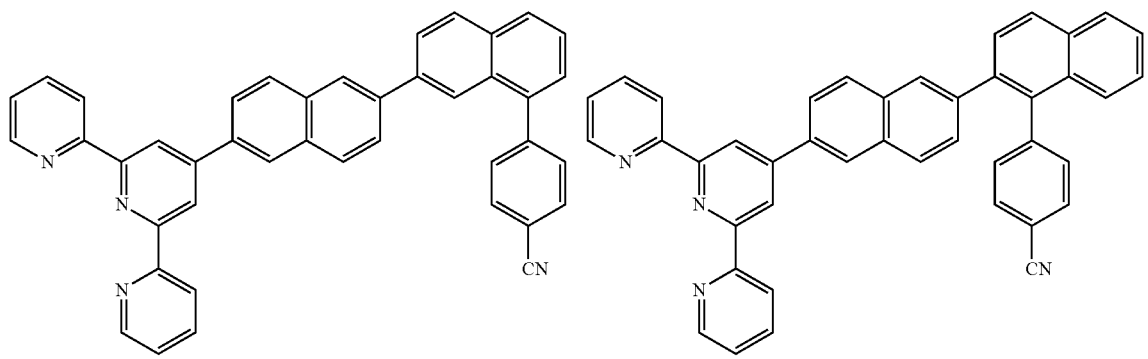
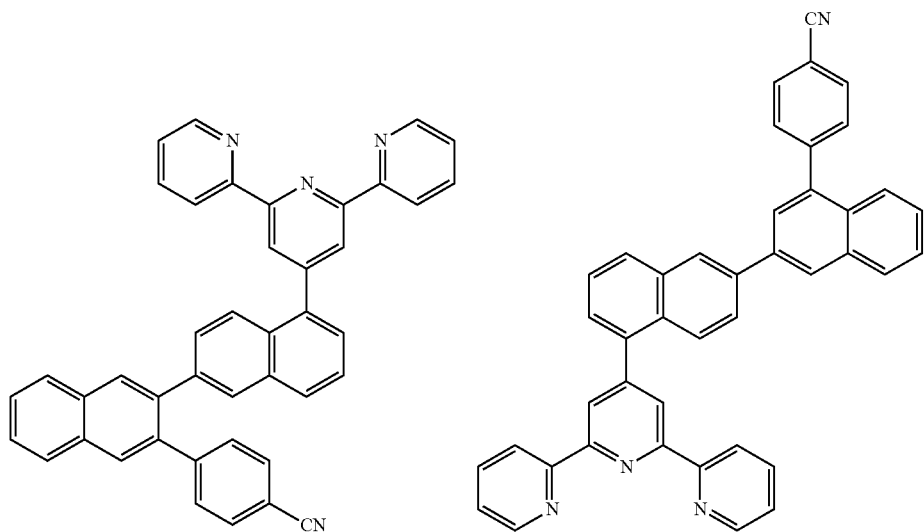

-continued
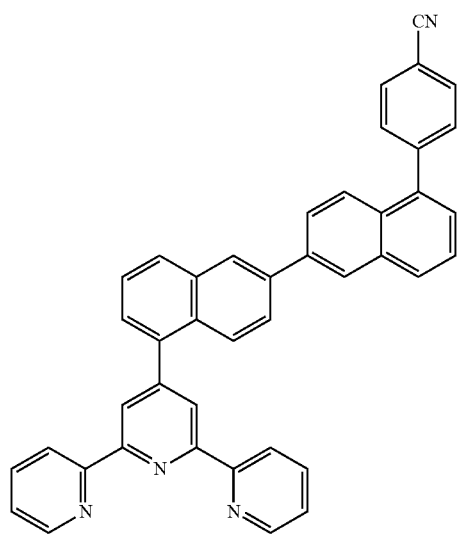
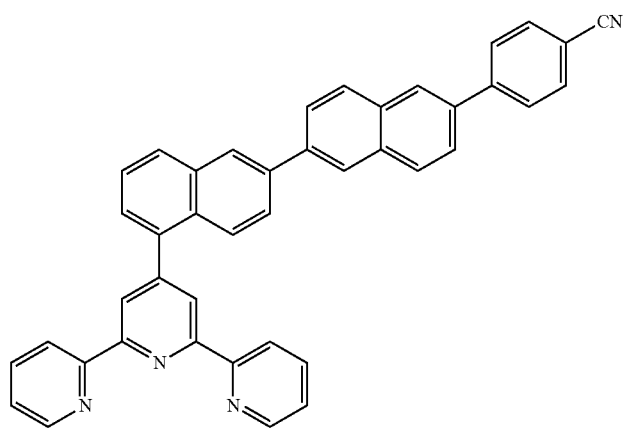
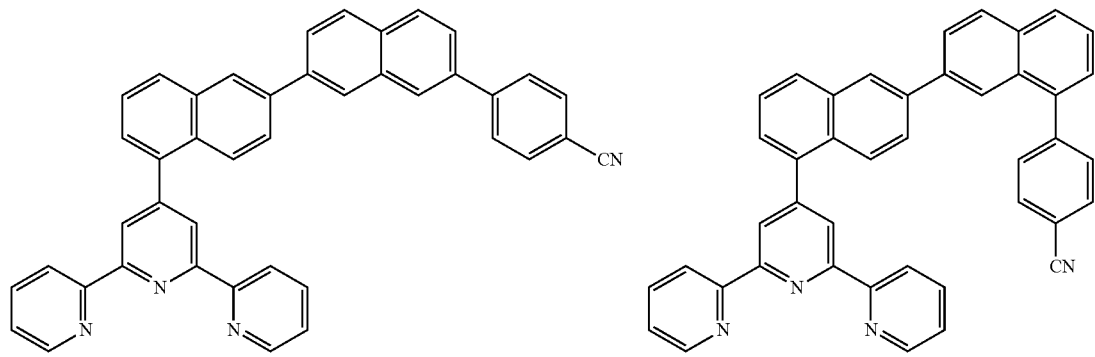
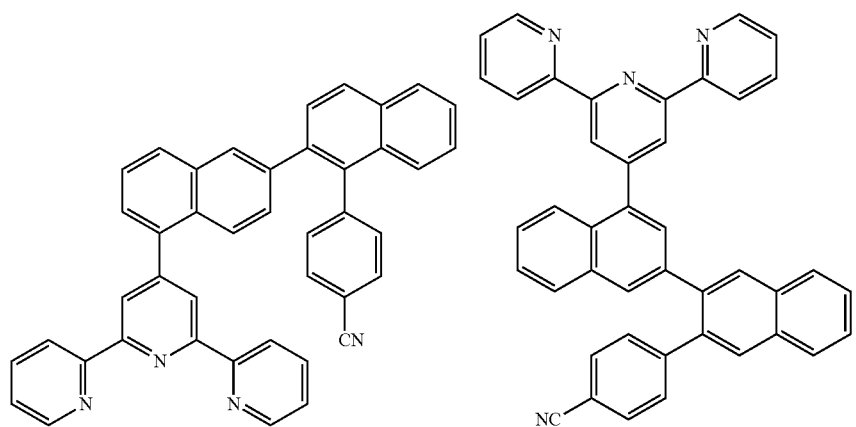

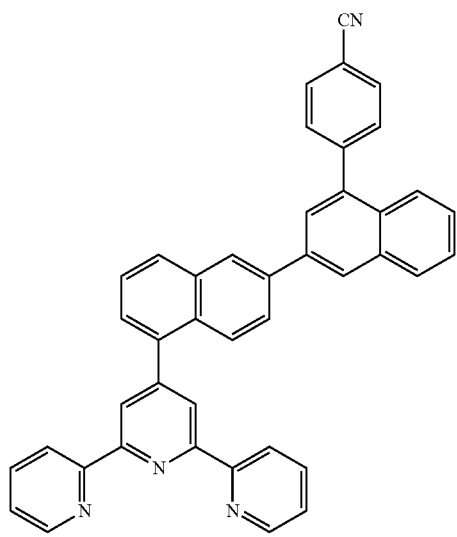
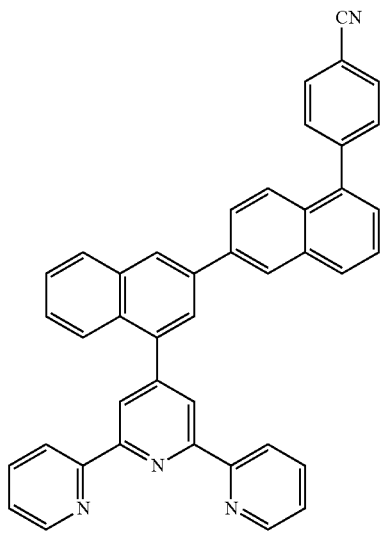
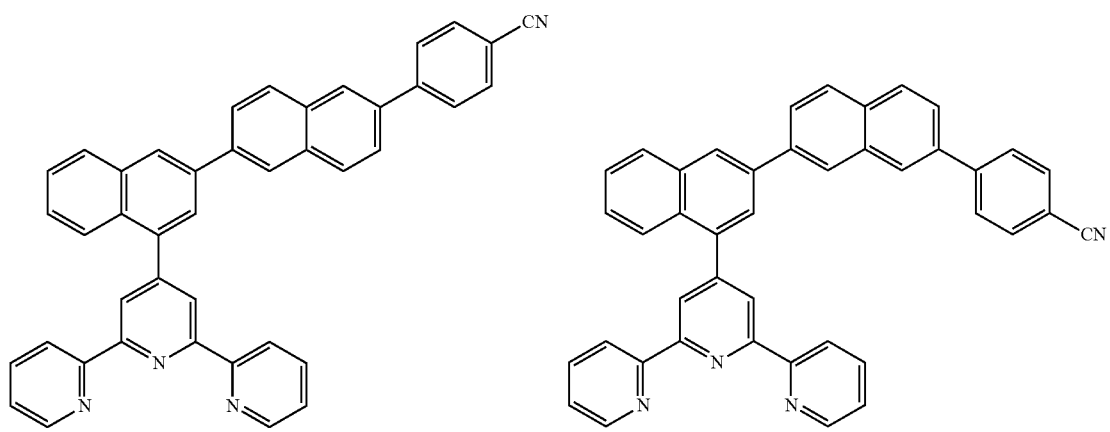
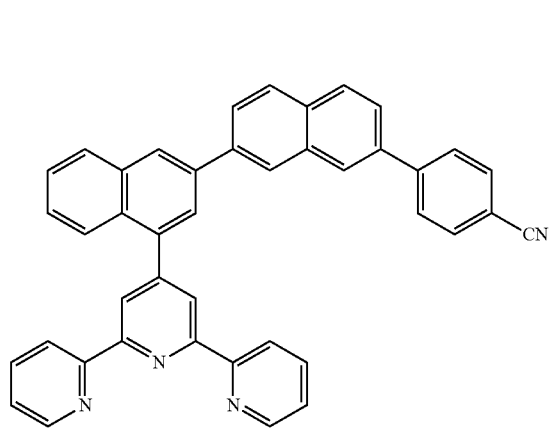
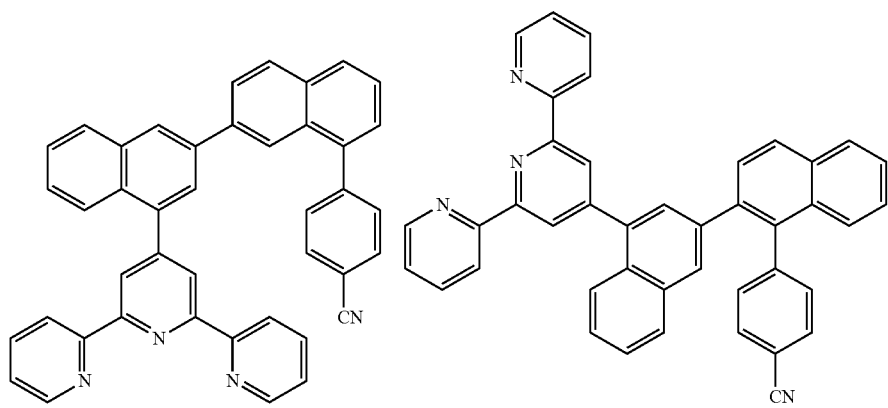

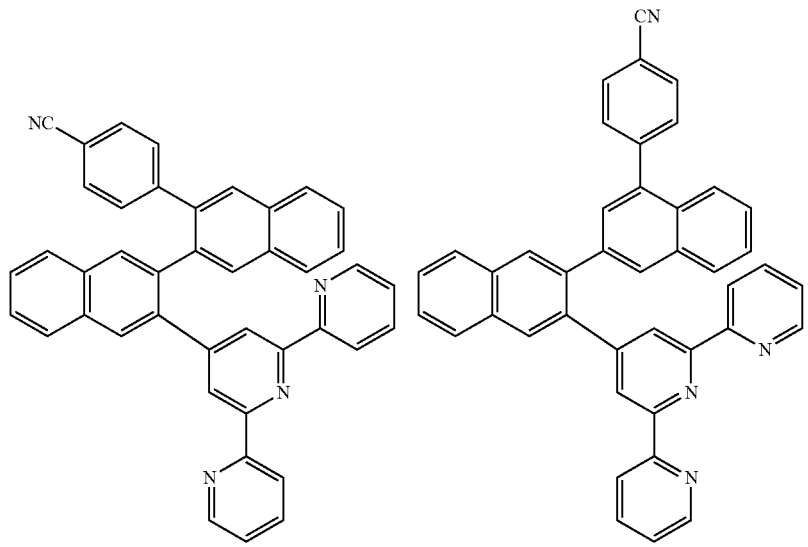
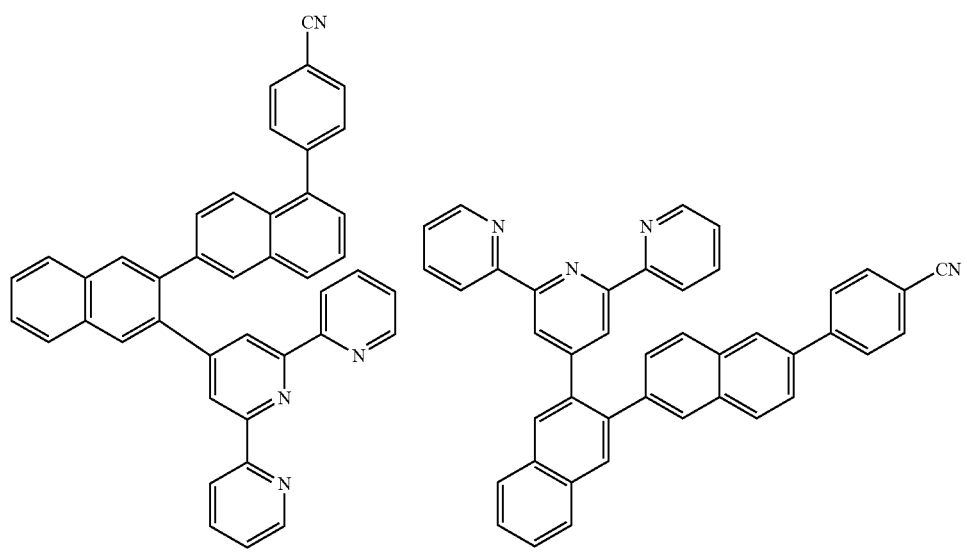
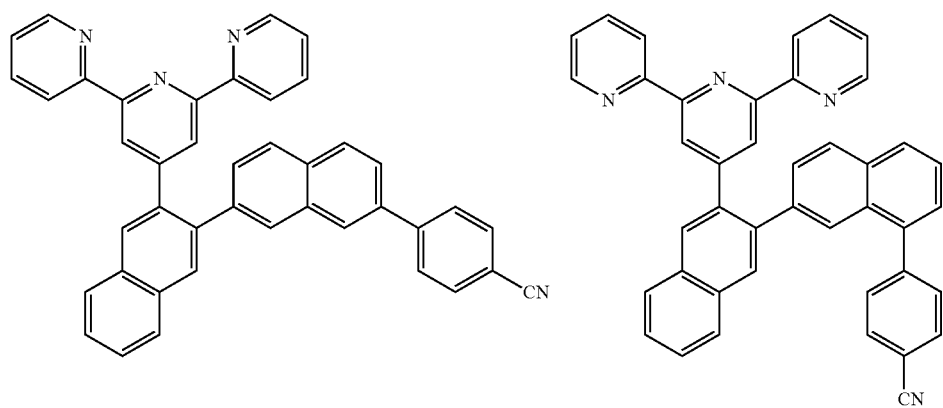

-continued
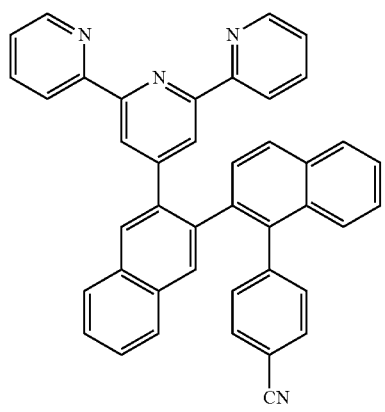
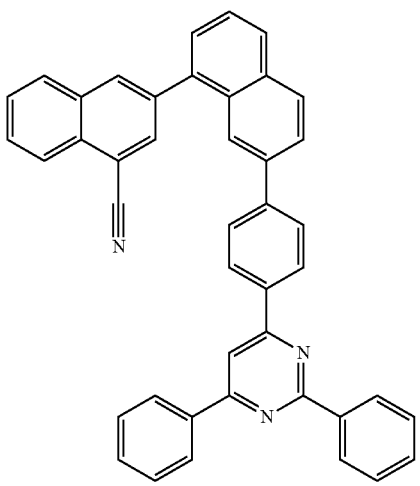
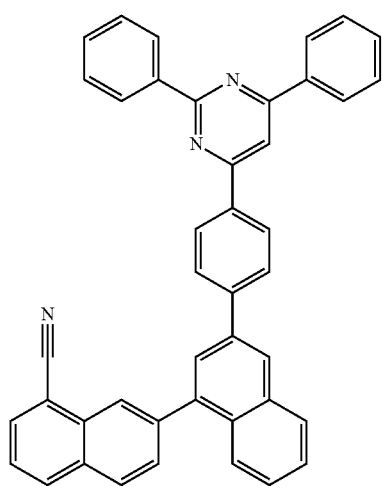
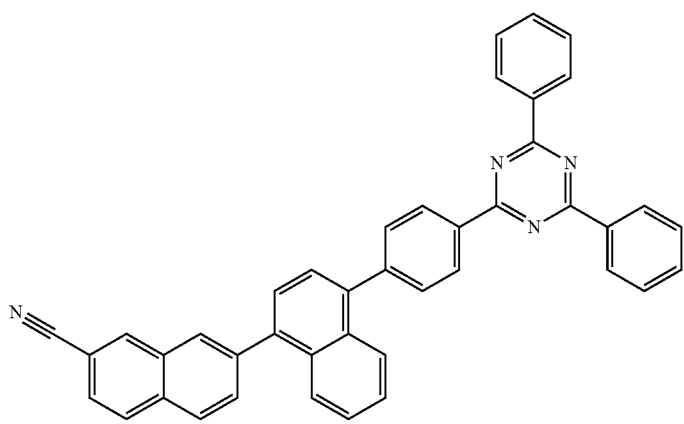
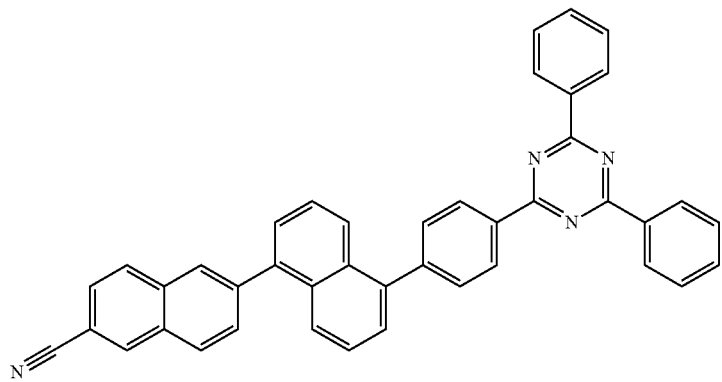

67
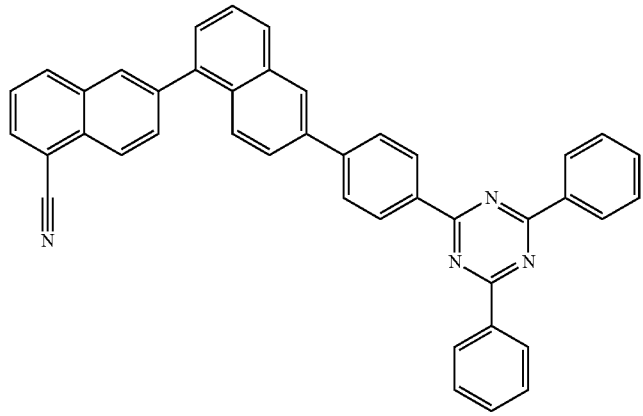
68
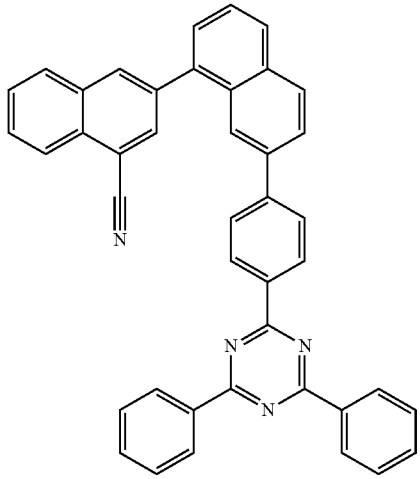
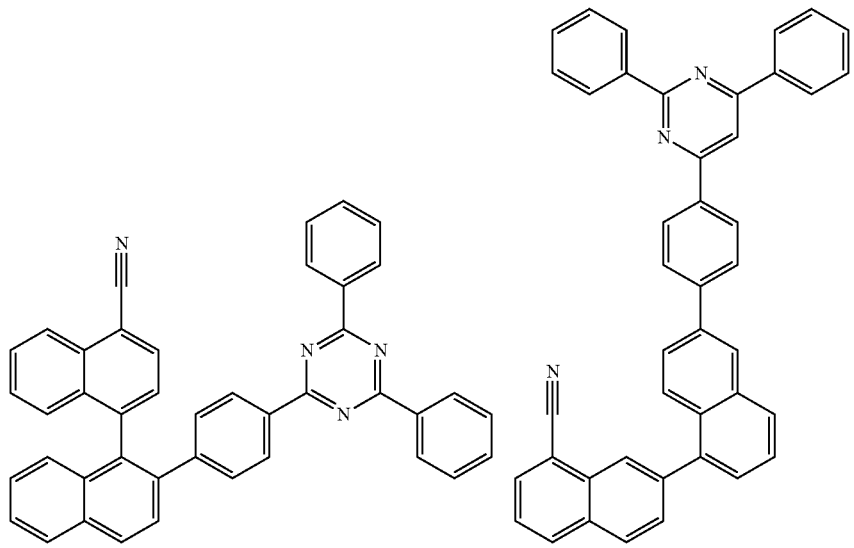
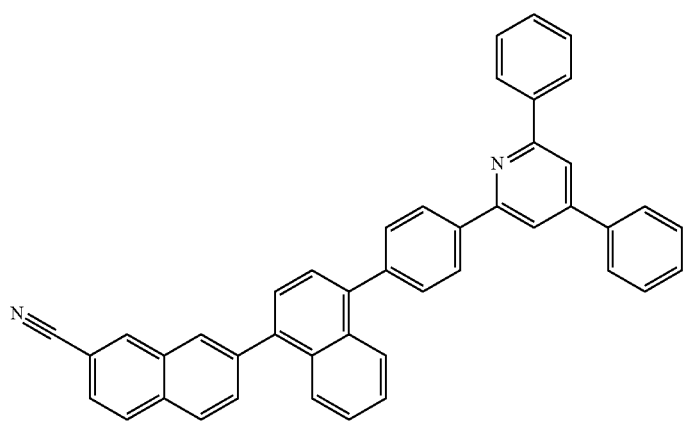

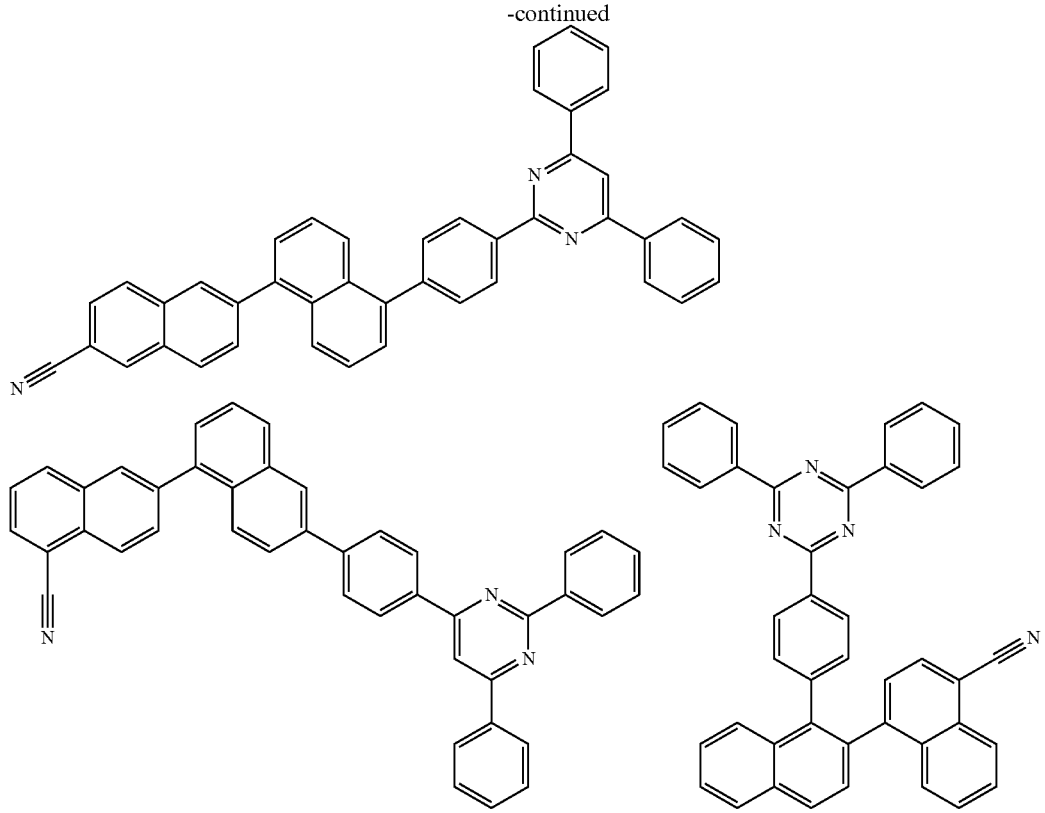
For example, among the compounds of Chemical Formula 1, the compound where Ar$_1$ is of Chemical Formula 2, L$_1$ is phenylene, and L$_2$ is a single bond, can be prepared by a method as shown in the following Reaction Scheme 1.
[Reaction Scheme 1]
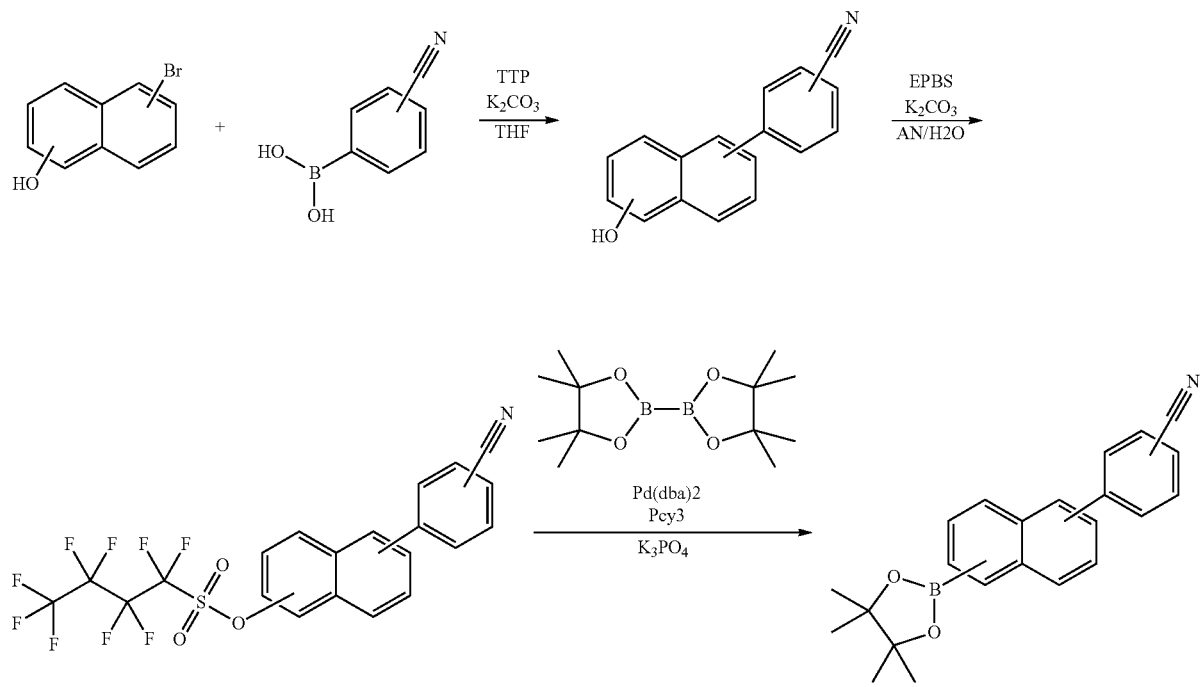

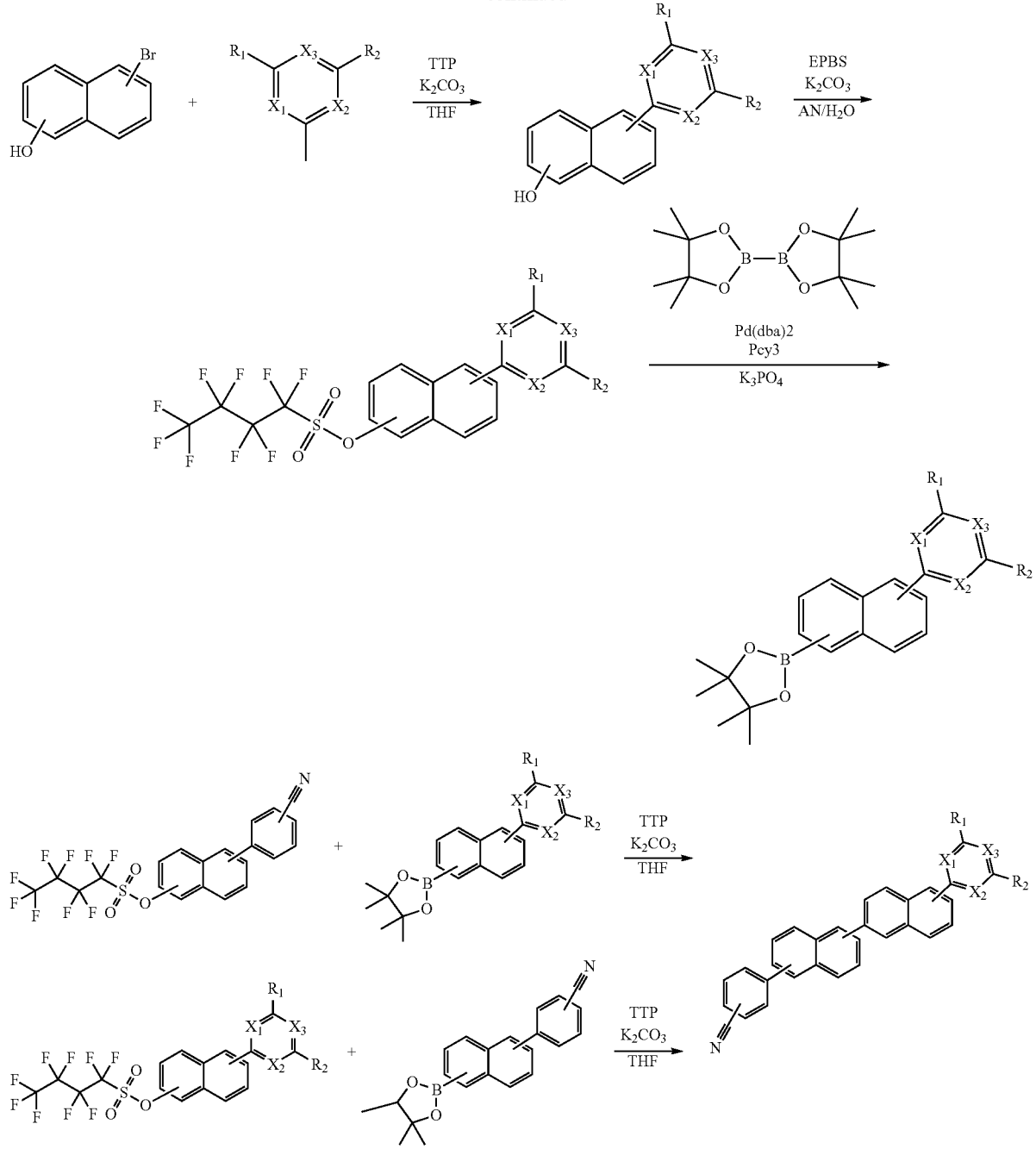

Of the compounds of Chemical Formula 1, the remaining compounds can also be prepared by a method identical with or similar to that shown in the Reaction Scheme 1 by applying reactants having different substituents. The above preparation method can be further specified in preparation examples to be described later.

In still another embodiment of the invention, an organic light emitting device including a compound of Chemical Formula 1 is provided. As an example, an organic light emitting device is provided, including: a first electrode; a second electrode provided opposite to the first electrode; and one or more organic material layers provided between the first electrode and the second electrode, wherein one or more layers of the organic material layers includes the compound of Chemical Formula 1.

The organic material layer of the organic light emitting device of the present invention can have a single layer structure, or it can have a multilayered structure in which two or more organic material layers are stacked. For example, the organic light emitting device of the present disclosure can have a structure including a hole injection layer, a hole transport layer, a light emitting layer, an electron transport layer, an electron injection layer, and the like as the organic material layer. However, the structure of the organic light emitting device is not limited thereto, and it can include a smaller number of organic layers.

Further, the organic material layer can include a hole injection layer, a hole transport layer, or a layer simultaneously performing hole injection and hole transport, wherein the hole injection layer, the hole transport layer, or the layer simultaneously performing hole injection and hole transport include a compound of Chemical Formula 1.

Further, the organic material layer can include a light emitting layer, wherein the light emitting layer includes a compound of Chemical Formula 1.

Further, the organic material layer can include an electron transport layer or an electron injection layer, wherein the electron transport layer or the electron injection layer includes a compound of Chemical Formula 1.

Further, the electron transport layer, the electron injection layer, or a layer simultaneously performing electron transport and electron injection include a compound of Chemical Formula 1.

Further, the organic material layer includes a light emitting layer and an electron transport layer, wherein the electron transport layer can include a compound of Chemical Formula 1.

Further, the organic light emitting device according to the present invention can be a normal type of organic light emitting device in which an anode, one or more organic material layers, and a cathode are sequentially stacked on a substrate. Further, the organic light emitting device according to the present disclosure can be an inverted type of organic light emitting device in which a cathode, one or more organic material layers, and an anode are sequentially stacked on a substrate. For example, the structure of an organic light emitting device according to an embodiment of the present disclosure is illustrated in FIGS. 1 and 2.

FIG. 1 shows an example of an organic light emitting device including a substrate 1, an anode 2, a light emitting layer 3, and a cathode 4. In such a structure, the compound of Chemical Formula 1 can be included in the light emitting layer.

FIG. 2 shows an example of an organic light emitting device including a substrate 1, an anode 2, a hole injection layer 5, a hole transport layer 6, a light emitting layer 7, an electron transport layer 8, and a cathode 4. In such a structure, the compound of Chemical Formula 1 can be included in one or more layers of the hole injection layer, the hole transport layer, the light emitting layer, and the electron transport layer.

The organic light emitting device according to the present invention can be manufactured by materials and methods known in the art, except that one or more layers of the organic material layers includes the compound of Chemical Formula 1. In addition, when the organic light emitting device includes a plurality of organic material layers, the organic material layers can be formed of the same material or different materials.

For example, the organic light emitting device according to the present invention can be manufactured by sequentially stacking a first electrode, an organic material layer, and a second electrode on a substrate. In this case, the organic light emitting device can be manufactured by depositing a metal, metal oxides having conductivity, or an alloy thereof on the substrate using a PVD (physical vapor deposition) method such as a sputtering method or an e-beam evaporation method to form an anode, forming organic material layers including the hole injection layer, the hole transport layer, the light emitting layer, and the electron transport layer thereon, and then depositing a material that can be used as the cathode thereon. In addition to such a method, the organic light emitting device can be manufactured by sequentially depositing a cathode material, an organic material layer, and an anode material on a substrate.

In addition, the compound of Chemical Formula 1 can be formed into an organic layer by a solution coating method as well as a vacuum deposition method at the time of manufacturing an organic light emitting device. Herein, the solution coating method means spin coating, dip coating, doctor blading, inkjet printing, screen printing, a spray method, roll coating, or the like, but is not limited thereto.

In addition to such a method, the organic light emitting device can be manufactured by sequentially depositing a cathode material, an organic material layer, and an anode material on a substrate (International Publication WO2003/012890). However, the manufacturing method is not limited thereto.

As an example, the first electrode is an anode (positive electrode) and the second electrode is a cathode (negative electrode), or alternatively the first electrode is a cathode and the second electrode is an anode.

As the anode (positive electrode) material, generally, a material having a large work function is preferably used so that holes can be smoothly injected into the organic material layer. Specific examples of the anode material include metals such as vanadium, chrome, copper, zinc, and gold, or alloys thereof; metal oxides such as zinc oxides, indium oxides, indium tin oxides (ITO), and indium zinc oxides (IZO); a combination of metals and oxides, such as ZnO:Al or $SnO_2$:Sb; conductive polymers such as poly(3-methyl-thiophene), poly[3,4-(ethylene-1,2-dioxy)thiophene] (PEDOT), polypyrrole, polyaniline, and the like, but are not limited thereto.

As the cathode (negative electrode) material, generally, a material having a small work function is preferably used so that electrons can be easily injected into the organic material layer. Specific examples of the cathode material include metals such as magnesium, calcium, sodium, potassium, titanium, indium, yttrium, lithium, gadolinium, aluminum, silver, tin, and lead, or alloys thereof; a multilayered structure material such as LiF/Al or $LiO_2$/Al; and the like, but are not limited thereto.

The hole injection layer is a layer for injecting holes from the electrode, and the hole injection material is preferably a compound which has a capability of transporting the holes, thus has a hole injecting effect in the anode and an excellent hole injecting effect to the light emitting layer or the light emitting material, prevents excitons produced in the light emitting layer from moving to an electron injection layer or the electron injection material, and is excellent in the ability to form a thin film. It is preferable that a HOMO (highest occupied molecular orbital) of the hole injection material is between the work function of the anode material and a HOMO of a peripheral organic material layer. Specific examples of the hole injection material include metal porphyrin, oligothiophene, an arylamine-based organic material, a hexanitrilehexaazatriphenylene-based organic material, a quinacridone-based organic material, a perylene-based organic material, anthraquinone, polyaniline, a polythiophene-based conductive polymer, and the like, but are not limited thereto.

The hole transport layer is a layer that receives holes from a hole injection layer and transports the holes to the light emitting layer, and is suitably a material having large mobility to the holes, and which can receive holes from the anode or the hole injection layer and transfer the holes to the light emitting layer. Specific examples thereof include an arylamine-based organic material, a conductive polymer, a block copolymer in which a conjugate portion and a non-conjugate portion are present together, and the like, but are not limited thereto.

The light emitting material is preferably a material which can receive holes and electrons transported from a hole transport layer and an electron transport layer, respectively, and combine the holes and the electrons to emit light in a visible ray region, and has good quantum efficiency to fluorescence or phosphorescence. Specific examples of the light emitting material include an 8-hydroxy-quinoline aluminum complex ($Alq_3$); a carbazole-based compound; a dimerized styryl compound; BAlq; a 10-hydroxybenzoquinoline-metal compound; a benzoxazole, benzothiazole, and benzimidazole-based compound; a poly(p-phenylene vinylene) (PPV)-based polymer; a Spiro compound; polyfluorene, rubrene, and the like, but are not limited thereto.

The light emitting layer can include a host material and a dopant material. The host material can be a fused aromatic ring derivative, a heterocycle-containing compound, or the like. Specific examples of the fused aromatic ring derivatives include anthracene derivatives, pyrene derivatives, naphthalene derivatives, pentacene derivatives, phenanthrene compounds, fluoranthene compounds, and the like. Examples of the heterocyclic-containing compounds include carbazole derivatives, dibenzofuran derivatives, ladder-type furan compounds, pyrimidine derivatives, and the like, but are not limited thereto.

Examples of the dopant material include an aromatic amine derivative, a styrylamine compound, a boron complex, a fluoranthene compound, a metal complex, and the like. Specifically, the aromatic amine derivative is a substituted or unsubstituted fused aromatic ring derivative having an arylamino group, and examples thereof include pyrene, anthracene, chrysene, periflanthene, and the like, which have an arylamino group. The styrylamine compound is a compound where at least one arylvinyl group is substituted in a substituted or unsubstituted arylamine, in which one or more substituent groups selected from the group consisting of an aryl group, a silyl group, an alkyl group, a cycloalkyl group, and an arylamino group are substituted or unsubstituted. Specific examples thereof include styrylamine, styryldiamine, styryltriamine, styryltetramine, and the like, but are not limited thereto. Further, the metal complex includes an iridium complex, a platinum complex, and the like, but is not limited thereto.

The electron transport layer is a layer which receives electrons from an electron injection layer and transports the electrons to a light emitting layer, and an electron transport material is suitably a material which can receive electrons well from a cathode and transfer the electrons to a light emitting layer, and has large mobility for electrons. Specific examples of the electron transport material include: an Al complex of 8-hydroxyquinoline; a complex including $Alq_3$; an organic radical compound; a hydroxyflavone-metal complex; and the like, but are not limited thereto. The electron transport layer can be used with any desired cathode material, as used according to the related art. In particular, appropriate examples of the cathode material are a typical material which has a low work function, followed by an aluminum layer or a silver layer. Specific examples thereof include cesium, barium, calcium, ytterbium, and samarium, in each case followed by an aluminum layer or a silver layer.

The electron injection layer is a layer which injects electrons from an electrode, and is preferably a compound which has a capability of transporting electrons, has an effect of injecting electrons from a cathode and an excellent effect of injecting electrons into a light emitting layer or a light emitting material, prevents excitons produced from the light emitting layer from moving to a hole injection layer, and is also excellent in the ability to form a thin film. Specific examples of the electron injection layer include fluorenone, anthraquinodimethane, diphenoquinone, thiopyran dioxide, oxazole, oxadiazole, triazole, imidazole, perylenetetracarboxylic acid, fluorenylidene methane, anthrone, and the like, and derivatives thereof, a metal complex compound, a nitrogen-containing 5-membered ring derivative, and the like, but are not limited thereto.

Examples of the metal complex compound include 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato)gallium, bis(10-hydroxy-benzo[h]quinolinato)beryllium, bis(10-hydroxybenzo[h]quinolinato)zinc, bis(2-methyl-8-quinolinato)chlorogallium, bis(2-methyl-8-quinolinato)(o-cresolato)gallium, bis(2-methyl-8-quinolinato)(1-naphtholato)aluminum, bis(2-methyl-8-quinolinato)-(2-naphtholato)gallium, and the like, but are not limited thereto.

The organic light emitting device according to the present invention can be a front side emission type, a back side emission type, or a double side emission type according to the used material.

In addition, the compound of Chemical Formula 1 can be included in an organic solar cell or an organic transistor in addition to an organic light emitting device.

The preparation of the compound of Chemical Formula 1 and the organic light emitting device including the same will be described in detail in the following examples. However, these examples are presented for illustrative purposes only, and are not intended to limit the scope of the present invention.

Preparation Example 1

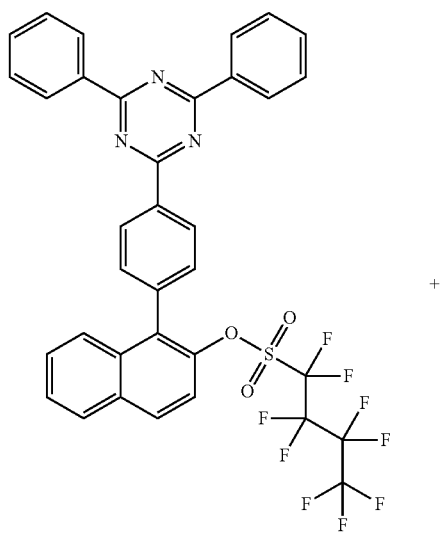

[A]

-continued

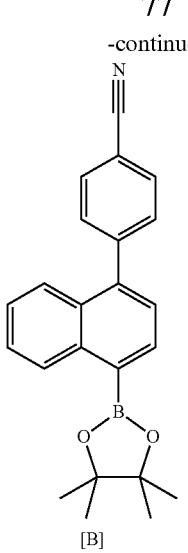

[B]

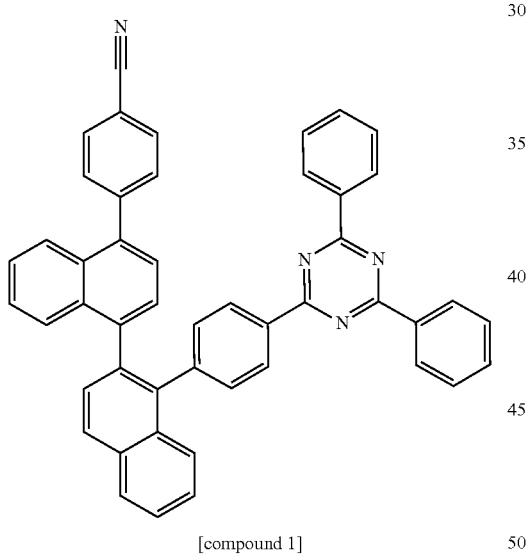

[compound 1]

Compound A (20.00 g, 27.26 mmol) and Compound B (9.68 g, 27.26 mmol) were completely dissolved in 300 mL of tetrahydrofuran in a 500-ml round bottom flask under a nitrogen atmosphere, to which a 2 M aqueous potassium carbonate solution (150 ml) was added and tetrakis-(triphenylphosphine)palladium (0.94 g, 0.82 mmol) was added, and then the resulting mixture was heated and stirred for 3 hours. The temperature was lowered to normal temperature (23±5° C.), the aqueous layer was removed, and the resulting product was dried over anhydrous magnesium sulfate, and then concentrated under reduced pressure and recrystallized with 180 mL of ethyl acetate to prepare Compound 1 (11.9 g, yield: 66%).

MS: [M+H]$^+$=622

Preparation Example 2

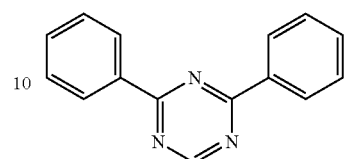

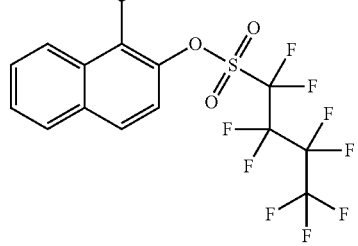

[A]

+

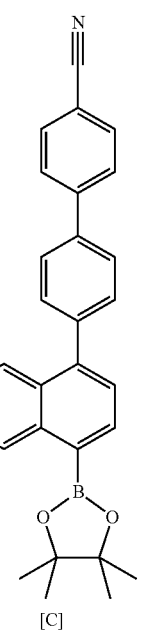

[C]

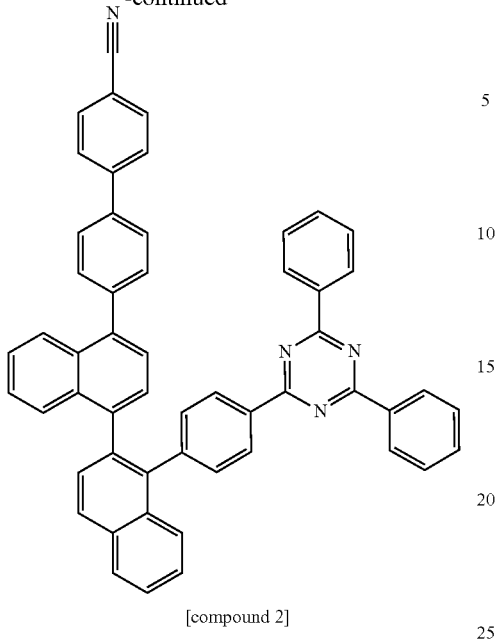

[compound 2]

Compound A (20.00 g, 27.26 mmol) and Compound C (11.79 g, 27.26 mmol) were completely dissolved in 300 mL of tetrahydrofuran in a 500-ml round bottom flask under a nitrogen atmosphere, to which a 2 M aqueous potassium carbonate solution (150 ml) was added and tetrakis-(triphenylphosphine)palladium (0.94 g, 0.82 mmol) was added, and then the resulting mixture was heated and stirred for 3 hours. The temperature was lowered to normal temperature (23±5° C.), the aqueous layer was removed, and the resulting product was dried over anhydrous magnesium sulfate, and then concentrated under reduced pressure and recrystallized with 180 mL of ethyl acetate to prepare Compound 2 (12.2 g, yield: 64%).

MS: [M+H]$^+$=738

Preparation Example 3

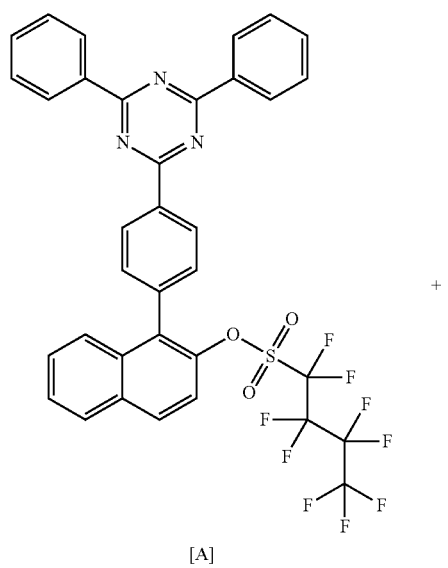

[A]

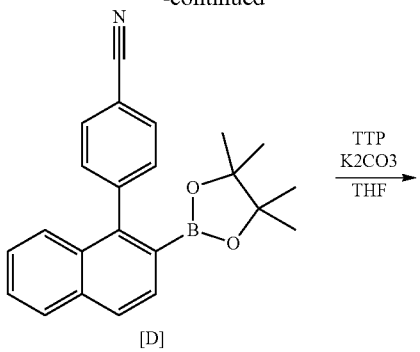

[D]

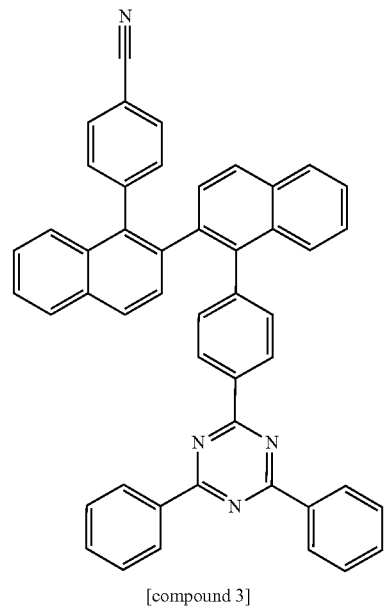

[compound 3]

Compound A (20.00 g, 27.26 mmol) and Compound D (9.68 g, 27.26 mmol) were completely dissolved in 300 mL of tetrahydrofuran in a 500-ml round bottom flask under a nitrogen atmosphere, to which a 2 M aqueous potassium carbonate solution (150 ml) was added and tetrakis-(triphenylphosphine)palladium (0.94 g, 0.82 mmol) was added, and then the resulting mixture was heated and stirred for 3 hours. The temperature was lowered to normal temperature (23±5° C.), the aqueous layer was removed, and the resulting product was dried over anhydrous magnesium sulfate, and then concentrated under reduced pressure and recrystallized with 180 mL of ethyl acetate to prepare Compound 3 (10.9 g, yield: 60%).

MS: [M+H]$^+$=622

Preparation Example 4

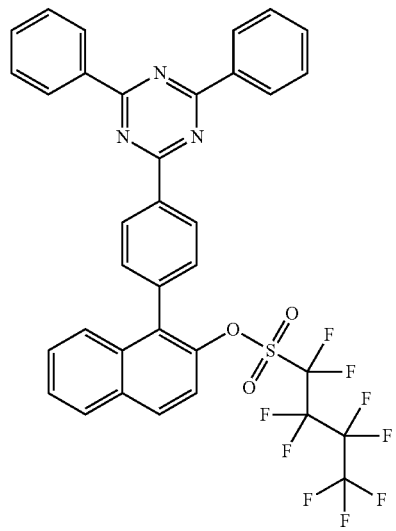

[A]

+

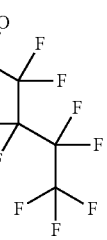

[E]

→ TTP K2CO3 / THF

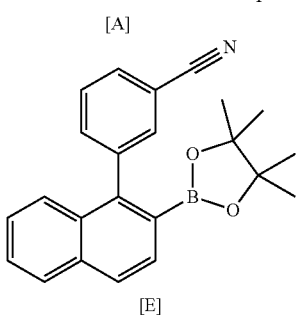

[compound 4]

Compound A (20.00 g, 27.26 mmol) and Compound E (9.68 g, 27.26 mmol) were completely dissolved in 300 mL of tetrahydrofuran in a 500-ml round bottom flask under a nitrogen atmosphere, to which a 2 M aqueous potassium carbonate solution (150 ml) was added and tetrakis-(triphenylphosphine)palladium (0.94 g, 0.82 mmol) was added, and then the resulting mixture was heated and stirred for 3 hours. The temperature was lowered to normal temperature (23±5° C.), the aqueous layer was removed, and the resulting product was dried over anhydrous magnesium sulfate, and then concentrated under reduced pressure and recrystallized with 180 mL of ethyl acetate to prepare Compound 4 (12.1 g, yield: 67%).

MS: [M+H]⁺=622

Preparation Example 5

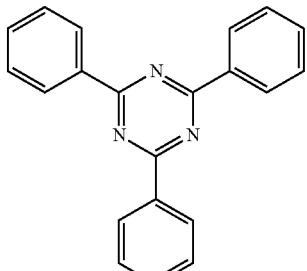

+

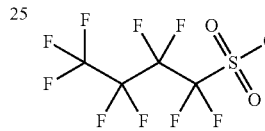

[F]

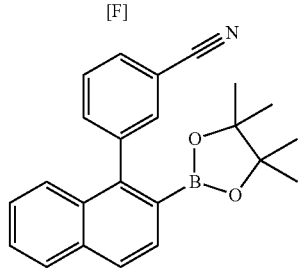

[E]

→ TTP K2CO3 / THF

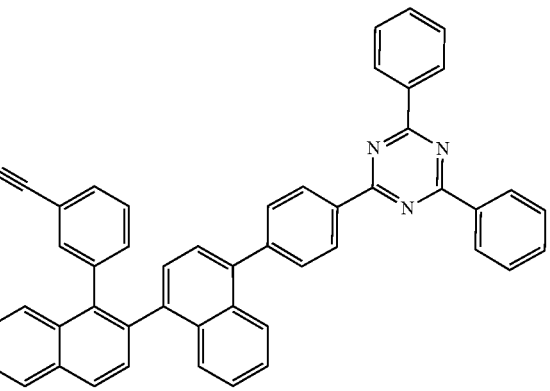

[compound 5]

Compound F (20.00 g, 27.26 mmol) and Compound E (9.68 g, 27.26 mmol) were completely dissolved in 300 mL of tetrahydrofuran in a 500-ml round bottom flask under a nitrogen atmosphere, to which a 2 M aqueous potassium carbonate solution (150 ml) was added and tetrakis-(triphenylphosphine)palladium (0.94 g, 0.82 mmol) was added, and then the resulting mixture was heated and stirred for 3 hours. The temperature was lowered to normal temperature (23±5° C.), the aqueous layer was removed, and the resulting product was dried over anhydrous magnesium sulfate, and then concentrated under reduced pressure and recrystallized with 180 mL of ethyl acetate to prepare Compound 5 (9.8 g, yield: 54%).
MS: $[M+H]^+=622$ Preparation Example 6

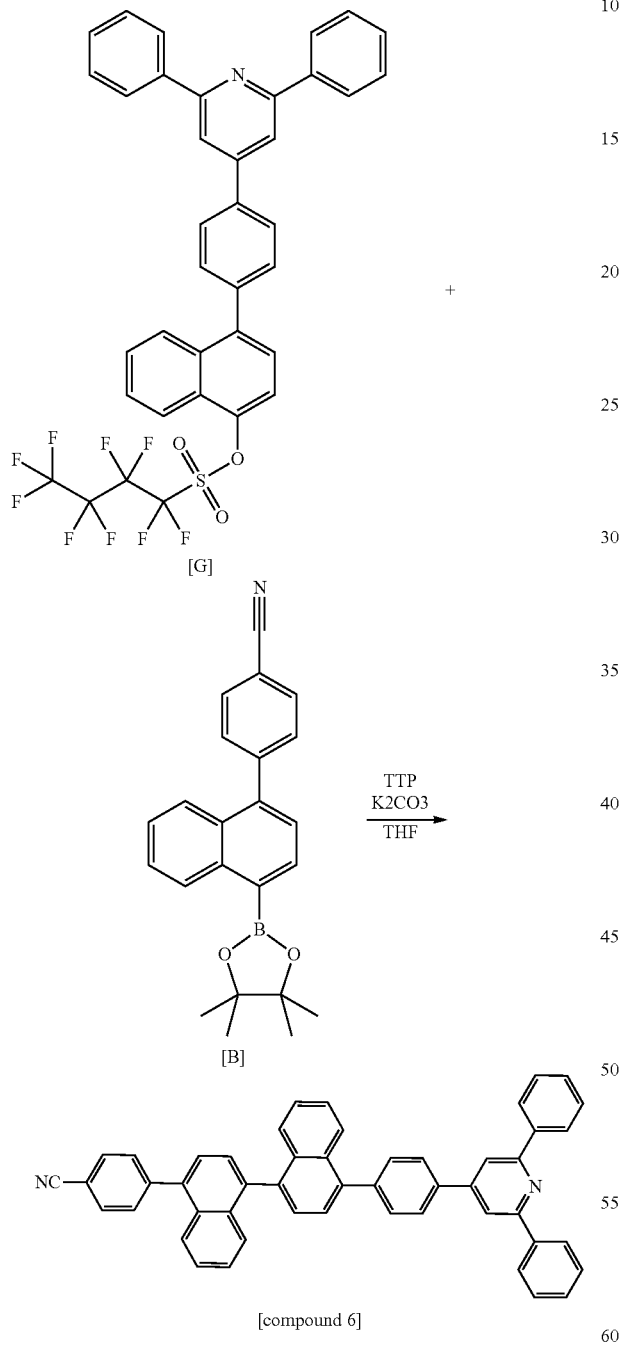

[compound 6]

Compound G (20.00 g, 27.35 mmol) and Compound B (9.71 g, 27.35 mmol) were completely dissolved in 300 mL of tetrahydrofuran in a 500-ml round bottom flask under a nitrogen atmosphere, to which a 2 M aqueous potassium carbonate solution (150 ml) was added and tetrakis-(triphenylphosphine)palladium (0.94 g, 0.82 mmol) was added, and then the resulting mixture was heated and stirred for 3 hours. The temperature was lowered to normal temperature (23±5° C.), the aqueous layer was removed, and the resulting product was dried over anhydrous magnesium sulfate, and then concentrated under reduced pressure and recrystallized with 180 mL of ethyl acetate to prepare Compound 6 (11.5 g, yield: 63%).
MS: $[M+H]^+=620$ Preparation Example 7

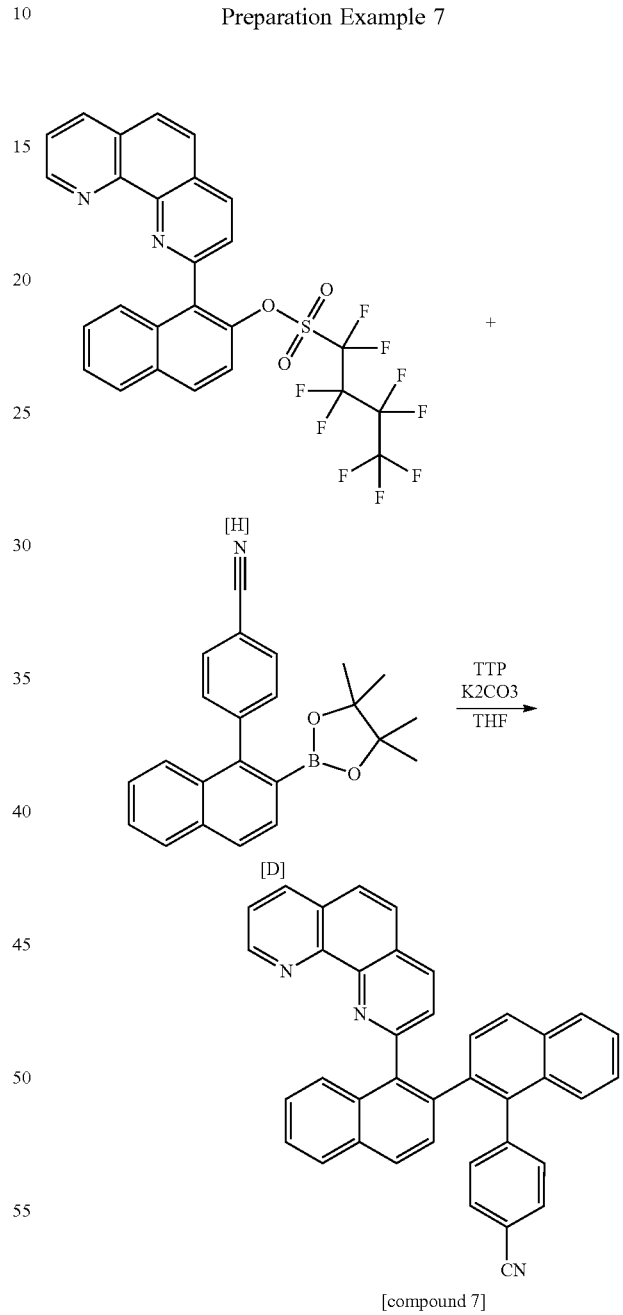

[compound 7]

Compound H (20.00 g, 33.11 mmol) and Compound D (11.75 g, 33.11 mmol) were completely dissolved in 300 mL of tetrahydrofuran in a 500-ml round bottom flask under a nitrogen atmosphere, to which a 2 M aqueous potassium carbonate solution (150 ml) was added and tetrakis-(triphenylphosphine)palladium (1.14 g, 0.99 mmol) was added, and then the resulting mixture was heated and stirred for 3

85 hours. The temperature was lowered to normal temperature (23±5° C.), the aqueous layer was removed, and the resulting product was dried over anhydrous magnesium sulfate, and then concentrated under reduced pressure and recrystallized with 180 mL of ethyl acetate to prepare Compound 7 (10.2 g, yield: 58%).

MS: [M+H]$^+$=533

Preparation Example 8

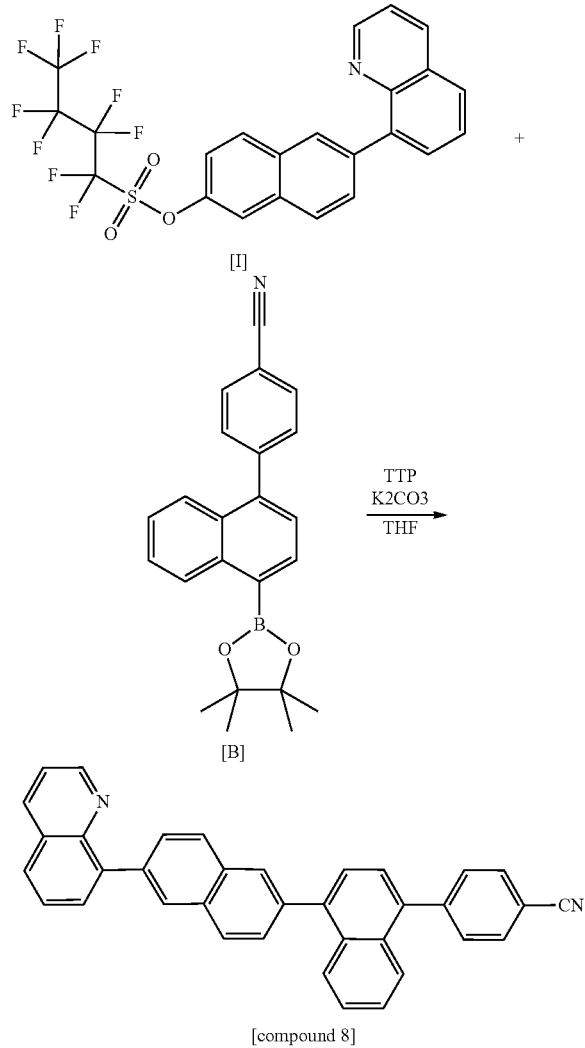

[compound 8]

Compound I (20.00 g, 37.52 mmol) and Compound B (13.32 g, 37.52 mmol) were completely dissolved in 300 mL of tetrahydrofuran in a 500-ml round bottom flask under a nitrogen atmosphere, to which a 2 M aqueous potassium carbonate solution (150 ml) was added and tetrakis-(triphenylphosphine)palladium (1.30 g, 1.12 mmol) was added, and then the resulting mixture was heated and stirred for 3 hours. The temperature was lowered to normal temperature (23±5° C.), the aqueous layer was removed, and the resulting product was dried over anhydrous magnesium sulfate, and then concentrated under reduced pressure and recrystallized with 180 mL of ethyl acetate to prepare Compound 8 (10.4 g, yield: 56%).

MS: [M+H]$^+$=482

86

Preparation Example 9

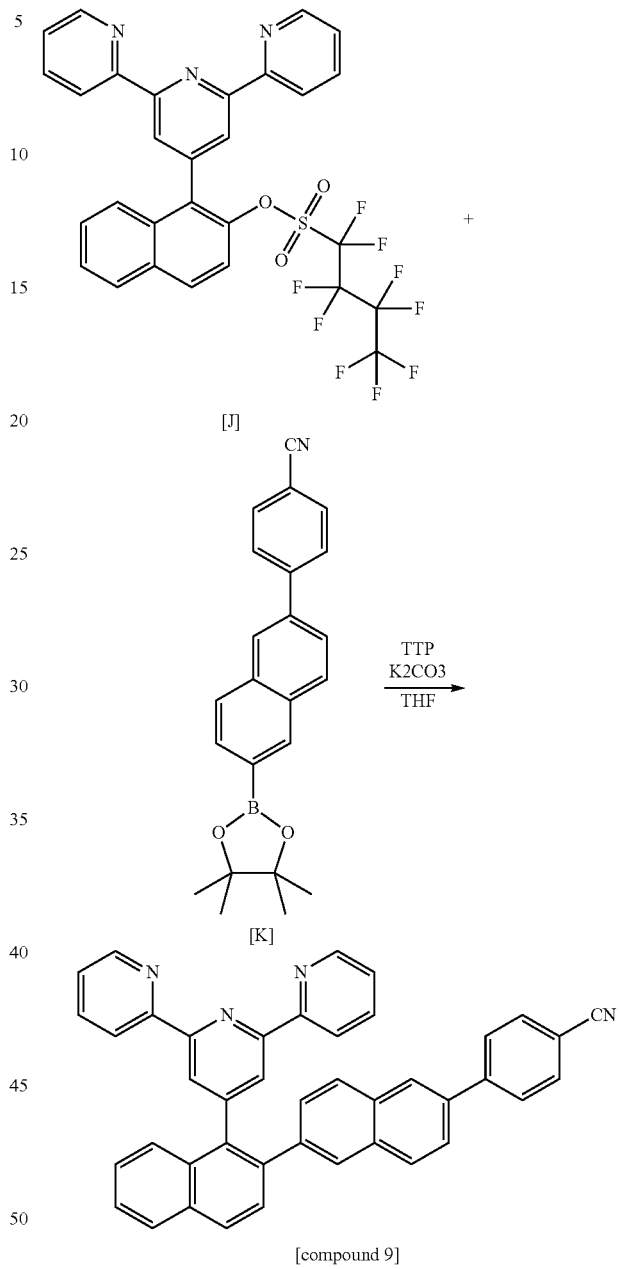

[compound 9]

Compound J (20.00 g, 30.44 mmol) and Compound K (10.80 g, 30.44 mmol) were completely dissolved in 300 mL of tetrahydrofuran in a 500-ml round bottom flask under a nitrogen atmosphere, to which a 2 M aqueous potassium carbonate solution (150 ml) was added and tetrakis-(triphenylphosphine)palladium (1.05 g, 0.91 mmol) was added, and then the resulting mixture was heated and stirred for 3 hours. The temperature was lowered to normal temperature (23±5° C.), the aqueous layer was removed, and the resulting product was dried over anhydrous magnesium sulfate, and then concentrated under reduced pressure and recrystallized with 180 mL of ethyl acetate to prepare Compound 9 (11.2 g, yield: 63%).

MS: [M+H]$^+$=586

Preparation Example 10

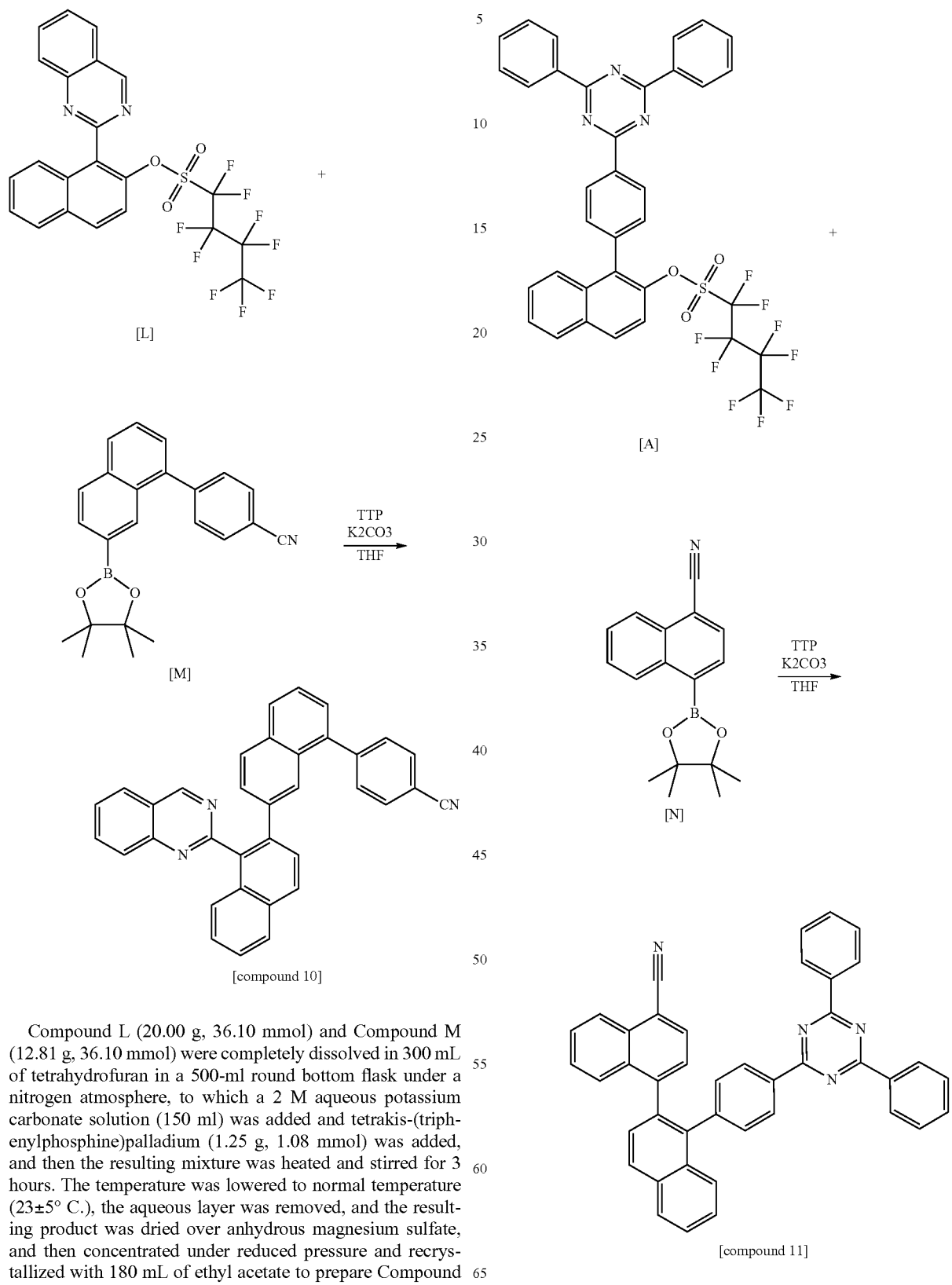

Compound L (20.00 g, 36.10 mmol) and Compound M (12.81 g, 36.10 mmol) were completely dissolved in 300 mL of tetrahydrofuran in a 500-ml round bottom flask under a nitrogen atmosphere, to which a 2 M aqueous potassium carbonate solution (150 ml) was added and tetrakis-(triphenylphosphine)palladium (1.25 g, 1.08 mmol) was added, and then the resulting mixture was heated and stirred for 3 hours. The temperature was lowered to normal temperature (23±5° C.), the aqueous layer was removed, and the resulting product was dried over anhydrous magnesium sulfate, and then concentrated under reduced pressure and recrystallized with 180 mL of ethyl acetate to prepare Compound 10 (9.8 g, yield: 56%).

MS: [M+H]⁺=483

Preparation Example 11

Compound A (20.00 g, 27.26 mmol) and Compound N (7.61 g, 27.26 mmol) were completely dissolved in 300 mL of tetrahydrofuran in a 500-ml round bottom flask under a nitrogen atmosphere, to which a 2 M aqueous potassium carbonate solution (150 ml) was added and tetrakis-(triphenylphosphine)palladium (0.94 g, 0.82 mmol) was added, and then the resulting mixture was heated and stirred for 3 hours. The temperature was lowered to normal temperature (23±5° C.), the aqueous layer was removed, and the resulting product was dried over anhydrous magnesium sulfate, and then concentrated under reduced pressure and recrystallized with 180 mL of ethyl acetate to prepare Compound 11 (10.1 g, yield: 63%).

MS: $[M+H]^+$=586

Example 1-1

A glass substrate on which ITO (indium tin oxide) was coated as a thin film to a thickness of 1000 Å was put into distilled water in which a detergent was dissolved, and ultrasonically cleaned. In this case, a product manufactured by Fischer Co., was used as the detergent, and as the distilled water, distilled water filtered twice using a filter manufactured by Millipore Co., was used. After the ITO was cleaned for 30 minutes, ultrasonic cleaning was repeated twice using distilled water for 10 minutes. After the cleaning with distilled water was completed, the substrate was ultrasonically cleaned with solvents of isopropyl alcohol, acetone, and methanol, then dried, and then transferred to a plasma cleaner. In addition, the substrate was cleaned for 5 minutes using oxygen plasma, and then transferred to a vacuum depositor.

On the ITO transparent electrode thus prepared, the following compound [HI-A] was thermally vacuum deposited to have a thickness of 600 Å, thereby forming a hole injection layer. The following compound [HAT] (50 Å) and the following compound [HT-A] (600 Å) were sequentially vacuum deposited on the hole injection layer to form a hole transfer layer. Then, the following compounds [BH] and [BD] were vacuum deposited at a weight ratio of 25:1 on the hole transport layer to a thickness of 200 Å to form a light emitting layer. The compound 1 prepared in Preparation Example 1 and the following compound [LiQ] (lithium quinolate) were vacuum deposited at a weight ratio of 1:1 on the light emitting layer to form an electron injection and transport layer with a thickness of 350 Å. Lithium fluoride (LiF) and aluminum were sequentially deposited to have a thickness of 10 Å and 1000 Å, respectively, on the electron injection and transport layer, thereby forming a cathode.

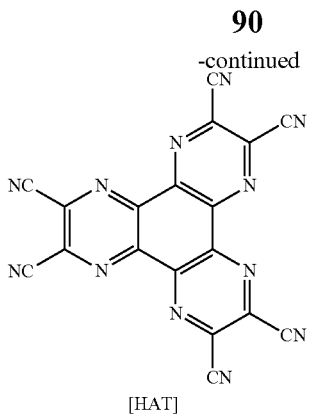

[HAT]

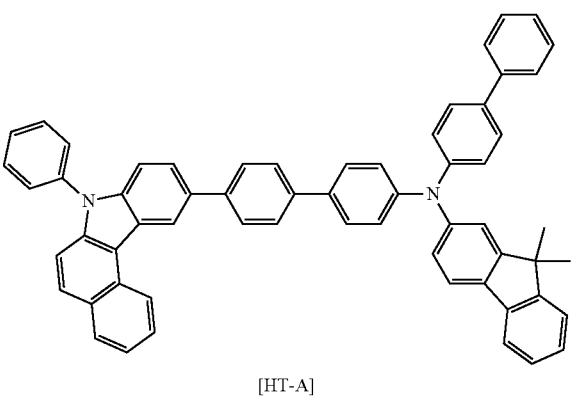

[HT-A]

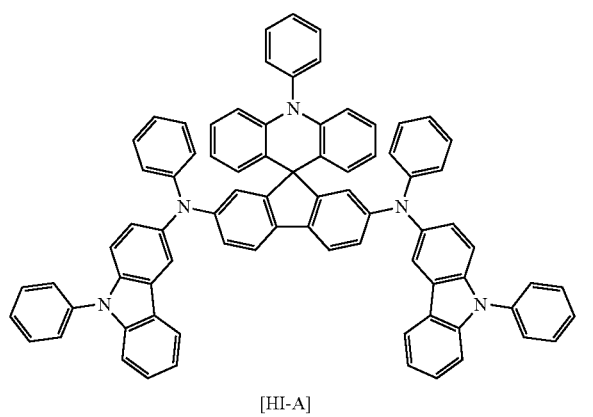

[HI-A]

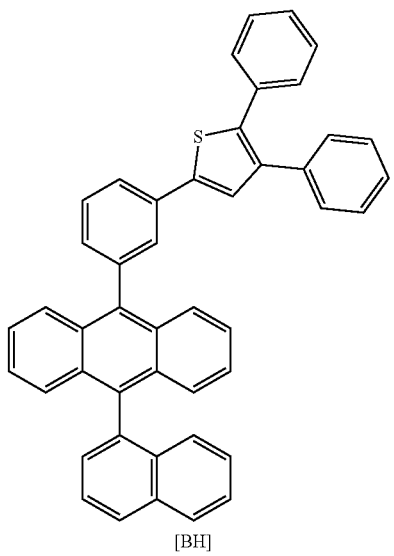

[BH]

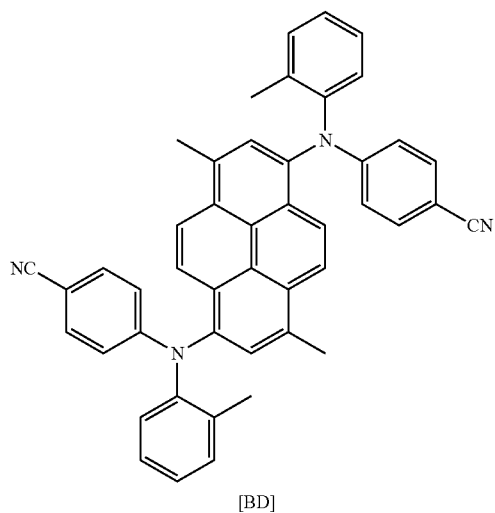

[BD]

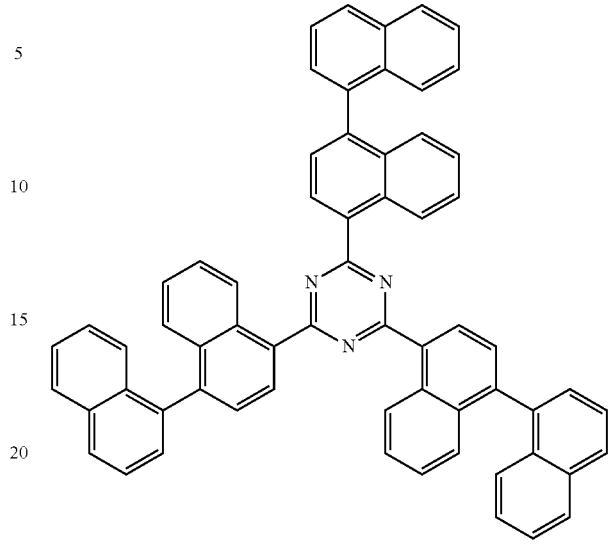

(I)

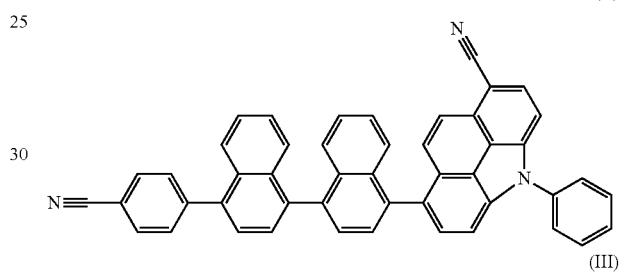

(II)

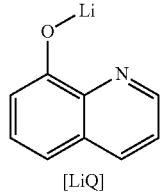

[LiQ]

In the above-mentioned process, the vapor deposition rate of the organic material was maintained at 0.4 to 0.9 Å/second, the deposition rate of lithium fluoride of the cathode was maintained at 0.3 Å/second, the deposition rate of aluminum was maintained at 2 Å/second, and the degree of vacuum during the deposition was maintained at $1 \times 10^{-7}$ to $5 \times 10^{-8}$ Torr, thereby manufacturing an organic light emitting device.

Examples 1-2 to 1-11

An organic light emitting device was manufactured in the same manner as in Example 1-1, except that one compound of the compounds 2 to 11 shown in Table 1 below was used instead of Compound 1 in Example 1-1.

Comparative Examples 1-1 to 1-3

An organic light emitting device was manufactured in the same manner as in Example 1-1, except that the compound (I), (II), or (III) having the following structures as shown in Table 1 below was used instead of Compound 1 in Example 1-1.

Comparative Examples 1-4

An organic light emitting device was manufactured in the same manner as in Example 1-1, except that the compound (IV) having the following structure as shown in Table 1 below was used instead of Compound 1 in Example 1-1.

(IV)

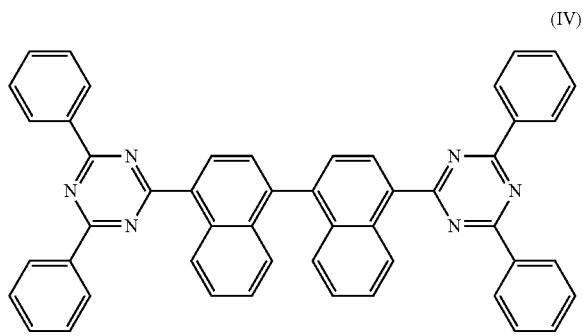 [SMILES: c1ccc(-c2nc(-c3ccccc3)nc(-c3ccc(-c4ccc(-c5nc(-c6ccccc6)nc(-c6ccccc6)n5)c5ccccc45)c4ccccc34)n2)cc1]

Experimental Example 1

The driving voltage and the light emitting efficiency of the organic light emitting devices manufactured in Examples 1-1 to 1-11 and Comparative Examples 1-1 to 1-4 were measured applying a current density of 10 mA/cm², and the time ($T_{90}$) required for the initial luminance to decrease to 90% of its initial value at a current density of 20 mA/cm² was measured. The results are shown in Table 1 below.

TABLE 1

| Com-pound | Voltage (V at 10 mA/cm²) | Efficiency (cd/A at 10 mA/cm²) | Color coor-dinates (x, y) | Lifetime (h) $T_{90}$ at 20 mA/Cm² |
|---|---|---|---|---|
| Example 1-1 | 1 | 4.30 | 5.41 | (0.142, 0.099) | 162 |
| Example 1-2 | 2 | 4.37 | 5.27 | (0.142, 0.097) | 172 |
| Example 1-3 | 3 | 4.46 | 5.35 | (0.142, 0.096) | 153 |
| Example 1-4 | 4 | 4.59 | 5.21 | (0.142, 0.099) | 203 |
| Example 1-5 | 5 | 4.48 | 5.34 | (0.142, 0.096) | 150 |
| Example 1-6 | 6 | 4.38 | 5.49 | (0.142, 0.096) | 161 |
| Example 1-7 | 7 | 4.36 | 5.45 | (0.142, 0.097) | 163 |
| Example 1-8 | 8 | 4.32 | 5.43 | (0.142, 0.096) | 164 |
| Example 1-9 | 9 | 4.32 | 5.49 | (0.142, 0.099) | 164 |
| Example 1-10 | 10 | 4.31 | 5.45 | (0.141, 0.046) | 173 |
| Example 1-11 | 11 | 4.35 | 5.42 | (0.141, 0.099) | 152 |
| Comparative Example 1-1 | I | 4.71 | 3.97 | (0.138, 0.044) | 98 |
| Comparative Example 1-2 | II | 4.60 | 4.14 | (0.140, 0.047) | 111 |
| Comparative Example 1-3 | III | 4.61 | 4.18 | (0.138, 0.044) | 106 |
| Comparative Example 1-4 | IV | 4.81 | 5.21 | (1.141, 0.048) | 99 |

From the results of Table 1, it can be confirmed that the heterocyclic compound of Chemical Formula 1 having an asymmetric structure based on a binaphthalene skeleton to which a specific cyan group and a heterocyclic ring are bonded respectively in accordance with the present invention, can be used in an organic material layer capable of simultaneously performing electron injection and electron transport.

In addition, when comparing Examples 1-1 to 1-11 with Comparative Example 1-1, it can be confirmed that a compound in which a binaphthalene skeleton structure is asymmetrically bonded to a heterocycle such as triazine as in Chemical Formula 1 can exhibit superior characteristics in terms of driving voltage, efficiency, and lifetime in the organic light emitting device, as compared with the compound (I) in which all substituents of the binaphthalene group are symmetrically substituted in the triazine skeleton. These results are obtained because the heterocyclic compound of Chemical Formula 1 is superior in thermal stability as compared with a material having a high molecular weight as in the above-mentioned compound (I) having a symmetrical structure used in Comparative Example 1-1, and has a deep HOMO level of 6.0 eV or more, high triple energy (ET), and hole stability.

Further, when comparing Examples 1-1 to 1-11 with Comparative Example 1-2, it was confirmed that even when the binaphthalene skeleton contains nitrogen atom-containing heterocyclic substituents with an asymmetric structure as in the above-mentioned compound (II), triazines or specific heterocycle-bonded compounds as in Chemical Formulas 2 to 5 according to the present invention exhibited superior characteristics in terms of voltage, efficiency, and lifetime.

In particular, when comparing Example 1-1 with Comparative Example 1-3, even in the case of a hetero-compound containing binaphthalene, it exhibited excellent characteristics in terms of driving voltage, efficiency, and lifetime when used in an organic light emitting device, as compared with the material having a skeleton structure to which naphthyl and biphenylene are bonded as in the above-mentioned compound (III).

Further, when comparing Examples 1-1 to 1-11 with Comparative Examples 1-4, it was confirmed that as compared with the case where both functional groups bonded to the binaphthalene skeleton have a triazine-based structure as in the above-mentioned compound (IV), the case where two functional groups bonded to the binaphthalene skeleton have different structures can more easily control the electron transport capability, band gap, energy level, and thermal properties, thereby exhibiting superior characteristics in terms of voltage, efficiency, and lifetime.

Moreover, when the heterocyclic compound of Chemical Formula 1 is used for an organic material layer capable of simultaneously performing electron injection and electron transport, the n-type dopants used in the art can be mixed and used. Accordingly, the heterocyclic compound of Chemical Formula 1 has a low driving voltage and high efficiency, and can improve the stability of the device due to hole stability of the compound.

Example 2-1

A glass substrate on which ITO (indium tin oxide) was coated as a thin film to a thickness of 1000 Å was put into distilled water in which a detergent was dissolved, and ultrasonically cleaned. In this case, a product manufactured by Fischer Co., was used as the detergent, and as the distilled water, distilled water filtered twice using a filter manufactured by Millipore Co., was used. After the ITO was cleaned for 30 minutes, ultrasonic cleaning was repeated twice using distilled water for 10 minutes. After the cleaning with distilled water was completed, the substrate was ultrasonically cleaned with solvents of isopropyl alcohol, acetone, and methanol, then dried, and then transferred to a plasma cleaner. In addition, the substrate was cleaned for 5 minutes using oxygen plasma, and then transferred to a vacuum depositor.

On the ITO transparent electrode thus prepared, the following compound [HI-A] was thermally vacuum deposited to have a thickness of 600 Å, thereby forming a hole injection layer. The following compound [HAT] (50 Å) and the following compound [HT-A] (600 Å) were sequentially vacuum deposited on the hole injection layer to form a hole transfer layer. Then, the following compounds [BH] and [BD] were vacuum deposited at a weight ratio of 25:1 on the hole transport layer to a thickness of 200 Å to form a light emitting layer. The compound 1 prepared in Preparation Example 1 was vacuum deposited on the light emitting layer to form an electron control layer with a thickness of 200 Å. The following compound [ET] and the following compound [LiQ] (lithium quinolate) were vacuum deposited at a weight ratio of 1:1 on the electron control layer to form an electron injection and transport layer with a thickness of 150 Å. Lithium fluoride (LiF) and aluminum were sequentially deposited to have a thickness of 10 Å and 1000 Å, respectively, on the electron injection and transport layer, thereby forming a cathode.

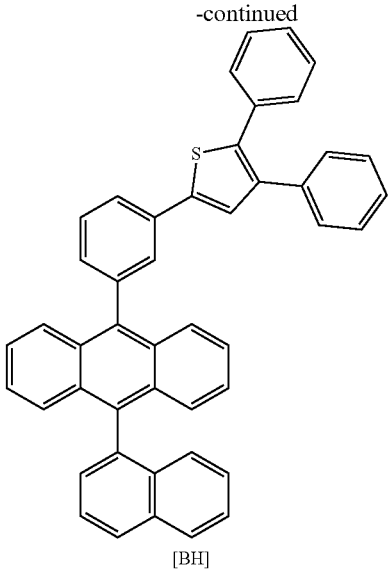

[BH]

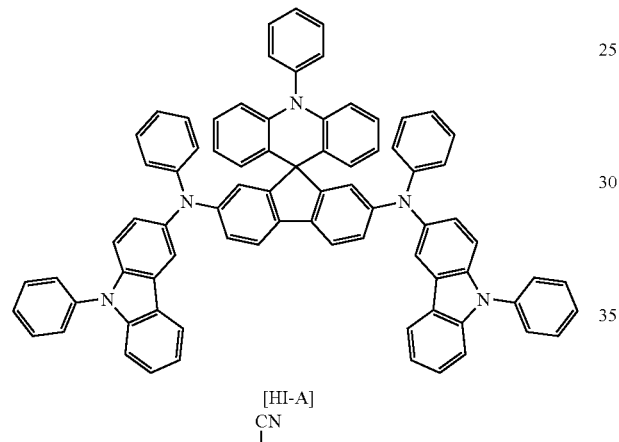

[HI-A]

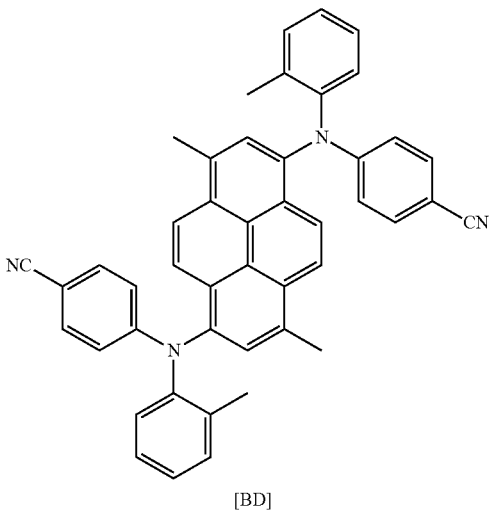

[BD]

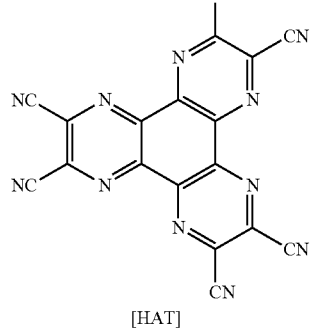

[HAT]

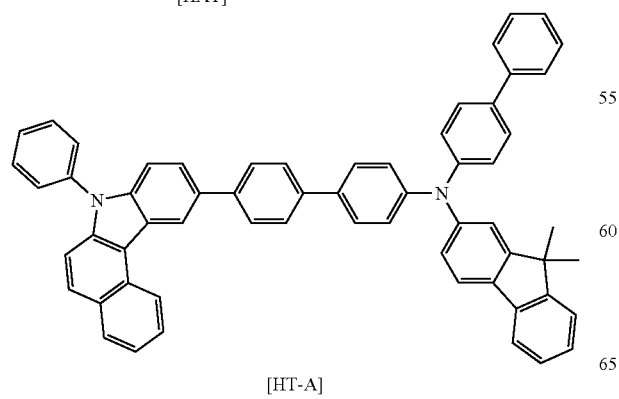

[HT-A]

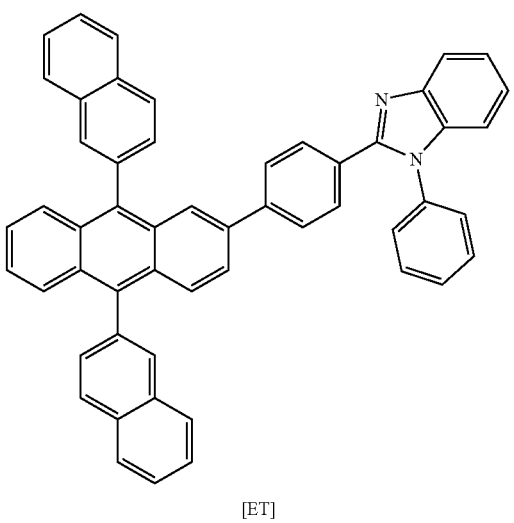

[ET]

-continued

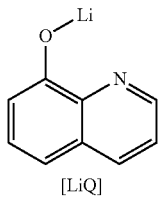

[LiQ]

In the above-mentioned process, the vapor deposition rate of the organic material was maintained at 0.4 to 0.9 Å/second, the deposition rate of lithium fluoride of the cathode was maintained at 0.3 Å/second, the deposition rate of aluminum was maintained at 2 Å/second, and the degree of vacuum during the deposition was maintained at $1\times10^{-7}$ to $5\times10^{-8}$ Torr, thereby manufacturing an organic light emitting device.

Examples 2-2 to 2-11

An organic light emitting device was manufactured in the same manner as in Example 2-1, except that one compound of the compounds 2 to 11 as shown in Table 2 below was used instead of Compound 1 in Example 2-1.

Comparative Examples 2-1 to 2-344

An organic light emitting device was manufactured in the same manner as in Example 2-1, except that the compounds (I), (II), or (III) having the following structures as shown in Table 2 below was used instead of Compound 1 in Example 2-1.

(I)

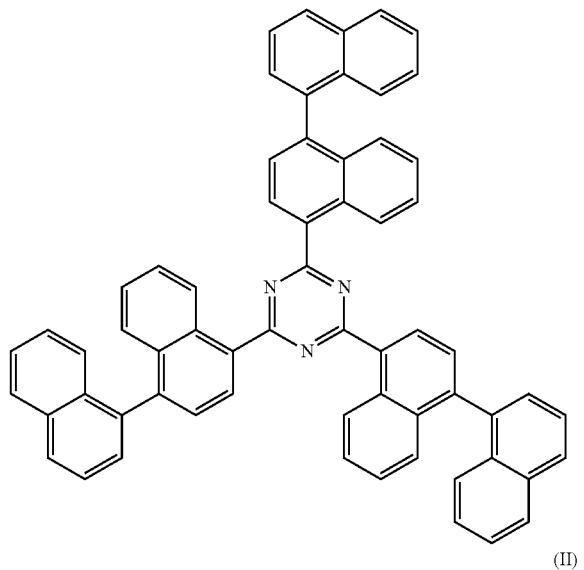

(II)

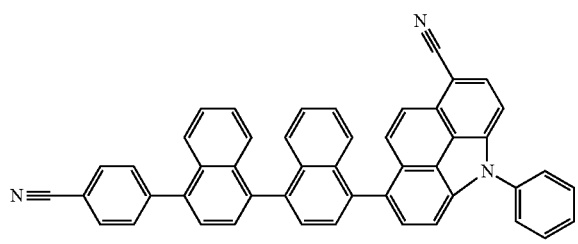

(III)

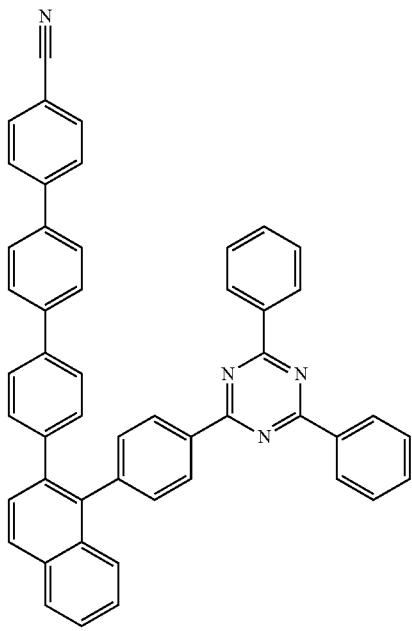

Comparative Example 2-4

An organic light emitting device was manufactured in the same manner as in Example 2-1, except that the compound (IV) having the following structure as shown in Table 2 below was used instead of Compound 1 in Example 2-1.

(IV)

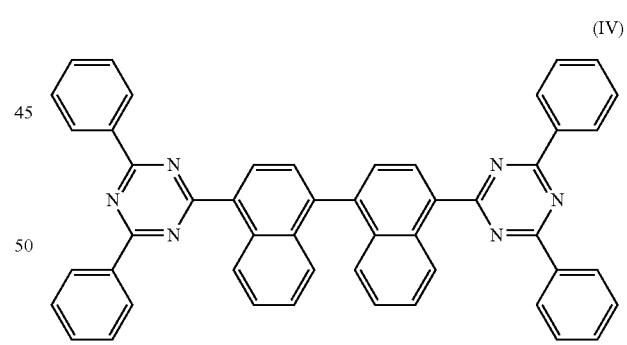

Experimental Example 2

The driving voltage and the light emitting efficiency of the organic light emitting devices manufactured in Examples 2-1 to 2-11 and Comparative Examples 2-1 to 2-4 were measured after applying a current density of 10 mA/cm², and the time ($T_{90}$) required for the initial luminance to decrease to 90% of its initial value at a current density of 20 mA/cm² was measured. The results are shown in Table 2 below.

TABLE 2

| Compound | | Voltage (V at 10 mA/cm²) | Efficiency (cd/A at 10 mA/cm²) | Color coordinates (x, y) | Lifetime (h) $T_{90}$ at 20 mA/Cm² |
|---|---|---|---|---|---|
| Example 2-1 | 1 | 4.11 | 5.59 | (0.142, 0.096) | 246 |
| Example 2-2 | 2 | 4.09 | 5.69 | (0.142, 0.096) | 237 |
| Example 2-3 | 3 | 4.17 | 5.57 | (0.142, 0.099) | 277 |
| Example 2-4 | 4 | 4.21 | 5.06 | (0.142, 0.096) | 169 |
| Example 2-5 | 5 | 4.15 | 5.49 | (0.142, 0.098) | 248 |
| Example 2-6 | 6 | 4.20 | 5.46 | (0.142, 0.096) | 260 |
| Example 2-7 | 7 | 4.36 | 5.03 | (0.142, 0.096) | 159 |
| Example 2-8 | 8 | 4.08 | 5.68 | (0.142, 0.096) | 225 |
| Example 2-9 | 9 | 4.23 | 4.96 | (0.142, 0.099) | 158 |
| Example 2-10 | 10 | 4.18 | 5.50 | (0.141, 0.046) | 234 |
| Example 2-11 | 11 | 4.21 | 5.69 | (0.142, 0.096) | 240 |
| Comparative Example 2-1 | I | 4.74 | 3.77 | (0.142, 0.099) | 85 |
| Comparative Example 2-2 | II | 4.52 | 3.89 | (0.151, 0.109) | 88 |
| Comparative Example 2-3 | III | 4.51 | 3.92 | (0.151, 0.109) | 84 |
| Comparative Example 2-4 | IV | 4.81 | 5.11 | (0.151, 0.100) | 81 |

From the results of Table 2, it can be seen that the heterocyclic compound of Chemical Formula 1 can be used for the electron control layer of the organic light emitting device.

EXPLANATION OF SIGNS

| | |
|---|---|
| 1: substrate | 2: anode |
| 3: light emitting layer | 4: cathode |
| 5: hole injection layer | 6: hole transport layer |
| 7: light emitting layer | 8: electron transport layer |

The invention claimed is:

1. A binaphthalene compound of Chemical Formula 1:

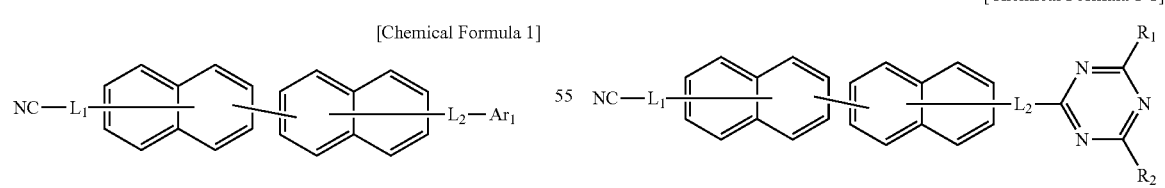

[Chemical Formula 1]

wherein, in Chemical Formula 1:

$L_1$ is a single bond, or a substituted or unsubstituted $C_{6-60}$ arylene;

$L_2$ is a single bond or a substituted or unsubstituted $C_{6-60}$ arylene; and $Ar_1$ is one of the following Chemical Formula 2, 3, 4, or 5,

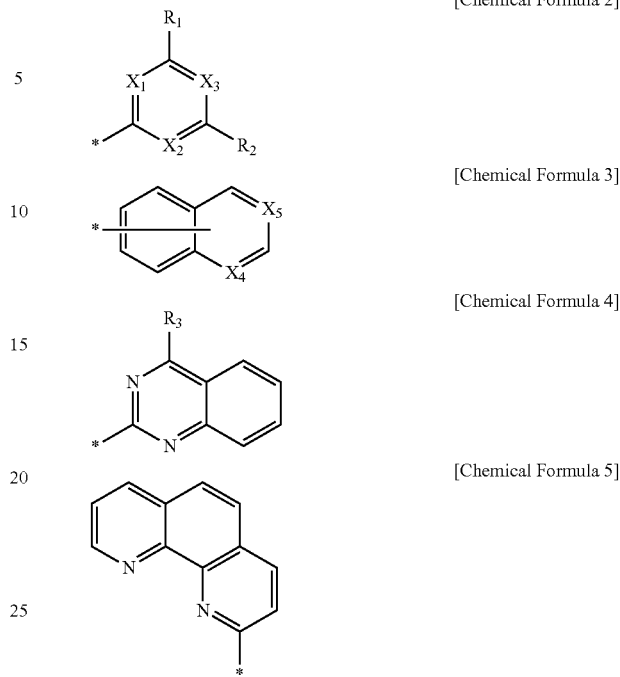

[Chemical Formula 2]

[Chemical Formula 3]

[Chemical Formula 4]

[Chemical Formula 5]

wherein, in Chemical Formulas 2 to 5:

$X_1$, $X_2$, and $X_3$ are each independently N or $CR_4$, where there is at least one N;

$X_4$ and $X_5$ are each independently N or $CR_5$, where there is at least one N;

$R_1$, $R_2$, and $R_3$ are each independently a substituted or unsubstituted $C_{1-40}$ alkyl, a substituted or unsubstituted $C_{6-60}$ aryl, or a substituted or unsubstituted $C_{5-60}$ heteroaryl, or $R_1$, $R_2$, and $R_3$ are each independently one in which a hydrogen atom of the alkyl, the aryl, or the heteroaryl is substituted with deuterium or CN; and $R_4$ and $R_5$ are each independently hydrogen, deuterium, a substituted or unsubstituted $C_{1-40}$ alkyl, a substituted or unsubstituted $C_{6-60}$ aryl, or a substituted or unsubstituted $C_{5-60}$ heteroaryl.

2. The compound according to claim 1, wherein the compound of Chemical Formula 1 is one of the following Chemical Formula 1-1, 1-2, 1-3, 1-4, 1-5, 1-6, or 1-7:

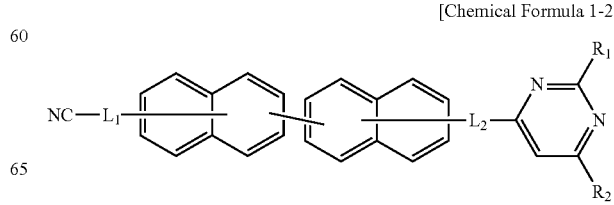

[Chemical Formula 1-1]

[Chemical Formula 1-2]

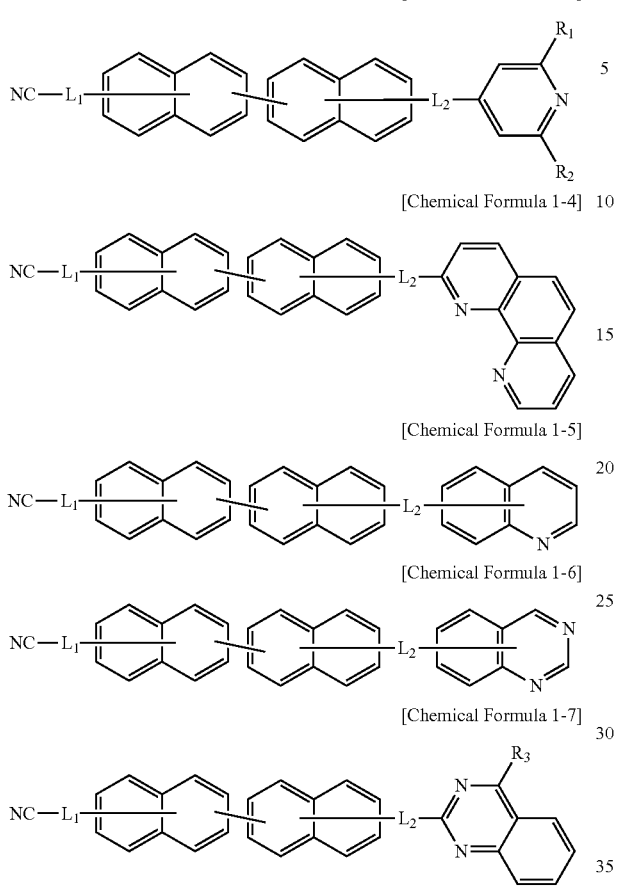

wherein, in Chemical Formulas 1-1, 1-2, 1-3, 1-4, 1-5, 1-6, and 1-7:

$L_1$ is a single bond, or a substituted or unsubstituted $C_{6-60}$ arylene;

$L_2$ is a single bond, a substituted or unsubstituted $C_{6-60}$ arylene, or a substituted or unsubstituted $C_{5-60}$ heteroarylene; and $R_1$, $R_2$, and $R_3$ are each independently a substituted or unsubstituted $C_{1-40}$ alkyl, a substituted or unsubstituted $C_{6-60}$ aryl, or a substituted or unsubstituted $C_{5-60}$ heteroaryl, or $R_1$, $R_2$, and $R_3$ are each independently one in which a hydrogen atom of the alkyl, the aryl, or the heteroaryl is substituted with deuterium or CN.

3. A binaphthalene compound of Chemical Formula 1:

[Chemical Formula 1]

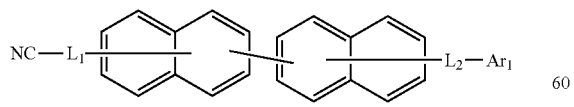

wherein, in Chemical Formula 1:

$L_1$ and $L_2$ are a bond, phenylene, or biphenylene; and $Ar_1$ is one of the following Chemical Formula 2, 3, 4, or 5,

[Chemical Formula 2]

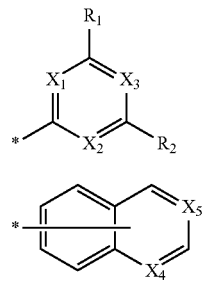

[Chemical Formula 3]

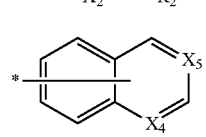

[Chemical Formula 4]

[Chemical Formula 5]

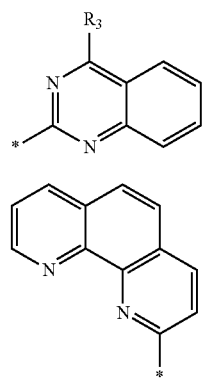

wherein, in Chemical Formulas 2 to 5:

$X_1$, $X_2$, and $X_3$ are each independently N or $CR_4$, where there is at least one N;

$X_4$ and $X_5$ are each independently N or $CR_5$, where there is at least one N;

$R_1$, $R_2$, and $R_3$ are each independently a substituted or unsubstituted $C_{1-40}$ alkyl, a substituted or unsubstituted $C_{6-60}$ aryl, or a substituted or unsubstituted $C_{5-60}$ heteroaryl, or $R_1$, $R_2$, and $R_3$ are each independently one in which a hydrogen atom of the alkyl, the aryl, or the heteroaryl is substituted with deuterium or CN; and $R_4$ and $R_5$ are each independently hydrogen, deuterium, a substituted or unsubstituted $C_{1-40}$ alkyl, a substituted or unsubstituted $C_{6-60}$ aryl, or a substituted or unsubstituted $C_{5-60}$ heteroaryl.

4. The compound according to claim 1, wherein $X_1$, $X_2$, $X_3$, $X_4$, and $X_5$ are N.

5. A binaphthalene compound of Chemical Formula 1:

[Chemical Formula 1]

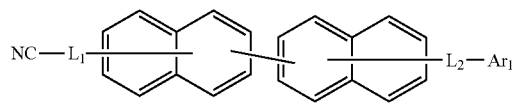

wherein, in Chemical Formula 1:

$L_1$ and $L_2$ are a bond, phenylene, or biphenylene; and $Ar_1$ is one of the following Chemical Formula 2, 3, 4, or 5,

[Chemical Formula 2]

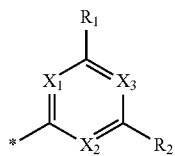

[Chemical Formula 3]

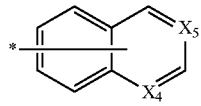

[Chemical Formula 4]

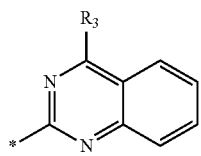

[Chemical Formula 5]

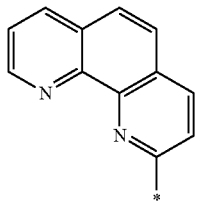

wherein, in Chemical Formulas 2 to 5:

$X_1$, $X_2$, and $X_3$ are each independently N or $CR_4$, where there is at least one N;

$X_4$ and $X_5$ are each independently N or $CR_5$, where there is at least one N; and $R_1$, $R_2$, $R_3$, $R_4$, and $R_5$ are hydrogen, phenyl, or pyridinyl.

6. The compound according to claim 1, wherein the compound of Chemical Formula 1 is any one selected from the group consisting of the following:

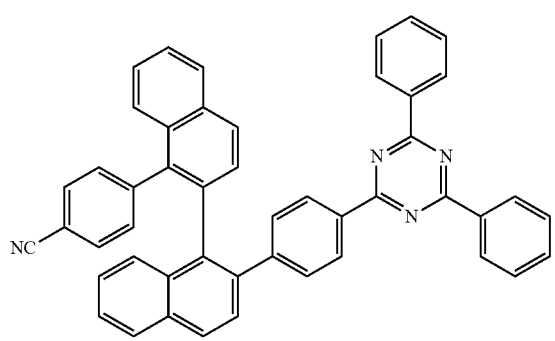

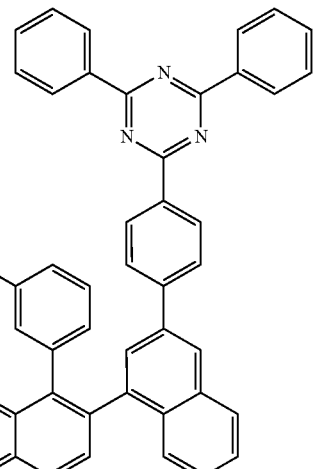

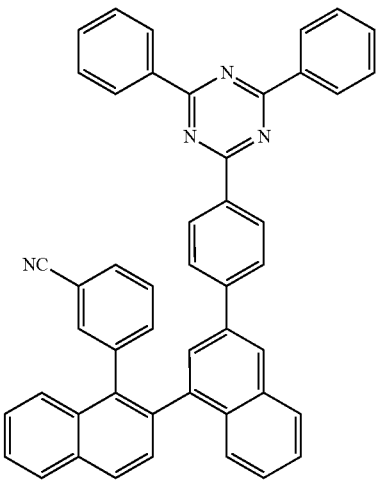

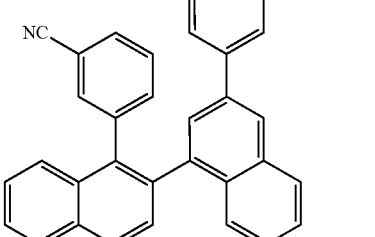

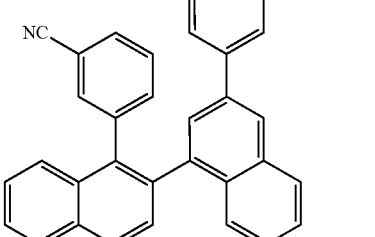

105
-continued
106
-continued
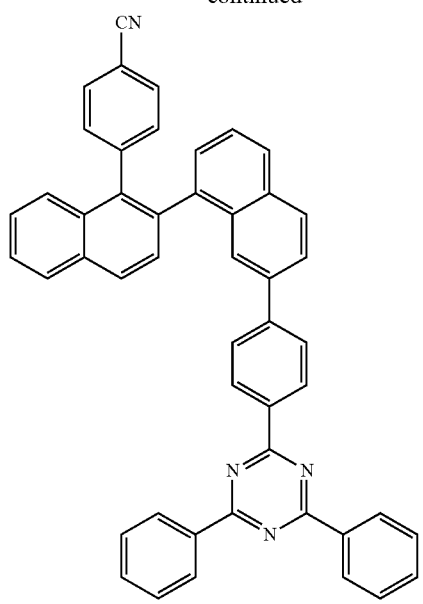
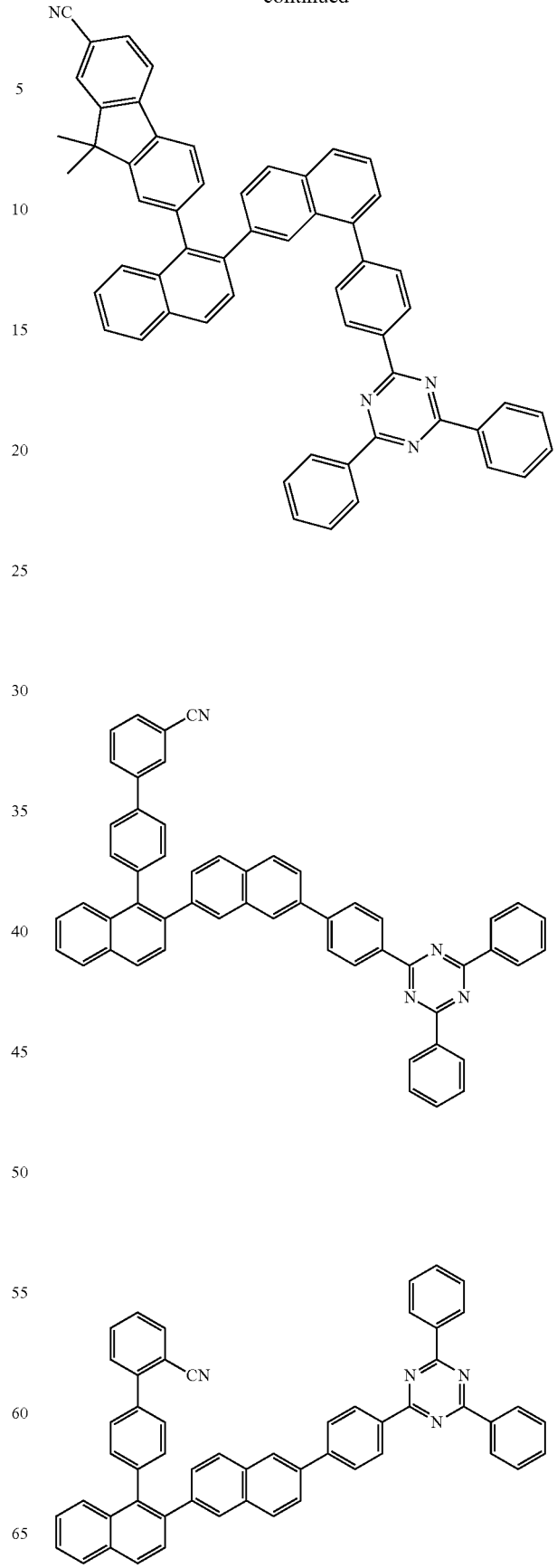

107
-continued
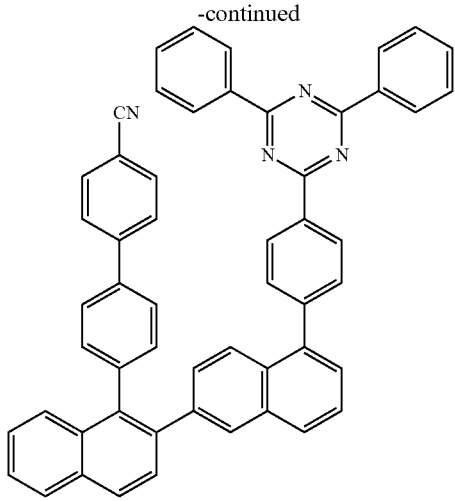
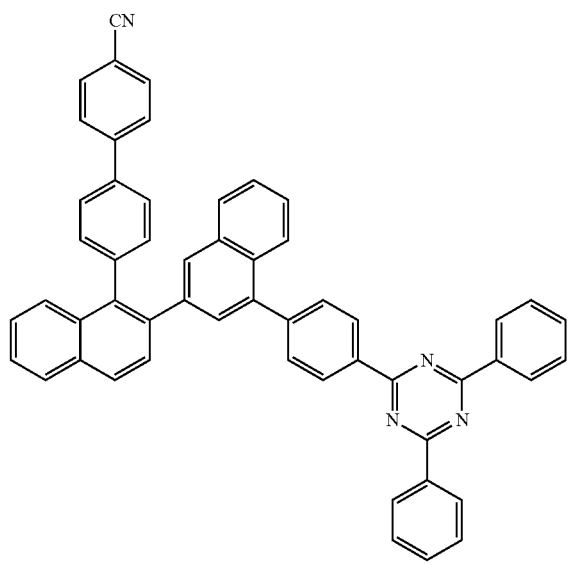
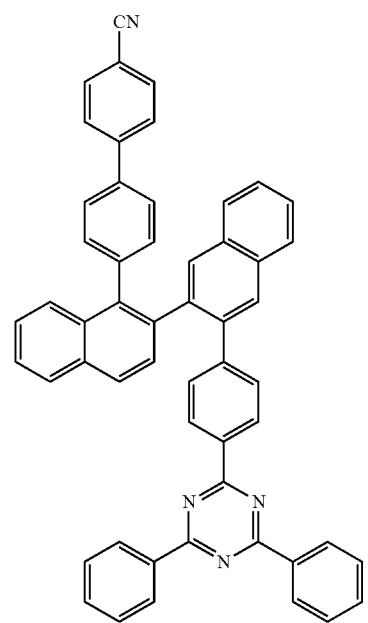
108
-continued
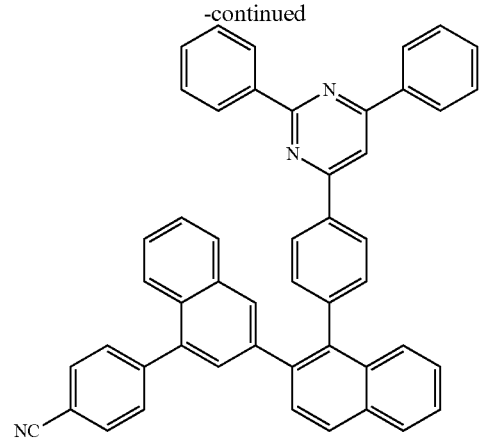
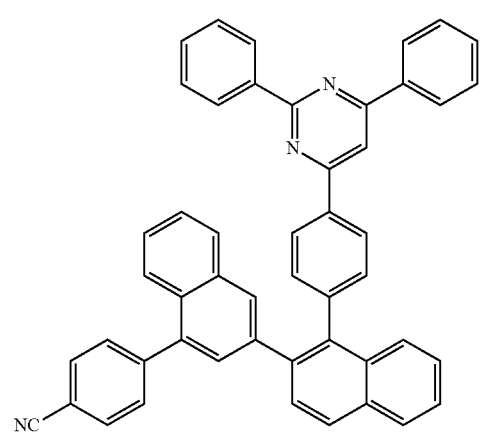
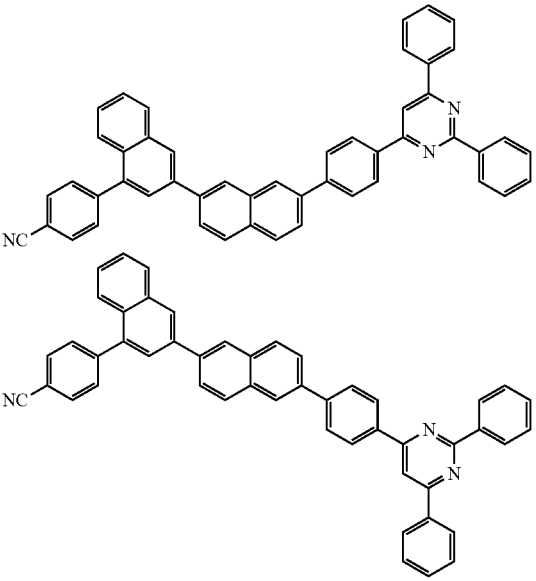

109
-continued
110
-continued
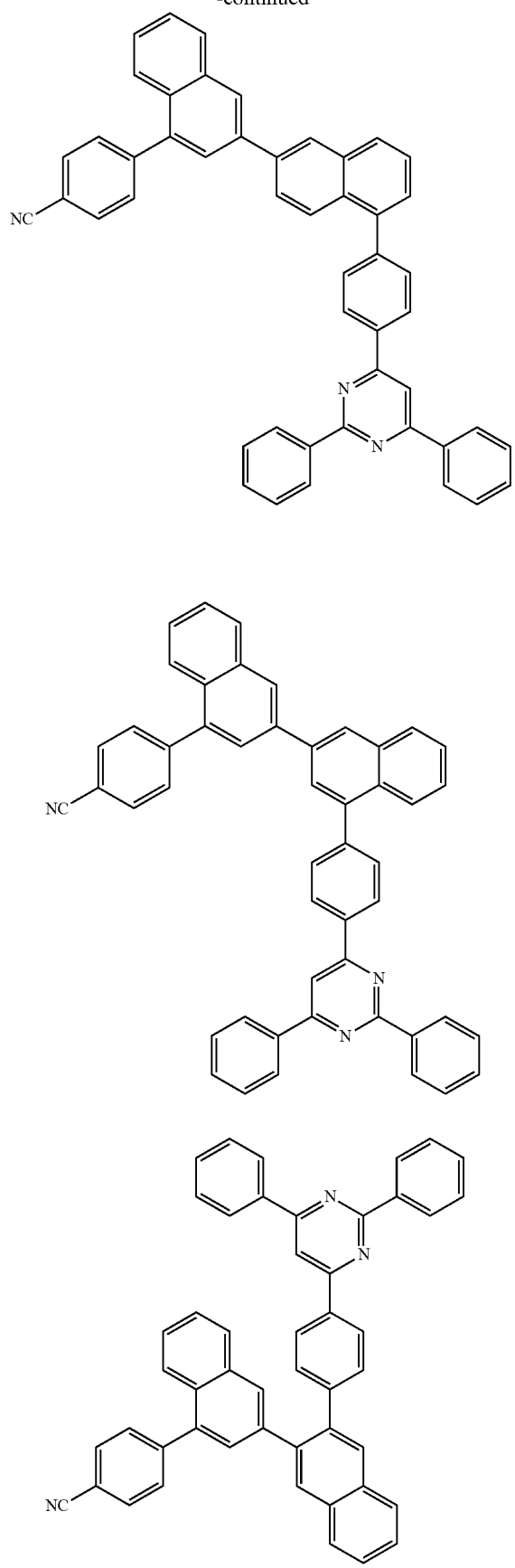
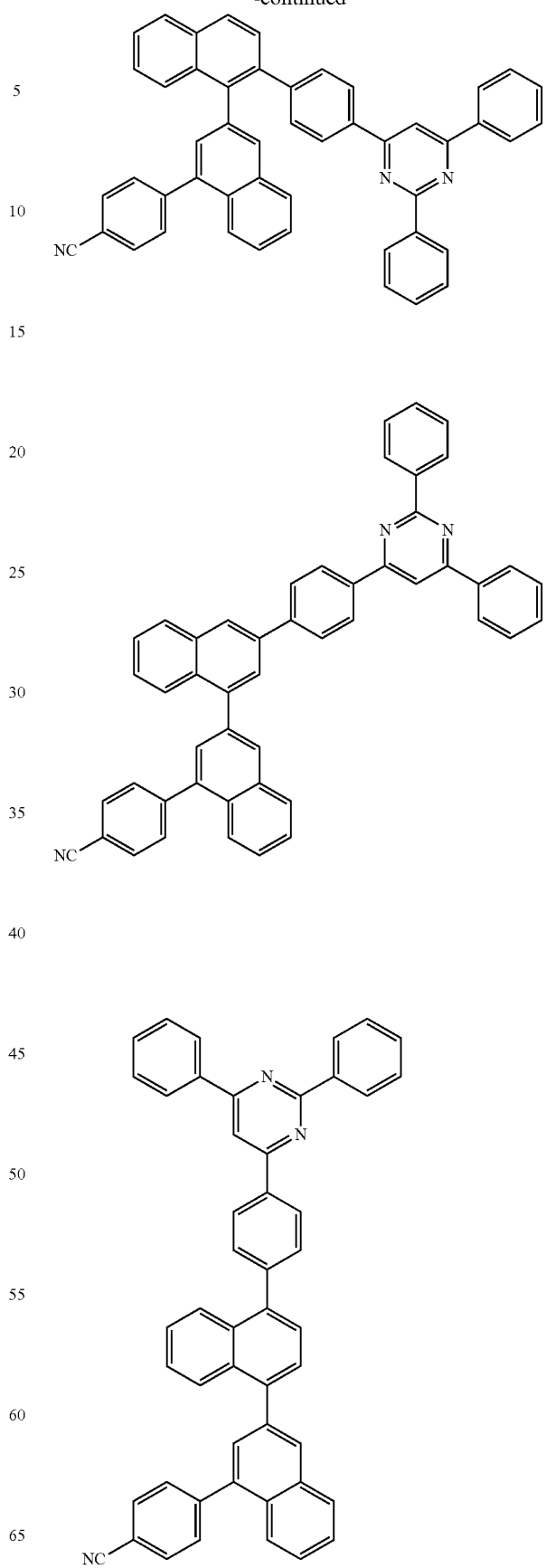

111
-continued
112
-continued
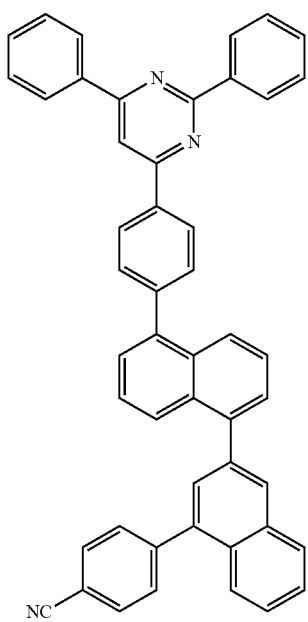
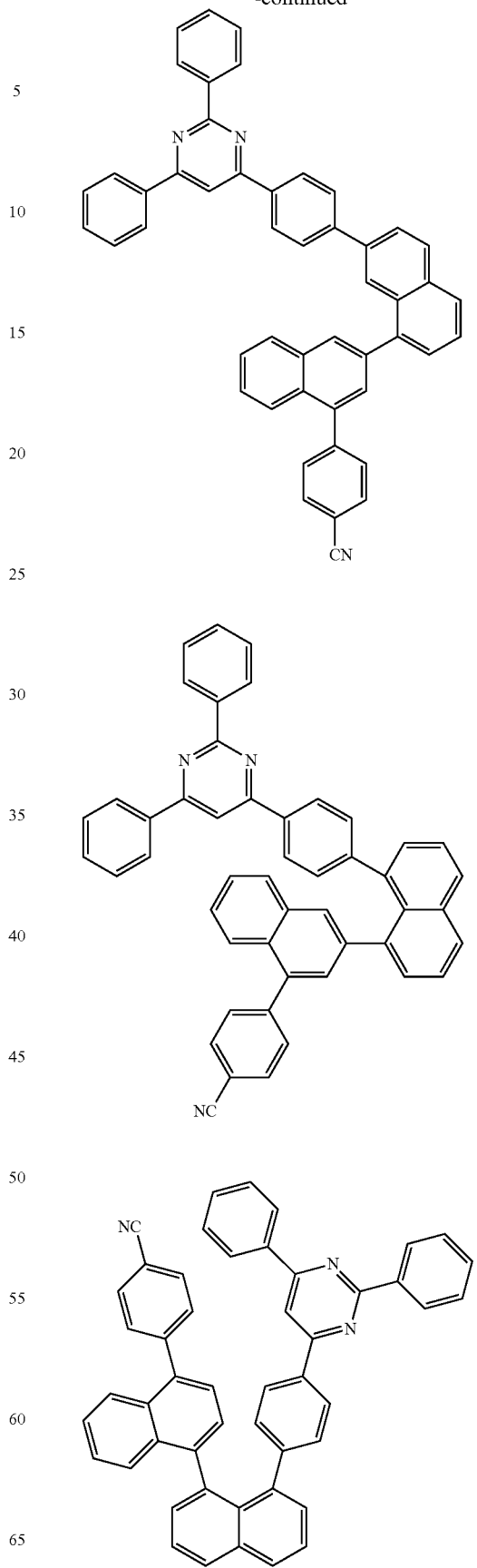

113
-continued
114
-continued
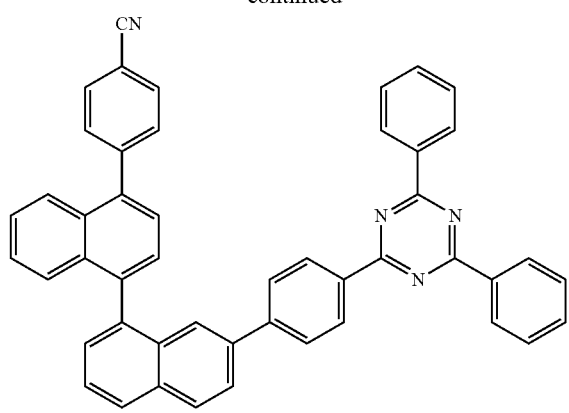
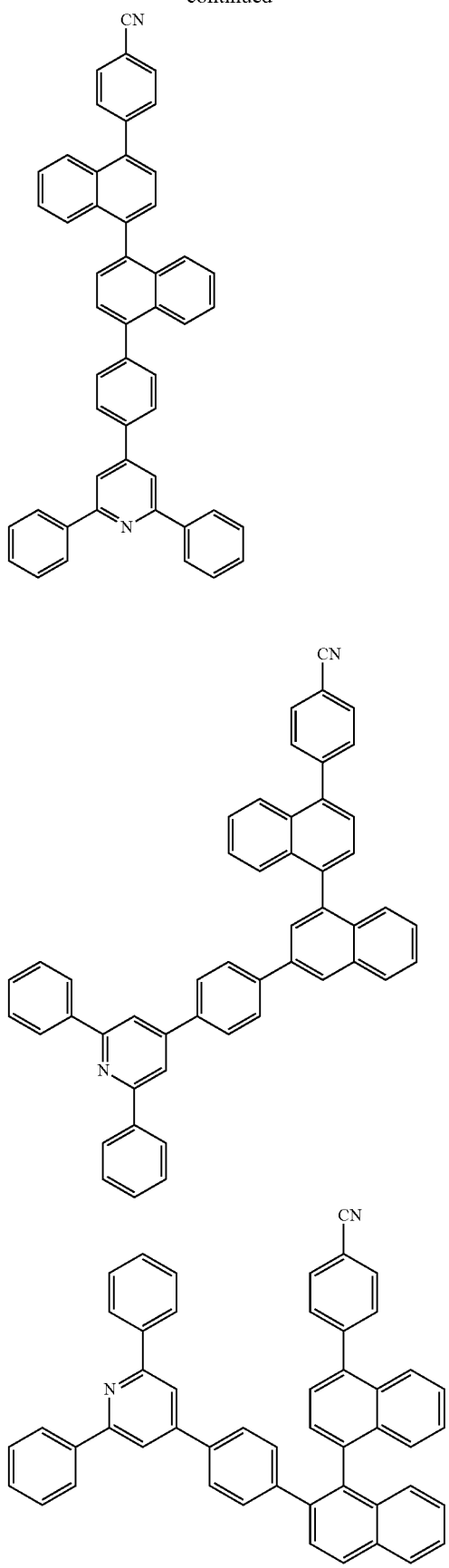

115
-continued
116
-continued
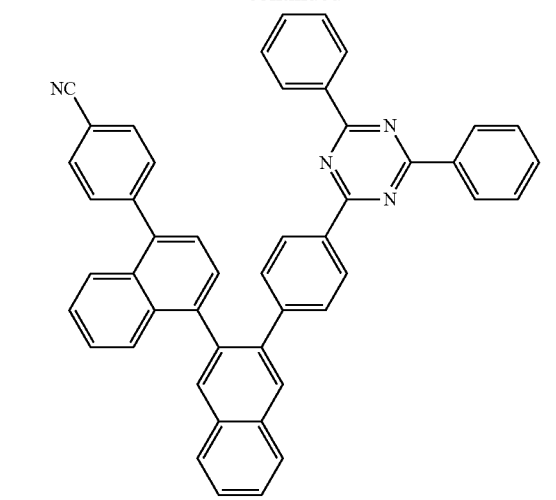
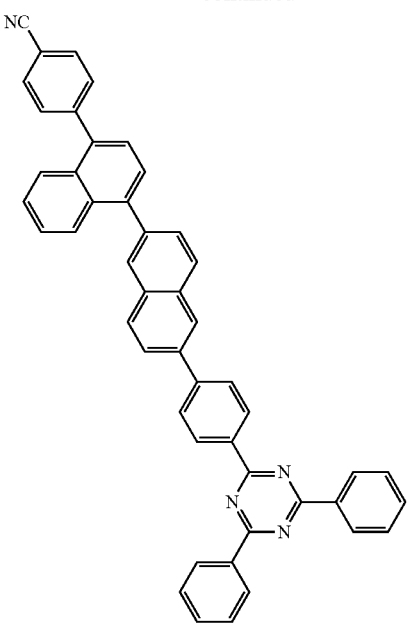
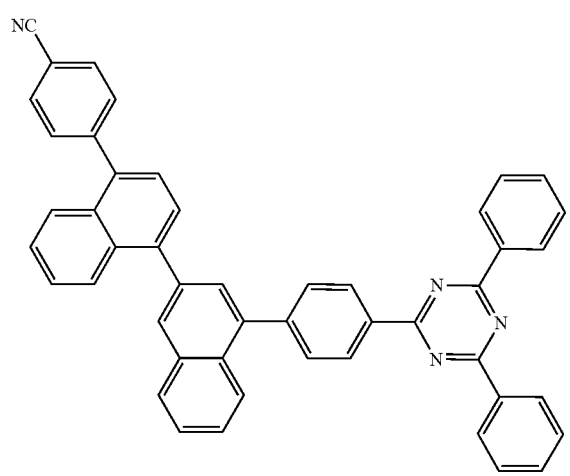
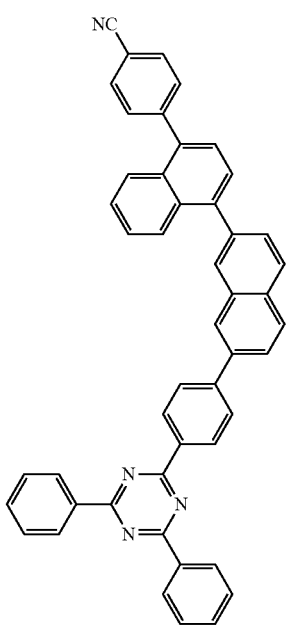

117
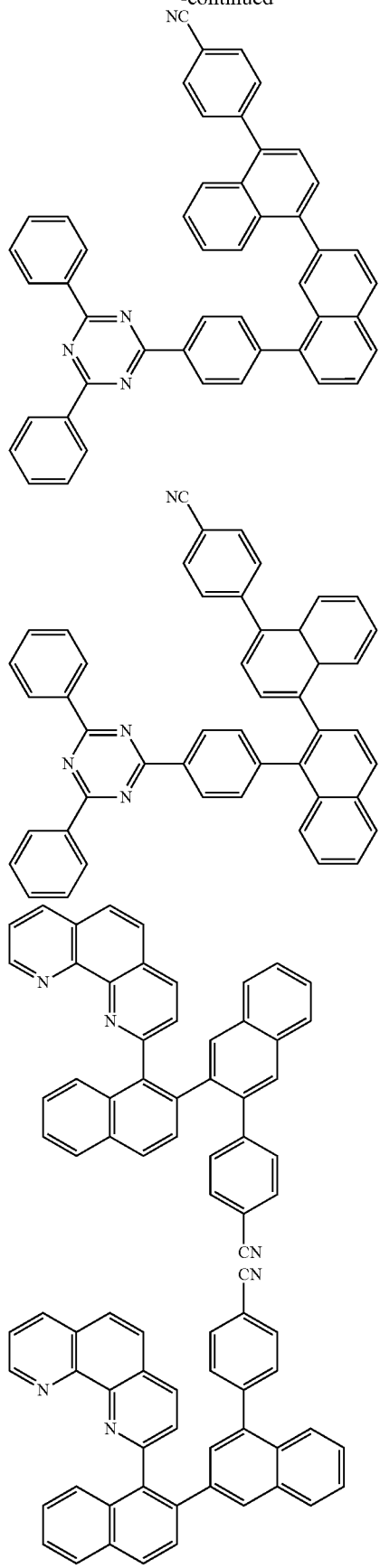
118
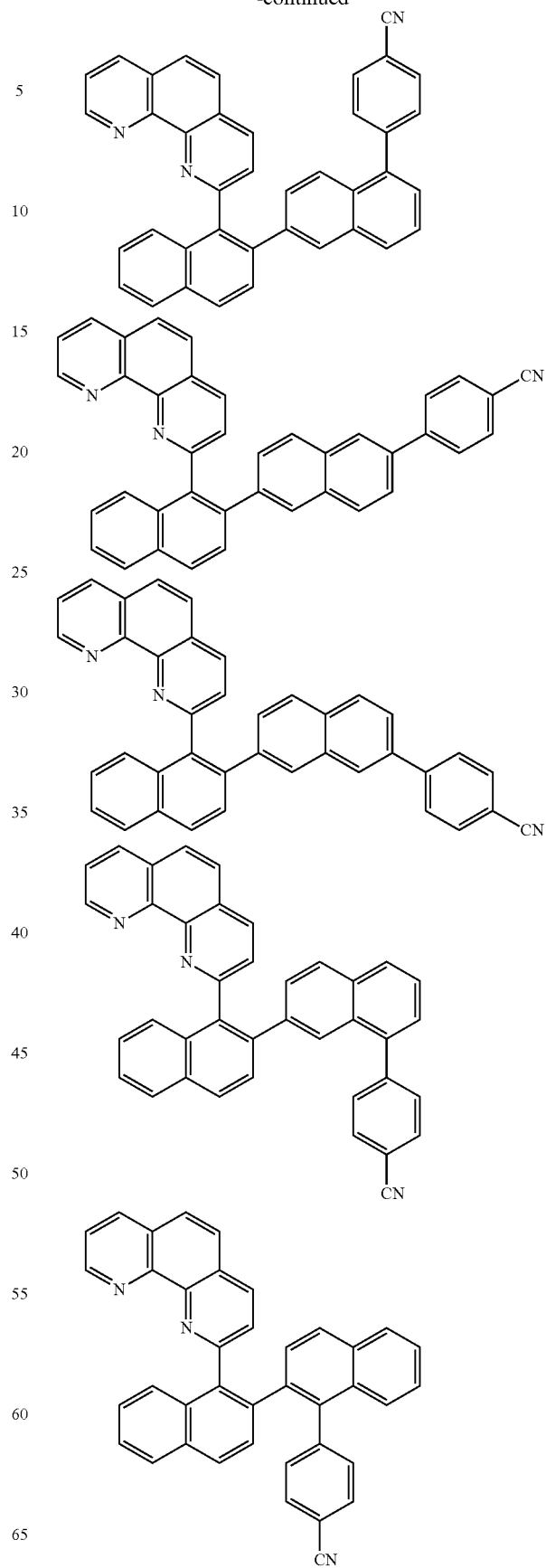

119
-continued
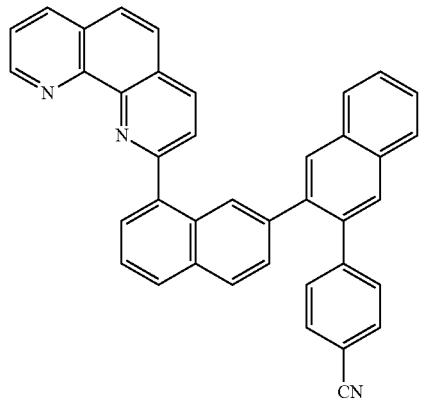
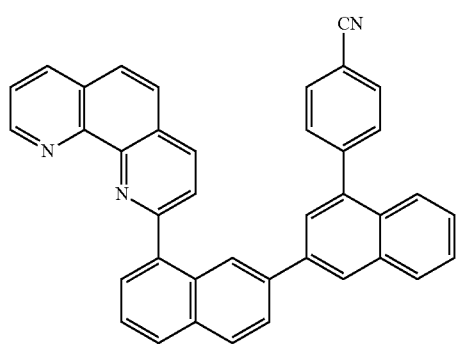
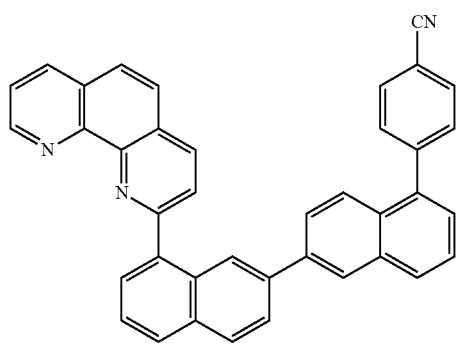
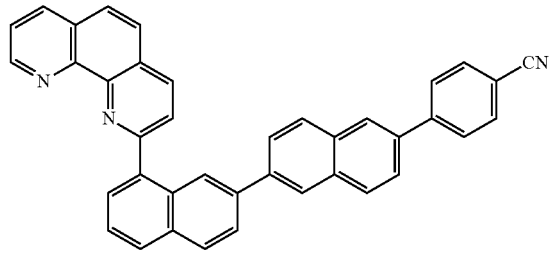
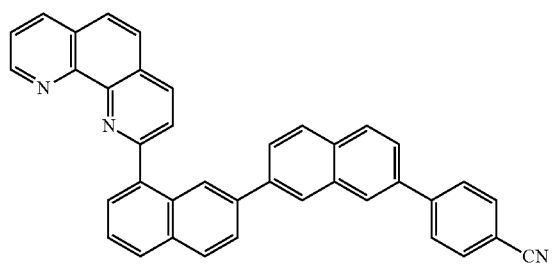
120
-continued
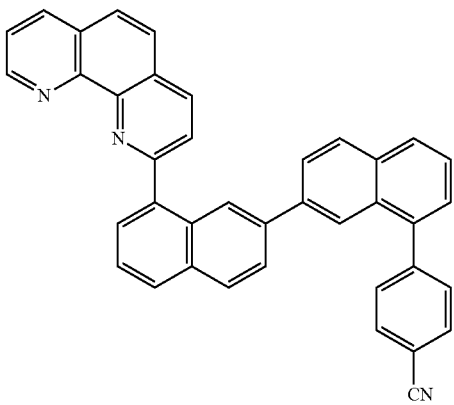
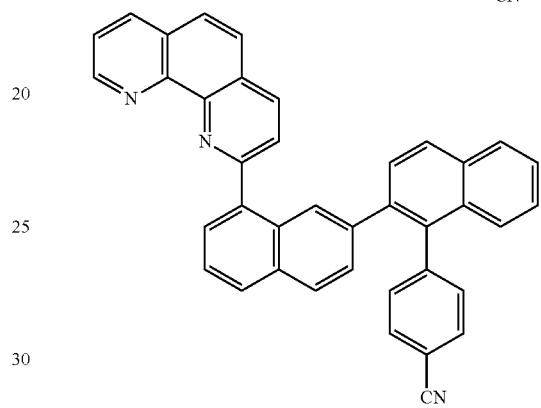
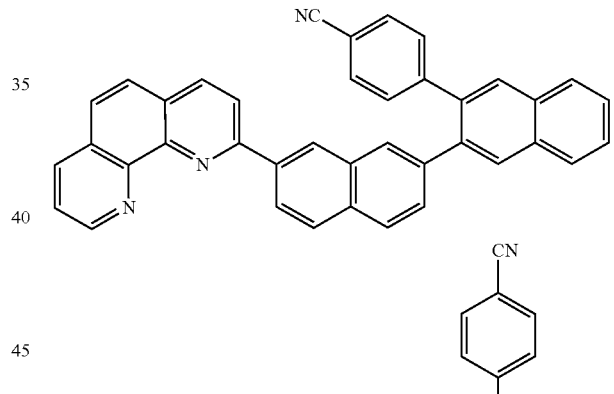
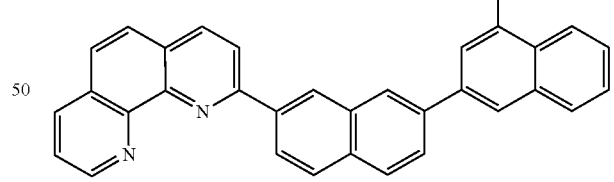
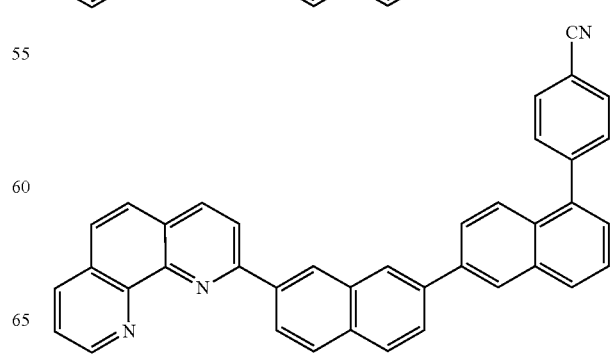

121
-continued
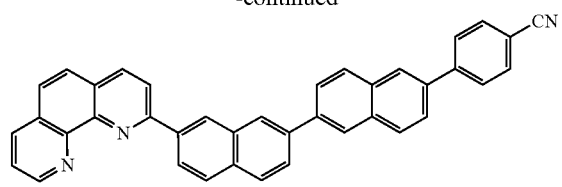
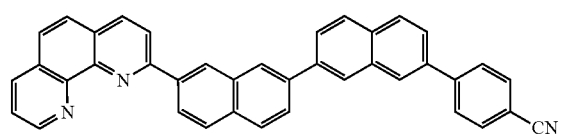
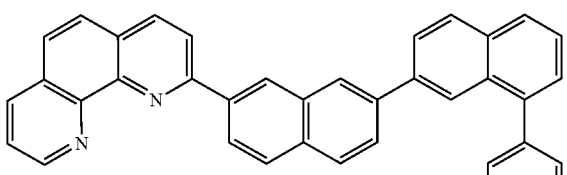
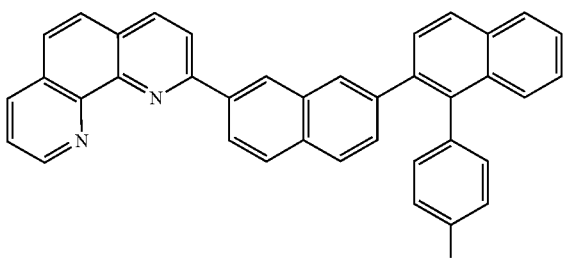
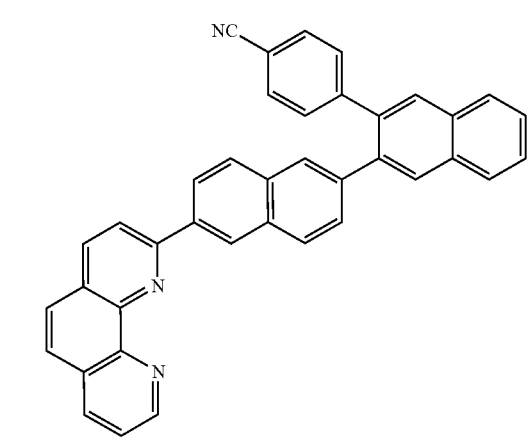
122
-continued
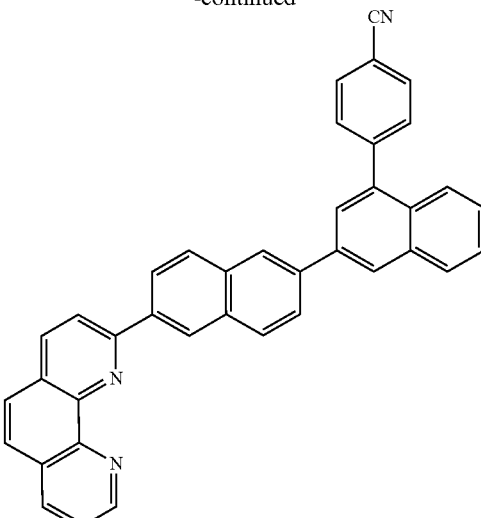
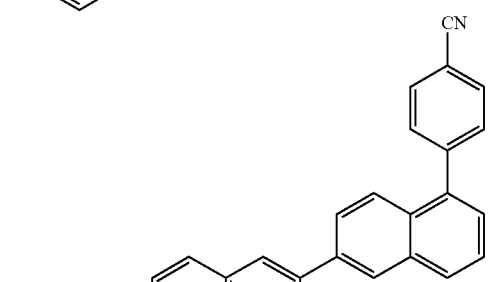
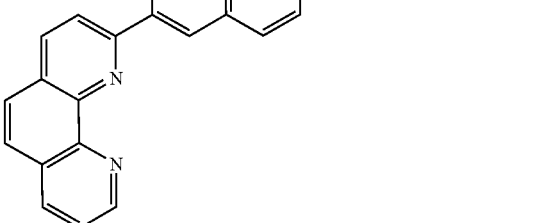
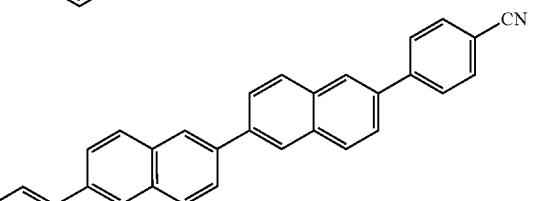
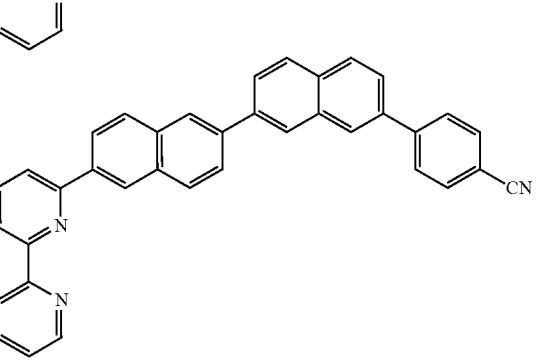

123
-continued
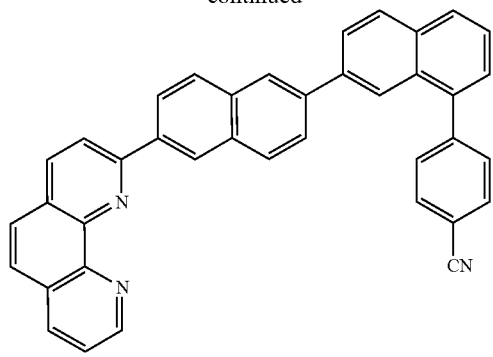
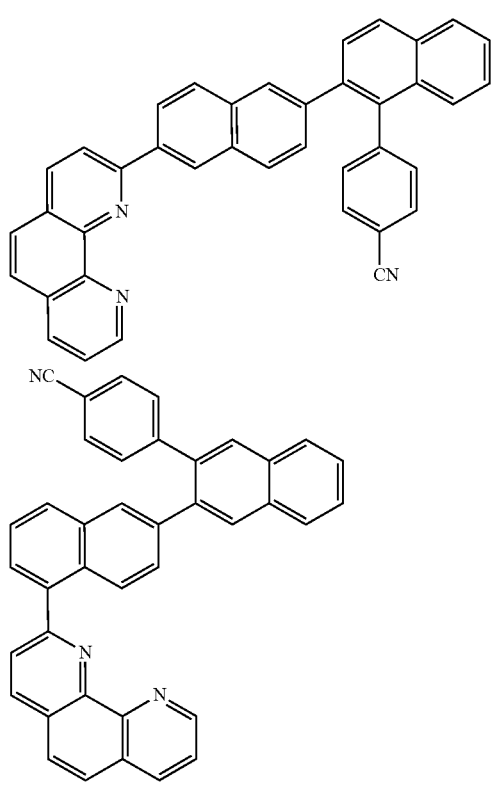
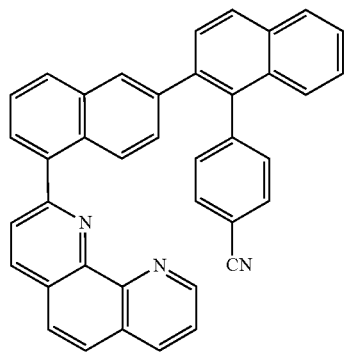
124
-continued
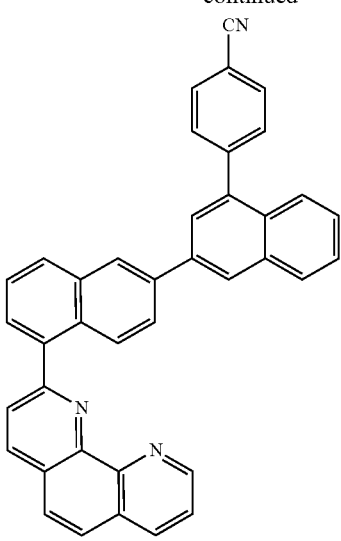
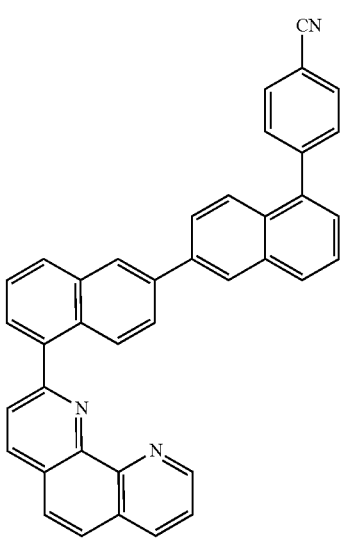
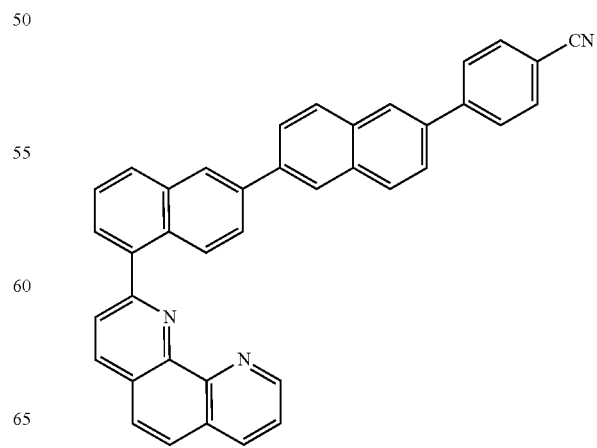

125
-continued
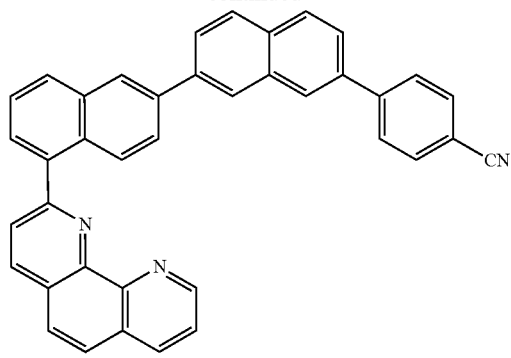
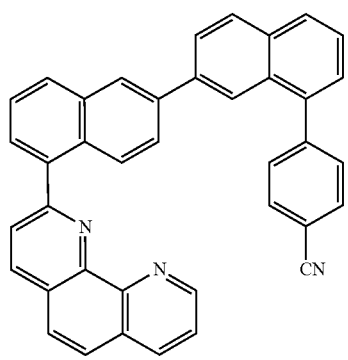
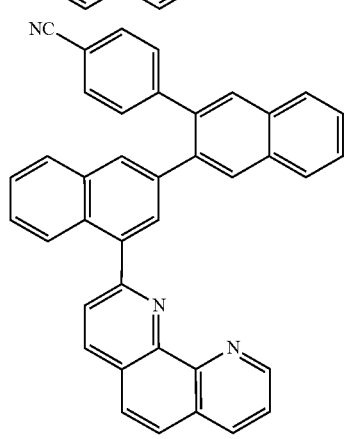
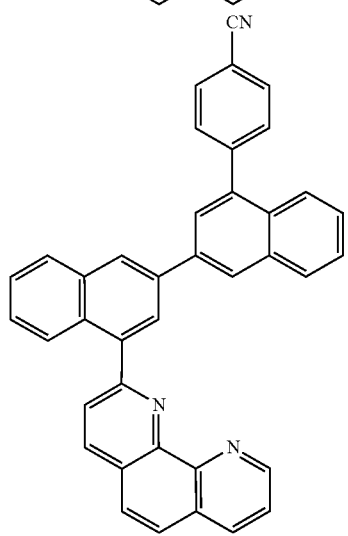
126
-continued
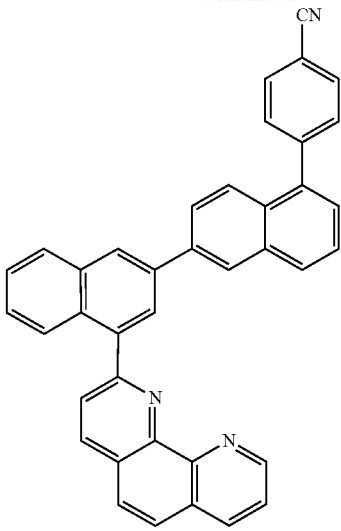
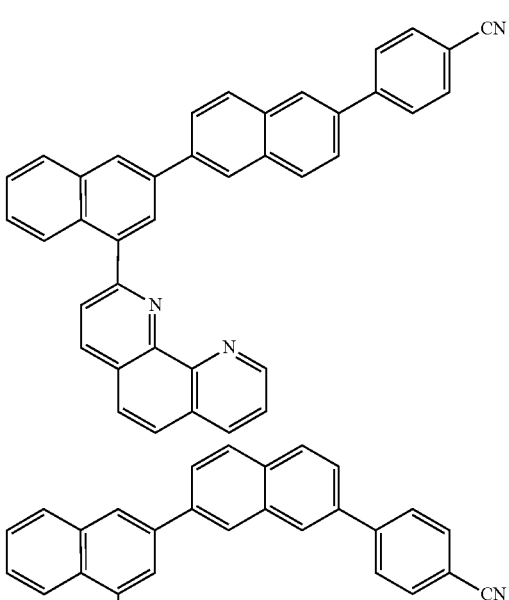
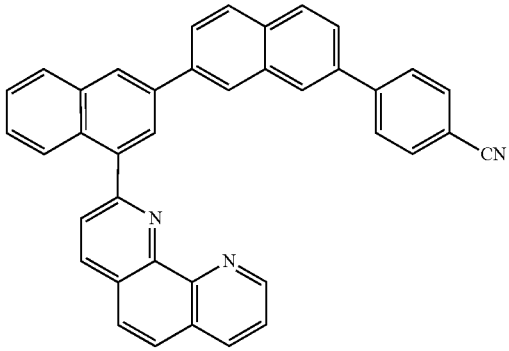
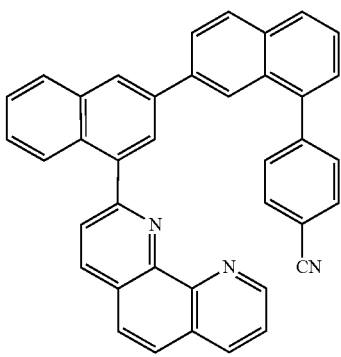

127
-continued
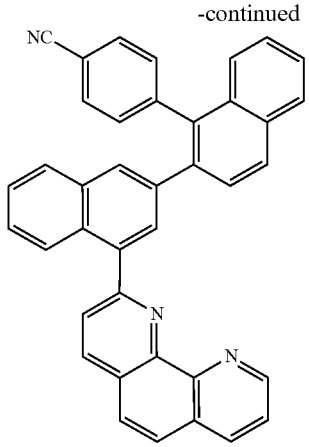
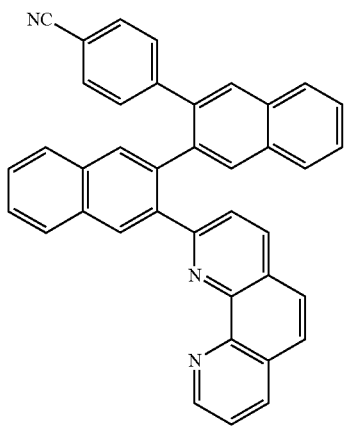
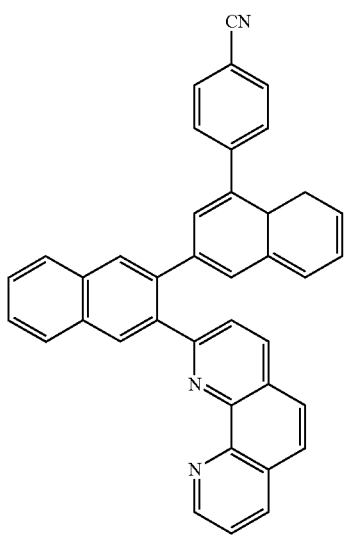
128
-continued
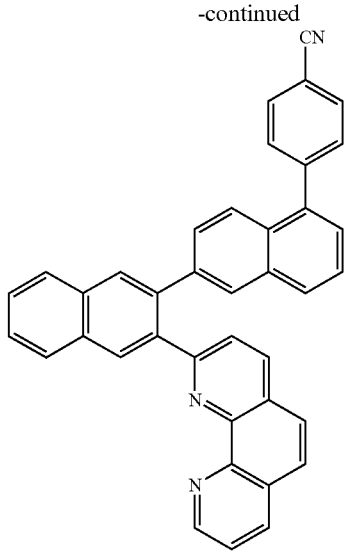
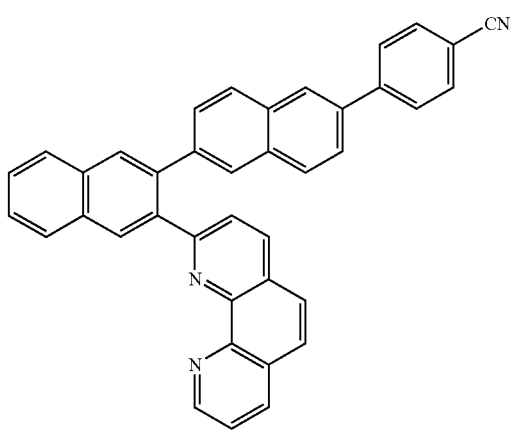
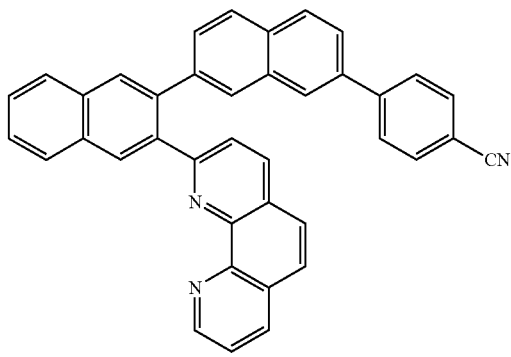

-continued
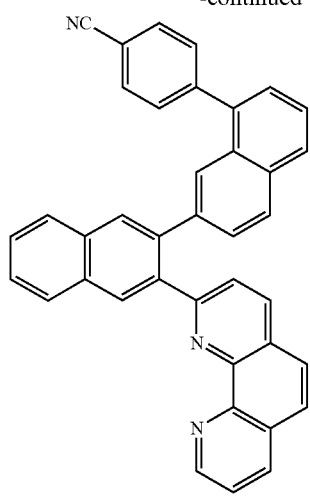
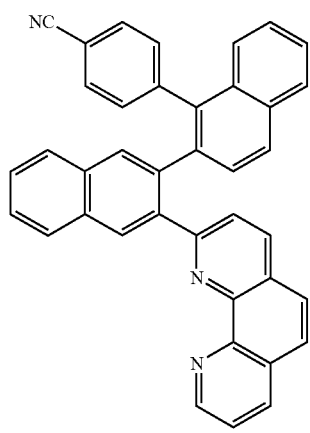
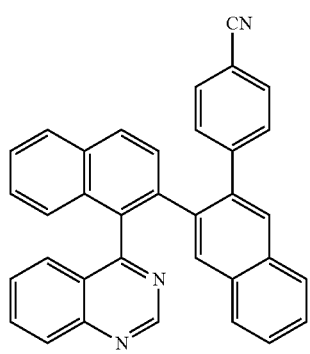
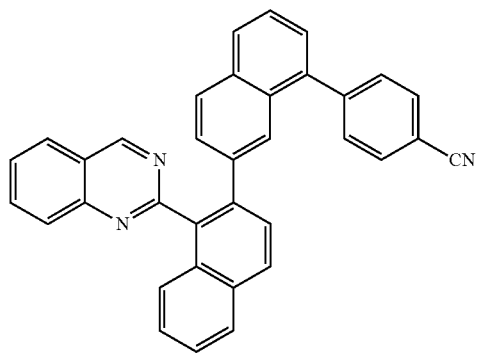
-continued
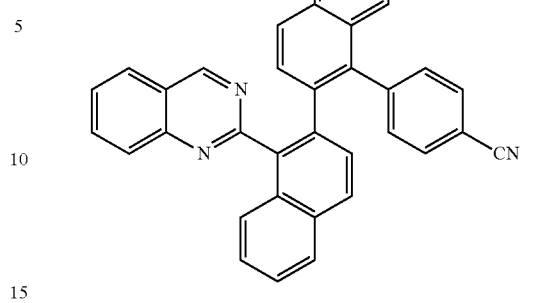
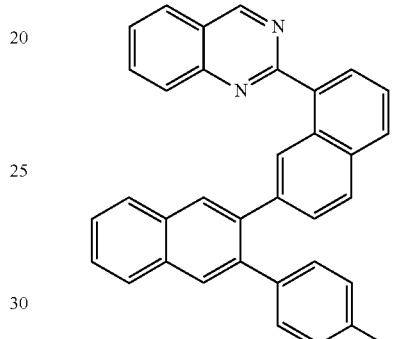
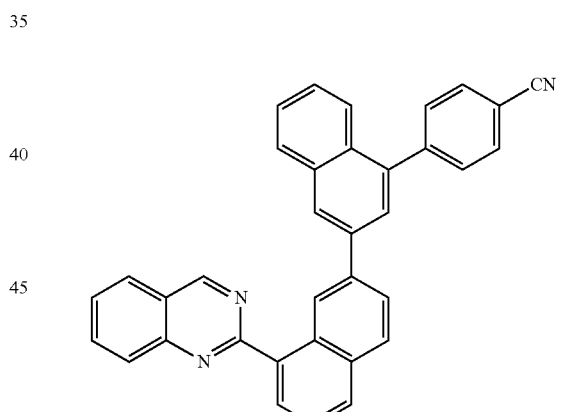
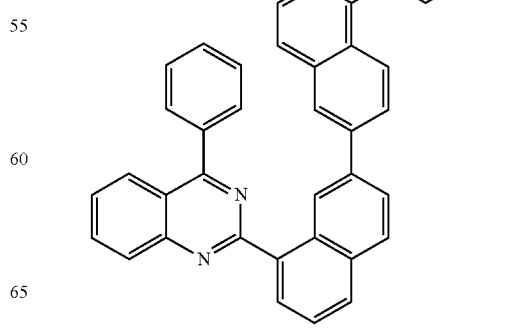

131
-continued
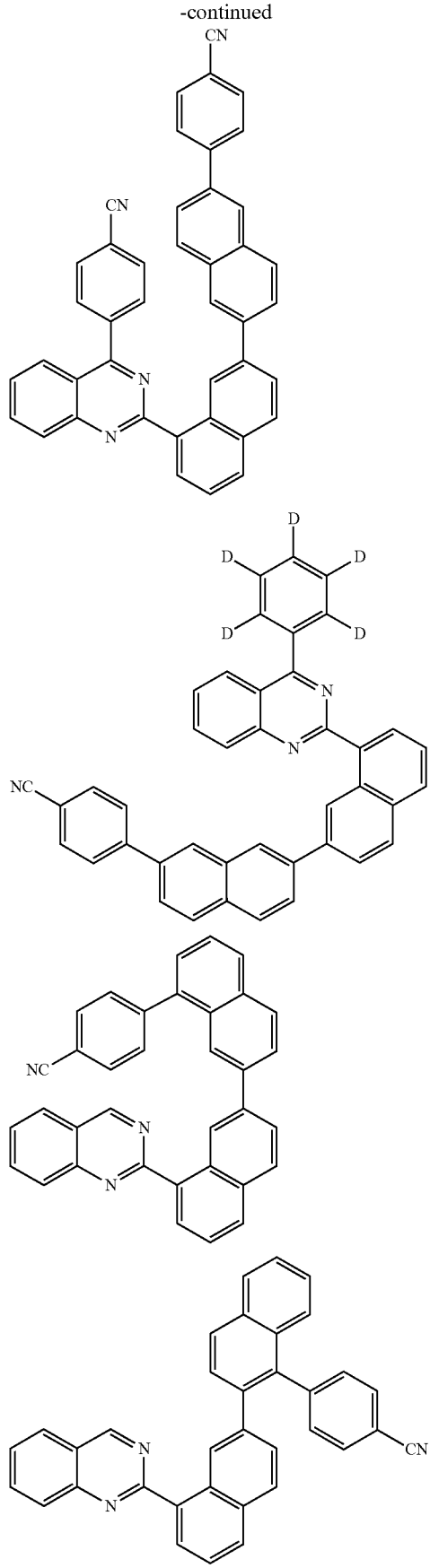
132
-continued
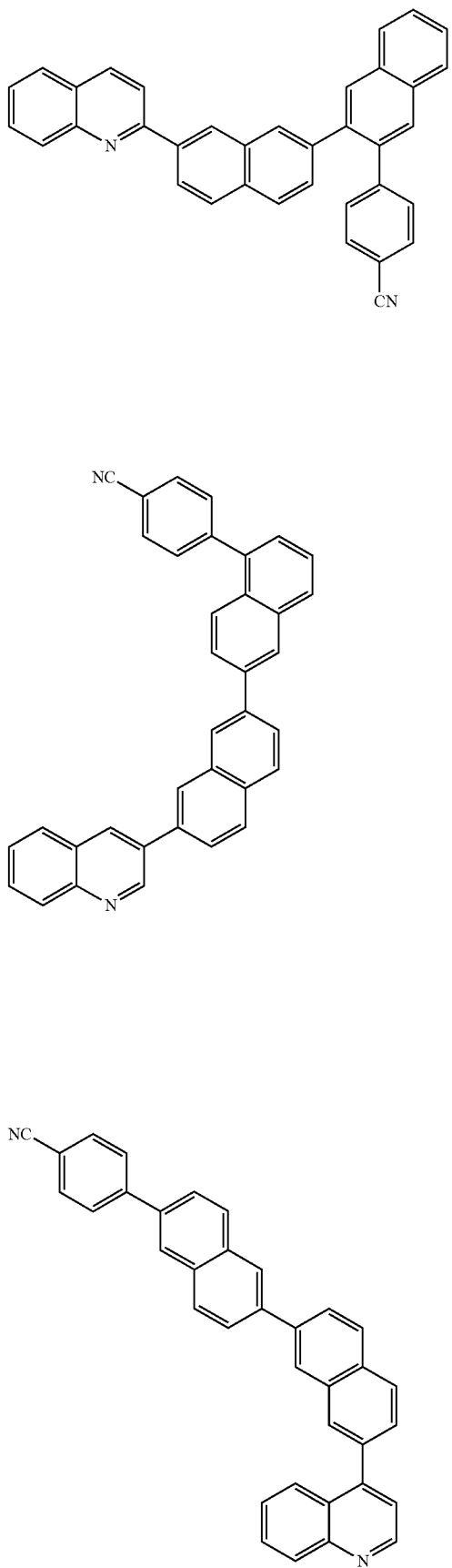

133
-continued
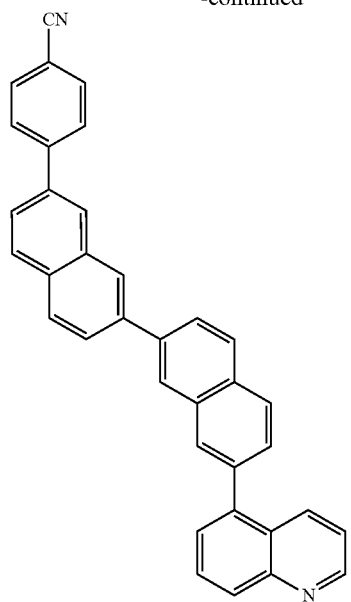
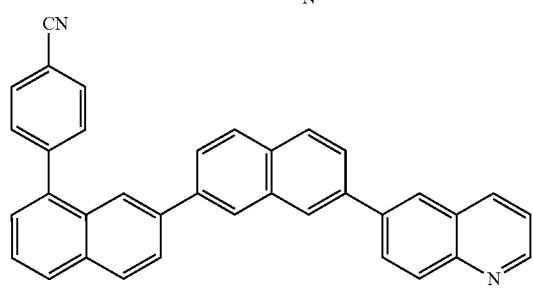
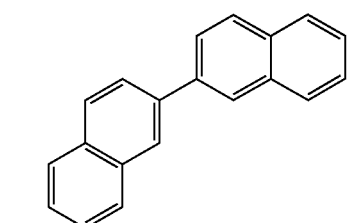
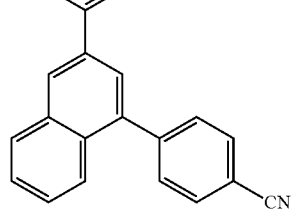
134
-continued
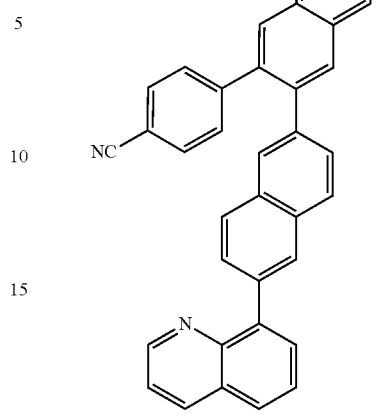
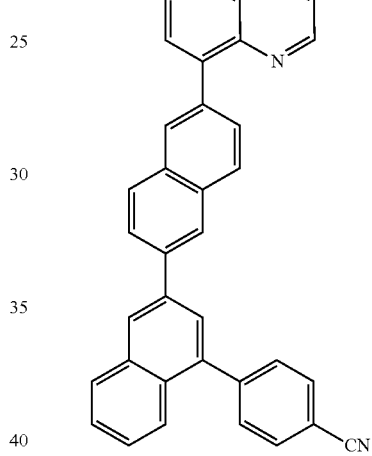
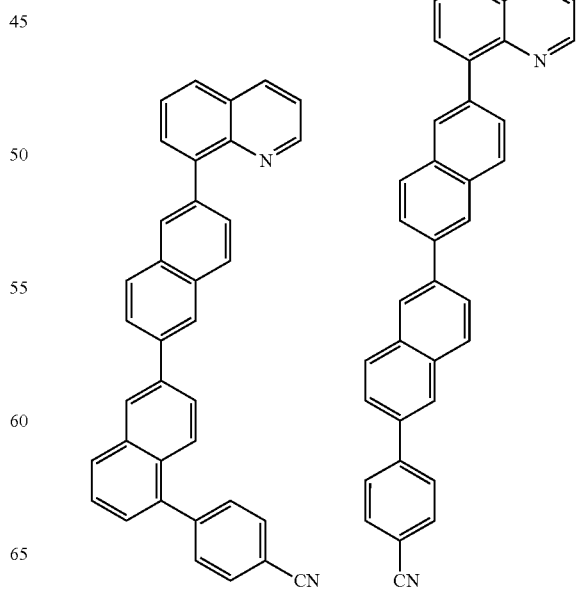

135
-continued
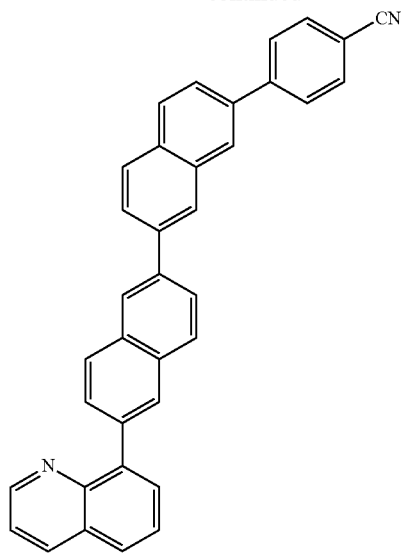
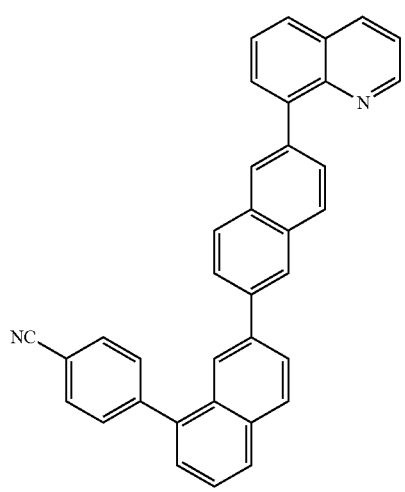
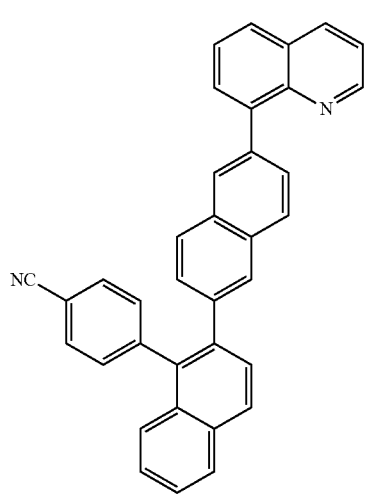
136
-continued
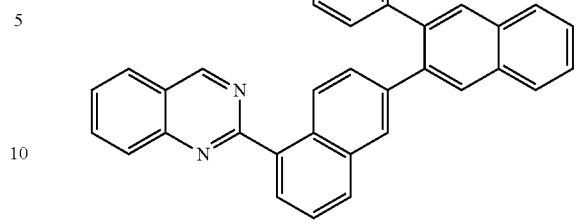
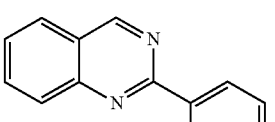
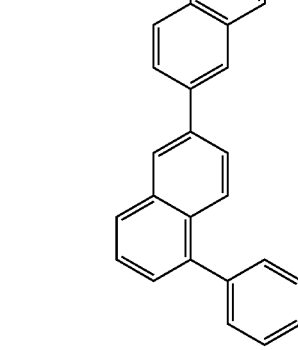

137
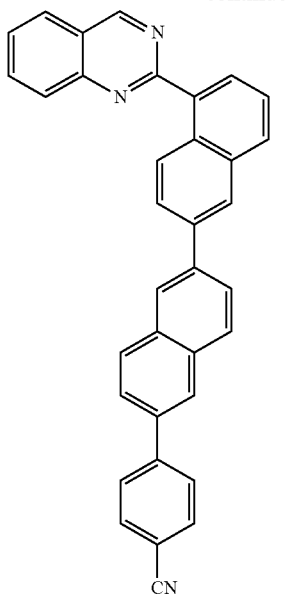
138
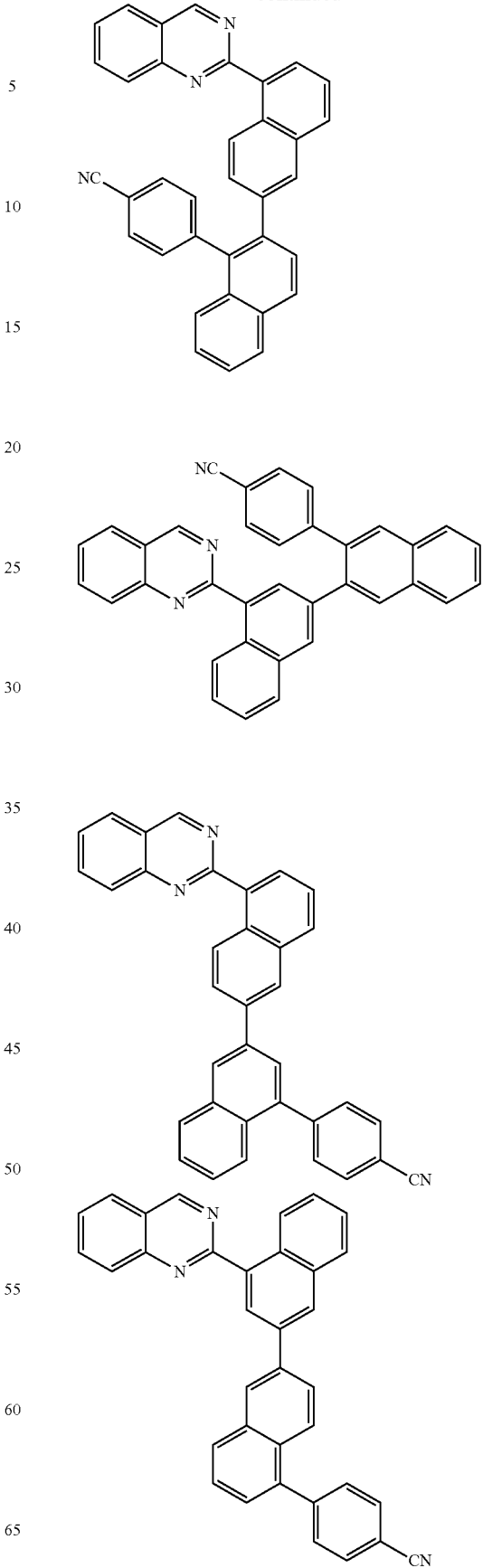

139
-continued
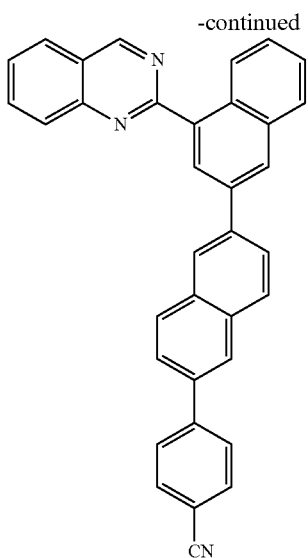
140
-continued
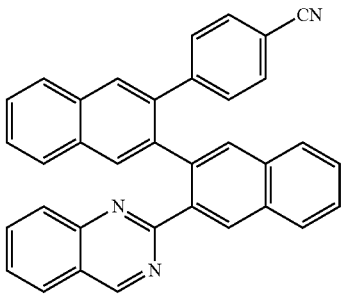
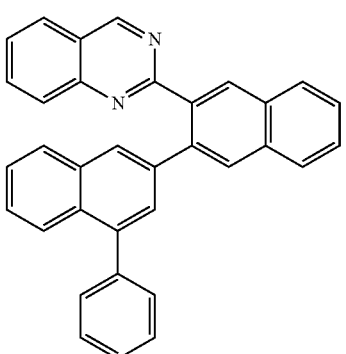
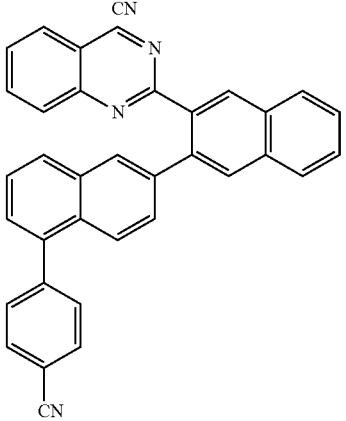
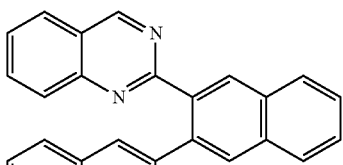
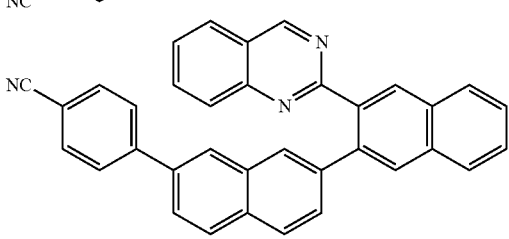

-continued
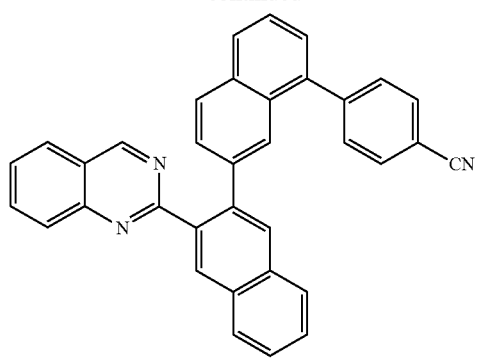
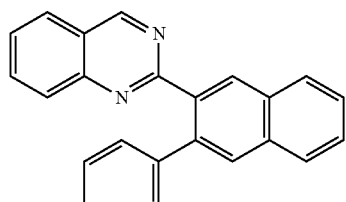
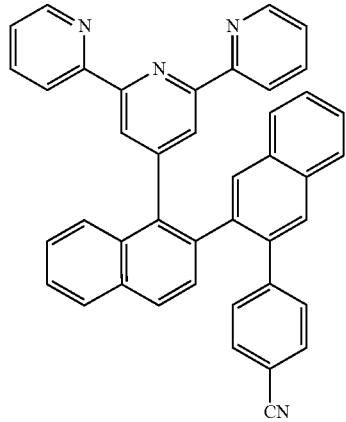
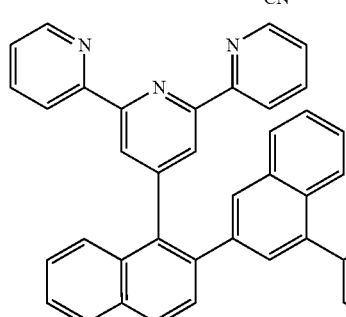
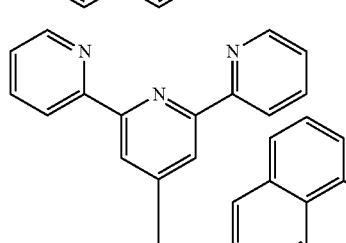
-continued
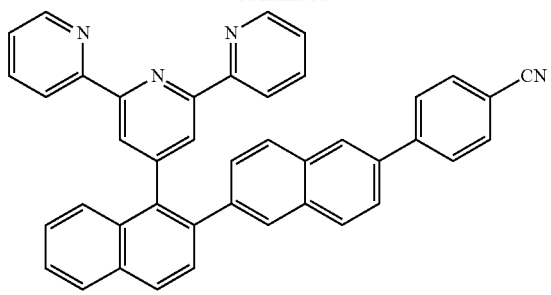
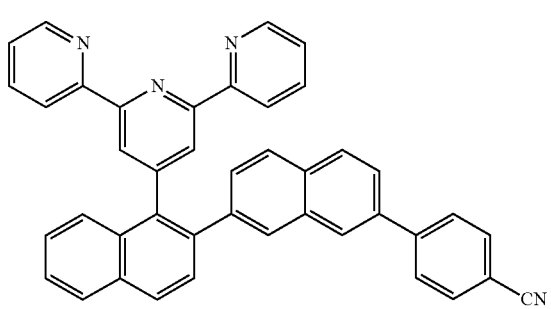
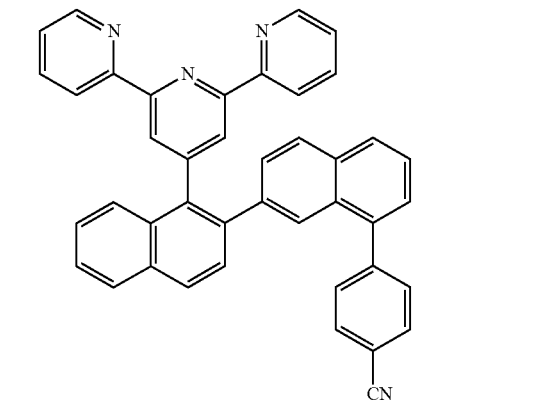
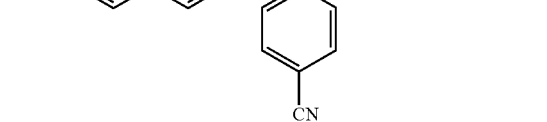

143
-continued
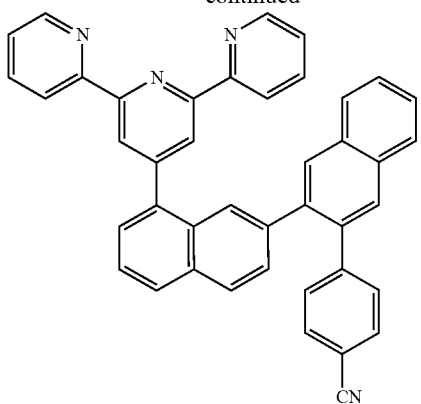
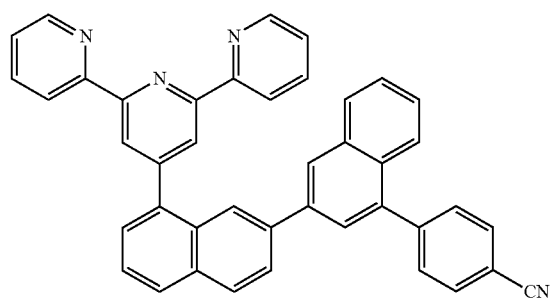
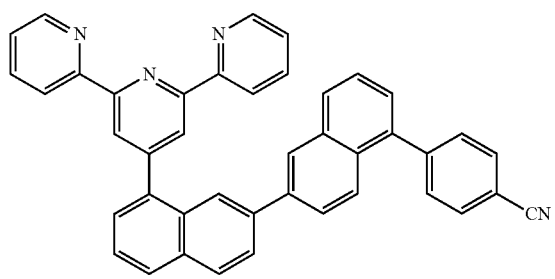
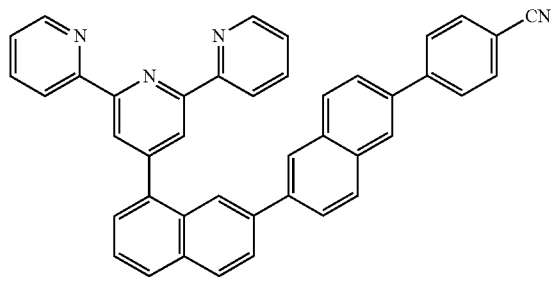
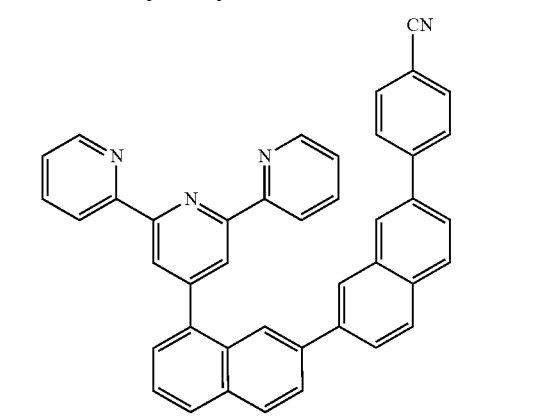
144
-continued
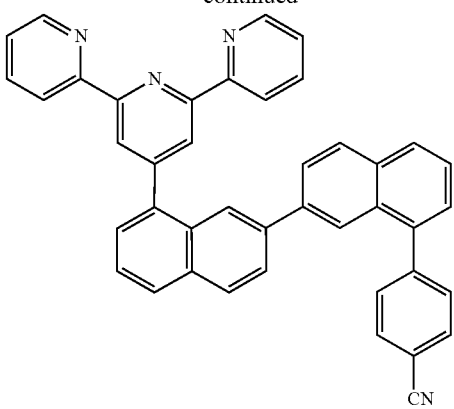
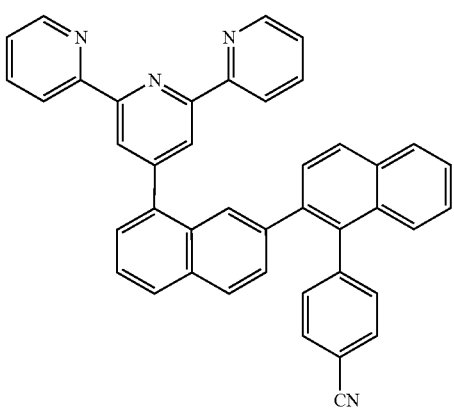
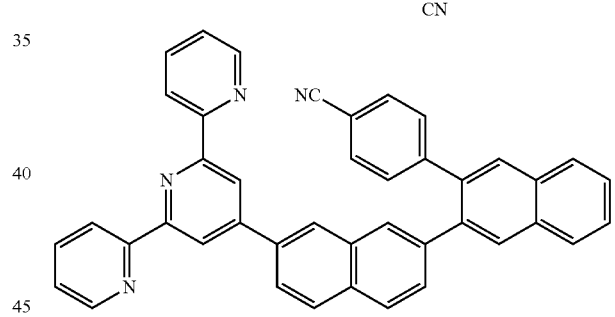
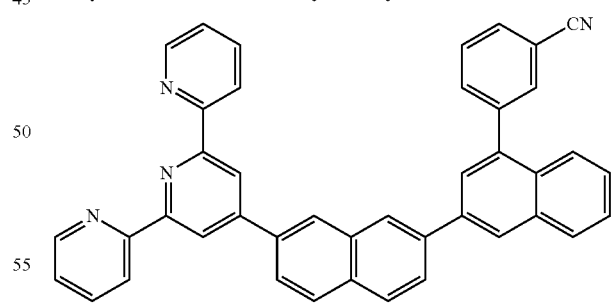
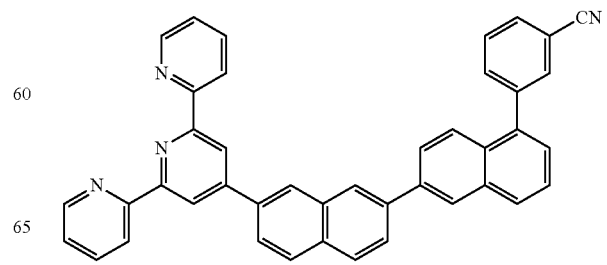

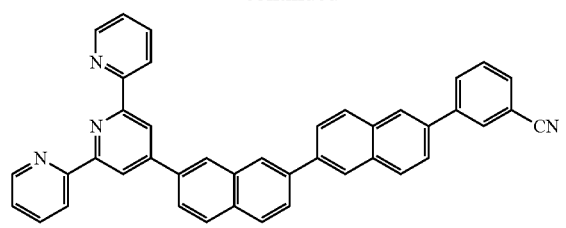
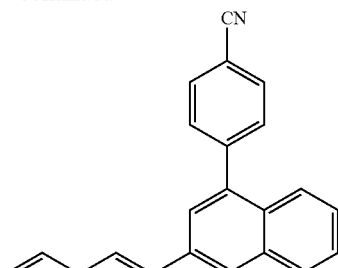
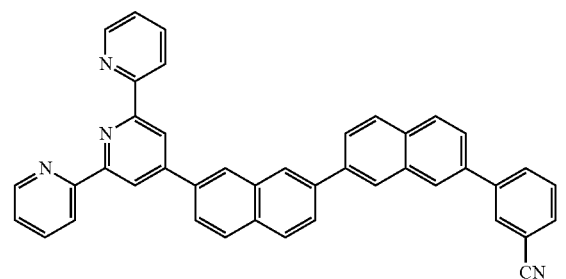
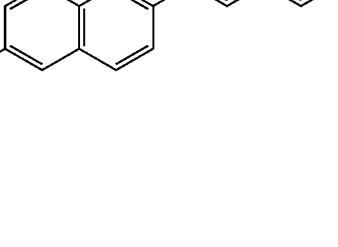
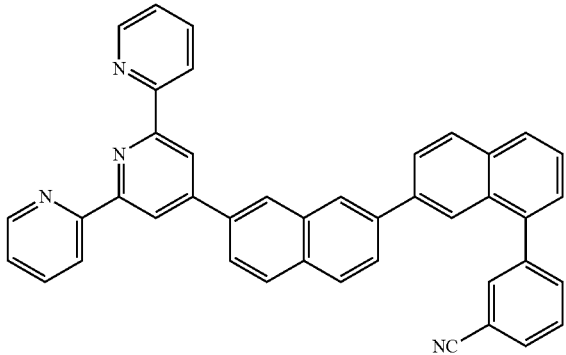
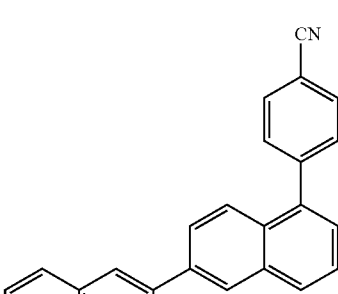
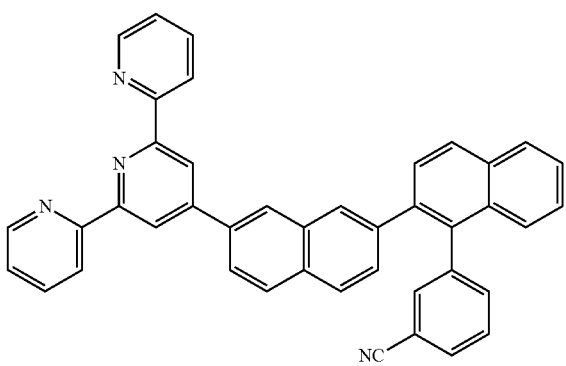
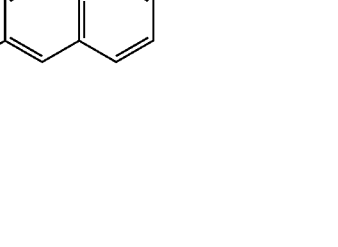
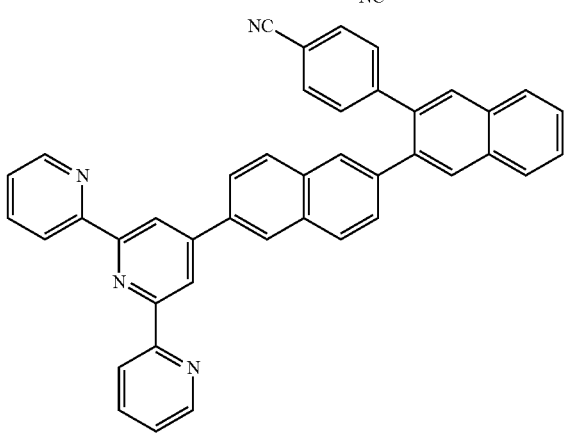
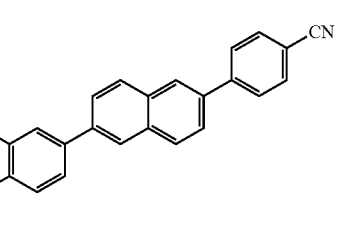
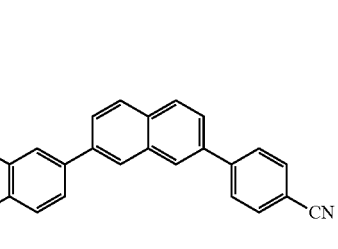

147
-continued
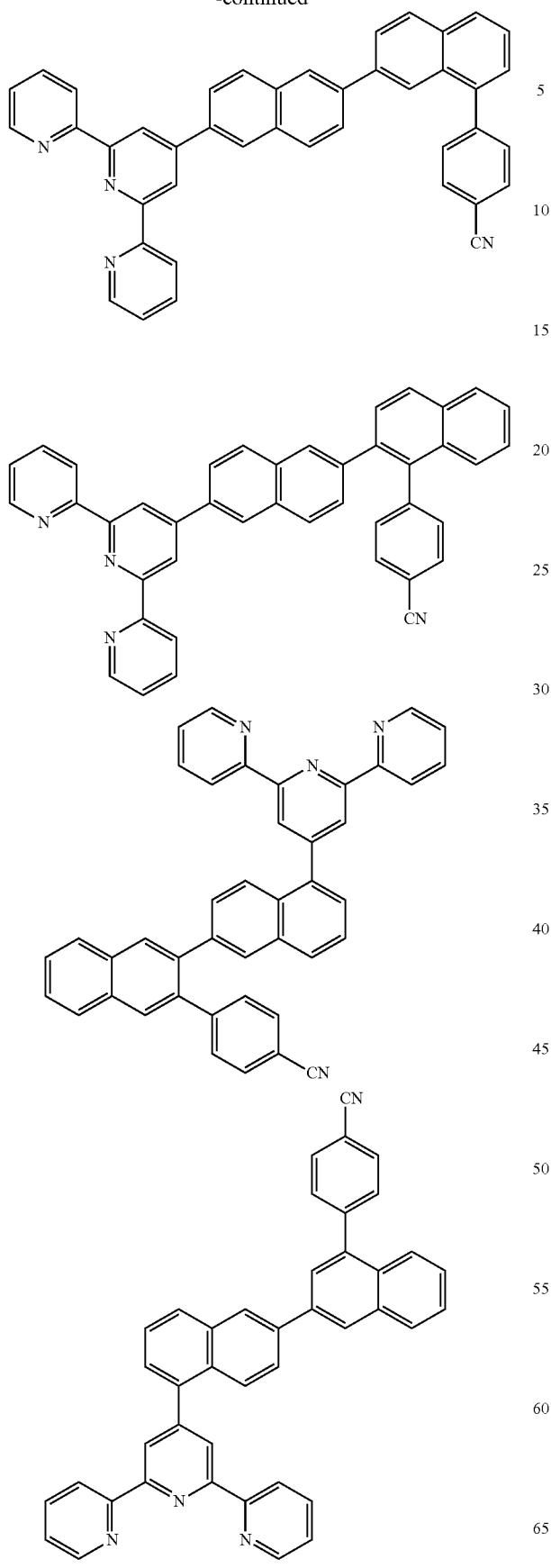
148
-continued
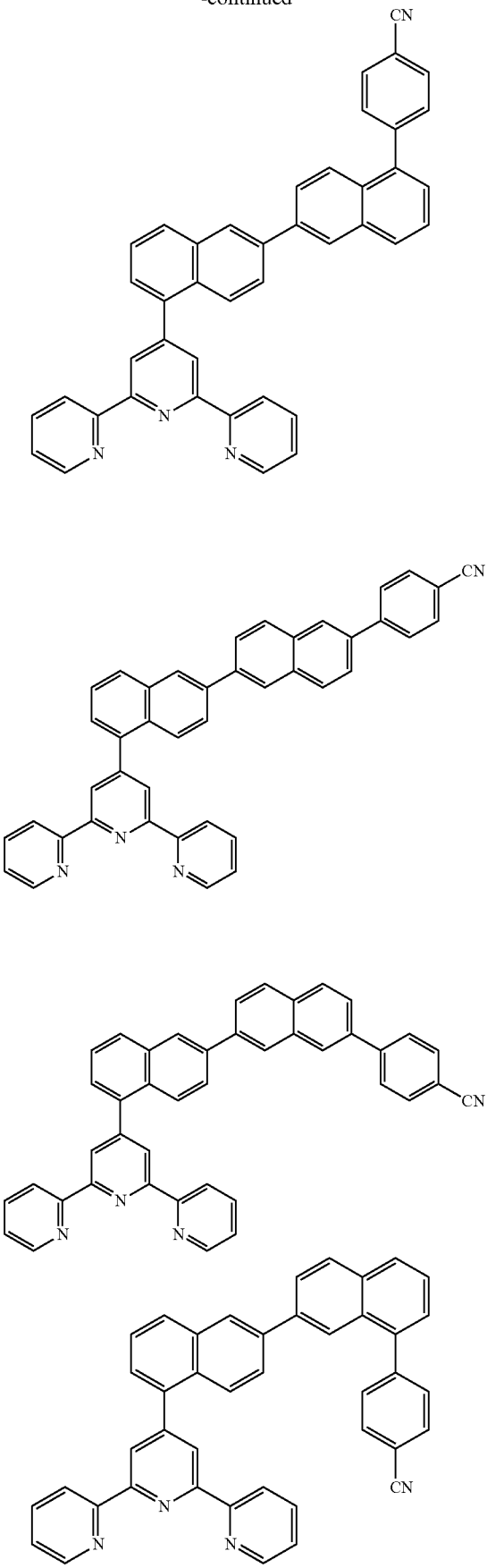

149
-continued
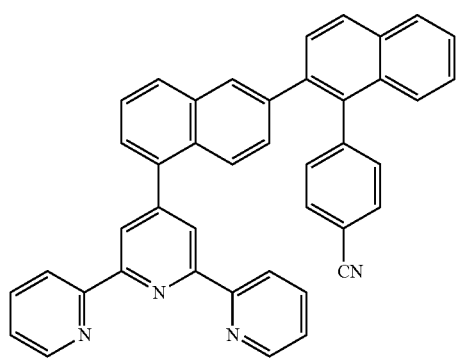
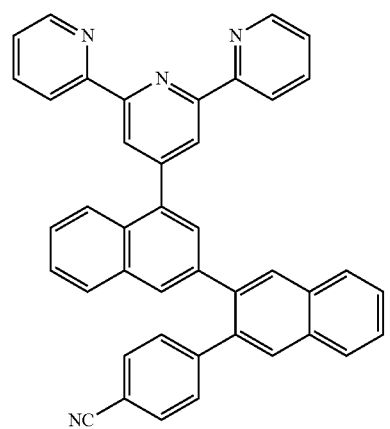
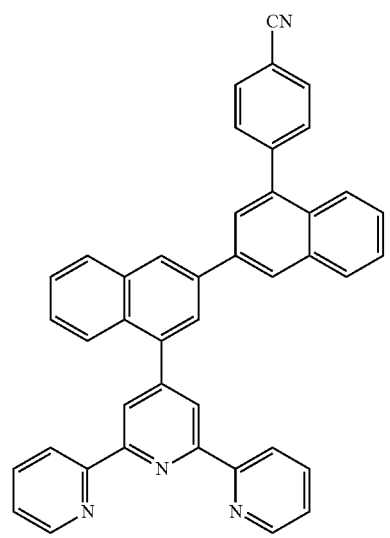
150
-continued
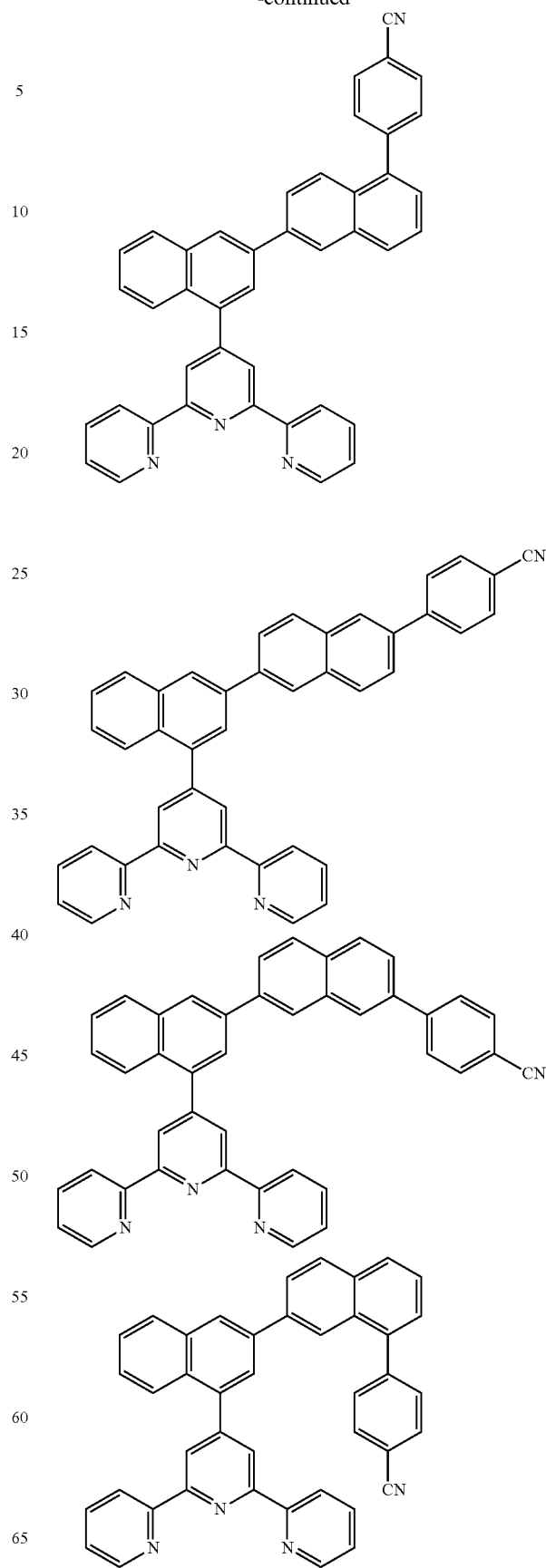

151
152
-continued
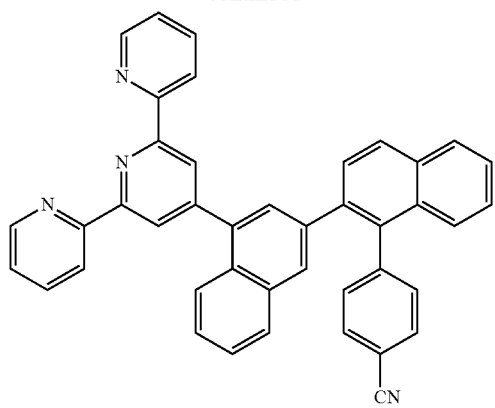
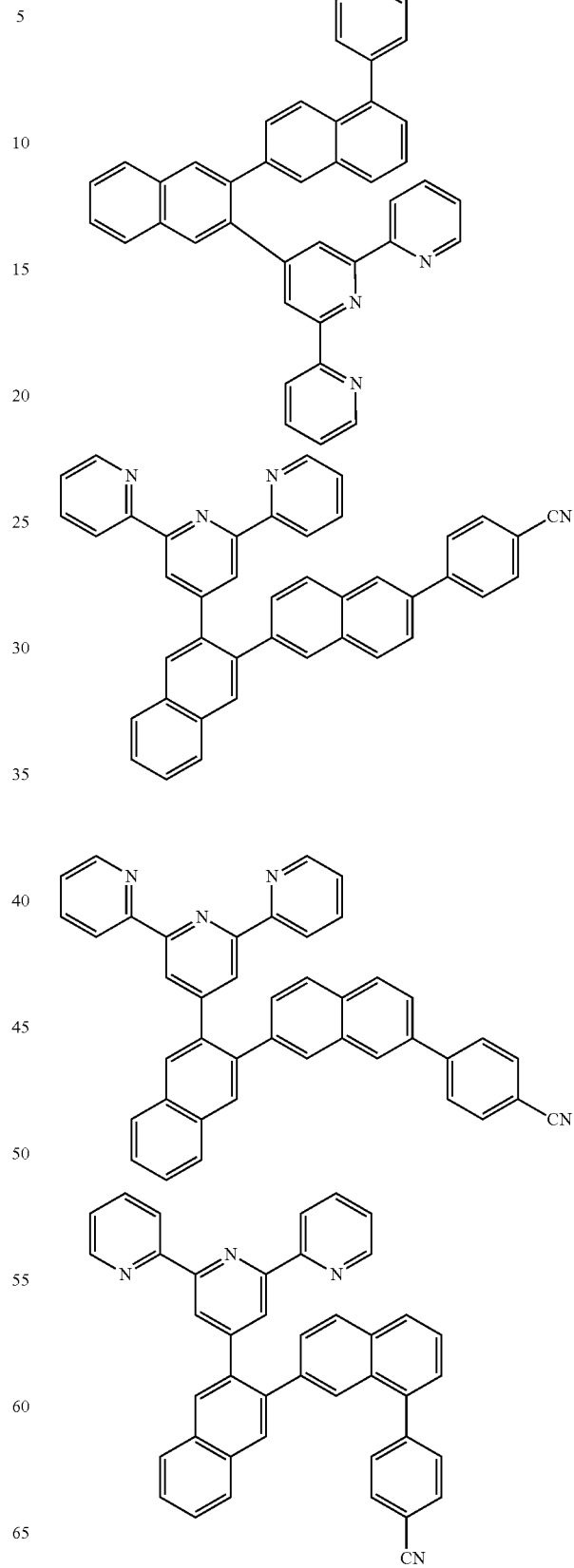

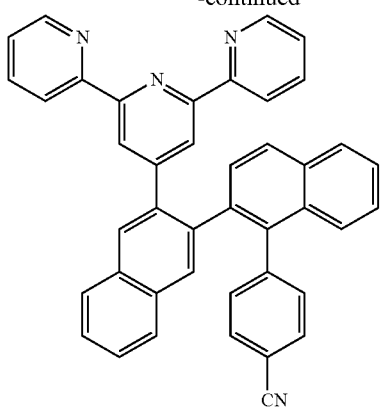
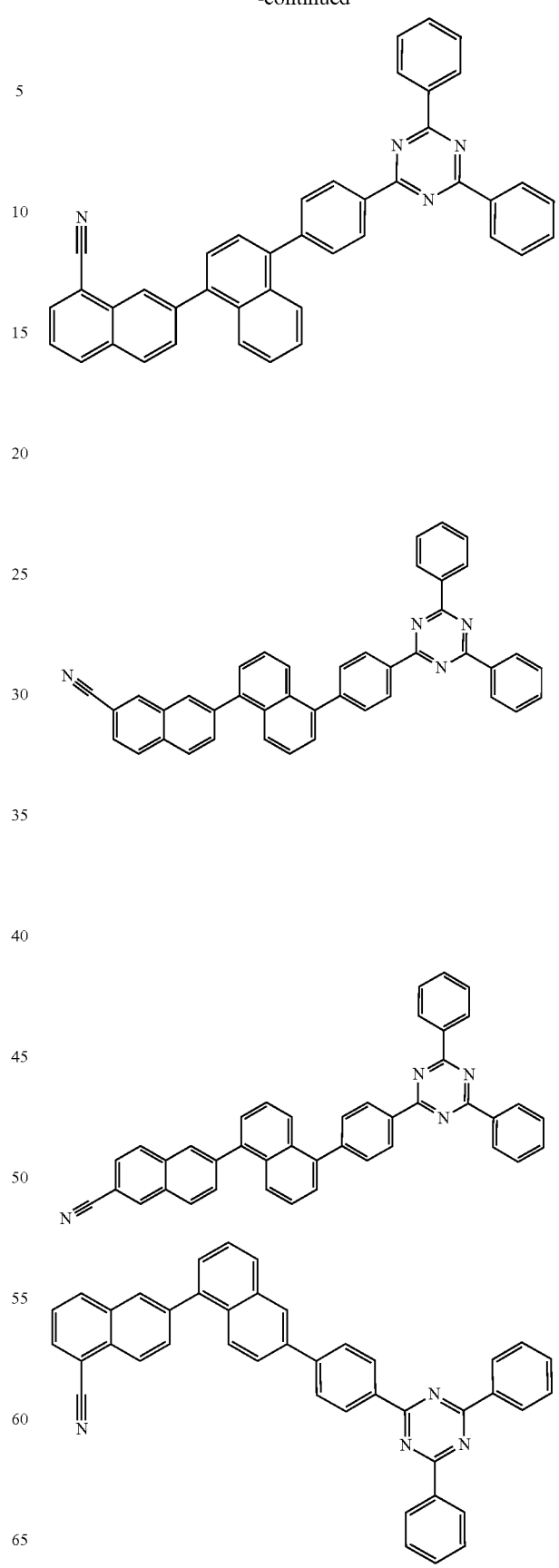

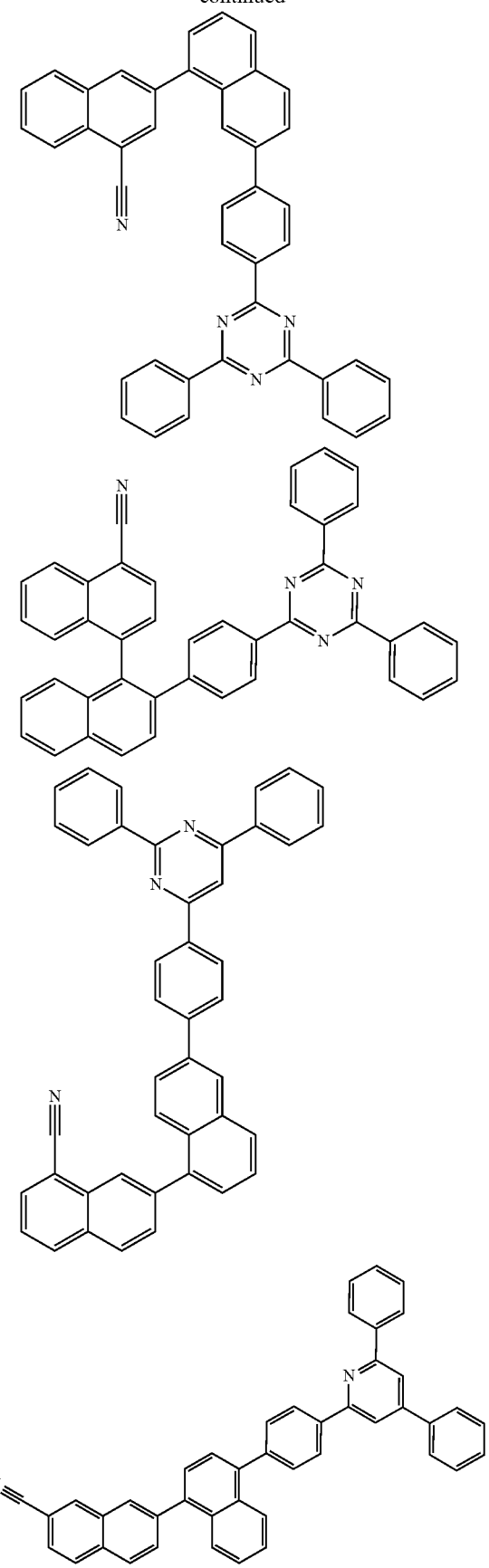
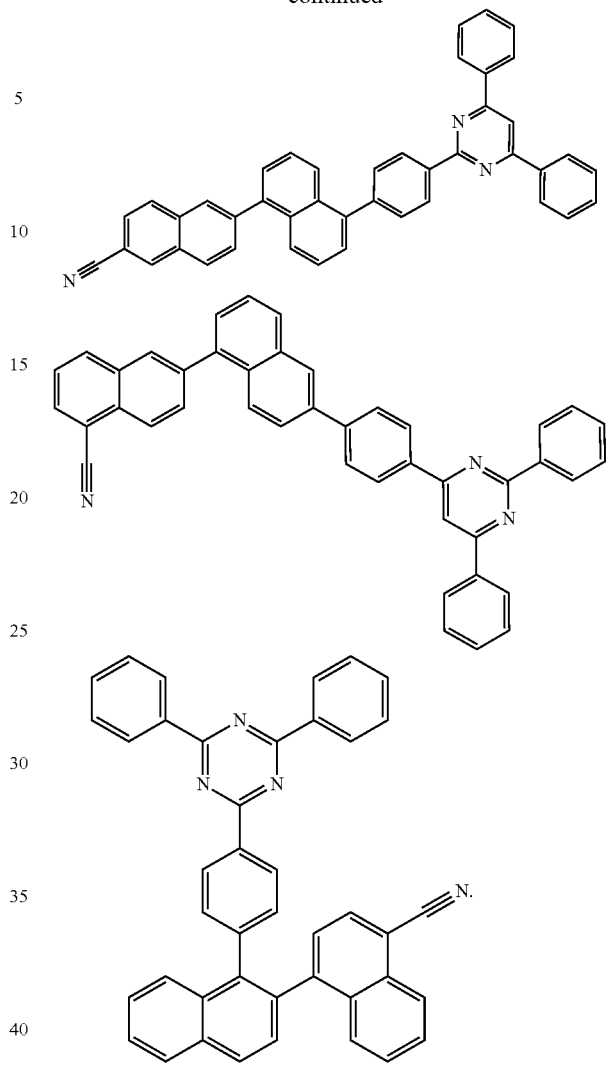

7. An organic light emitting device comprising: a first electrode; a second electrode provided opposite to the first electrode; and one or more organic material layers provided between the first electrode and the second electrode, wherein one or more one layers of the organic material layers comprise the compound according to claim 1.

8. An organic light emitting device comprising: a first electrode; a second electrode provided opposite to the first electrode; and one or more organic material layers provided between the first electrode and the second electrode, wherein one or more one layers of the organic material layers comprise the compound according to claim 2.

9. An organic light emitting device comprising: a first electrode; a second electrode provided opposite to the first electrode; and one or more organic material layers provided between the first electrode and the second electrode, wherein one or more one layers of the organic material layers comprise the compound according to claim 3.

10. An organic light emitting device comprising: a first electrode; a second electrode provided opposite to the first electrode; and one or more organic material layers provided between the first electrode and the second electrode, wherein one or more one layers of the organic material layers comprise the compound according to claim 4.

11. An organic light emitting device comprising: a first electrode; a second electrode provided opposite to the first electrode; and one or more organic material layers provided between the first electrode and the second electrode, wherein one or more one layers of the organic material layers comprise the compound according to claim 5.

12. An organic light emitting device comprising: a first electrode; a second electrode provided opposite to the first electrode; and one or more organic material layers provided between the first electrode and the second electrode, wherein one or more one layers of the organic material layers comprise the compound according to claim 6.

* * * * *

UNITED STATES PATENT AND TRADEMARK OFFICE
CERTIFICATE OF CORRECTION

PATENT NO. : 11,453,650 B2
APPLICATION NO. : 16/609199
DATED : September 27, 2022
INVENTOR(S) : Junghoon Yang et al.

It is certified that error appears in the above-identified patent and that said Letters Patent is hereby corrected as shown below:

In the Claims

In Claim 2, at Column 101, Lines 43-45, please replace the phrase:
"$L_2$ is a single bond, a substituted or unsubstituted $C_{6-60}$ arylene, or a substituted or unsubstituted $C_{5-60}$ heteroarylene"
With:
—$L_2$ is a single bond or a substituted or unsubstituted $C_{6-60}$ arylene—.

In Claim 6, at Column 112, Lines 50-65, please replace the Chemical Structure with:

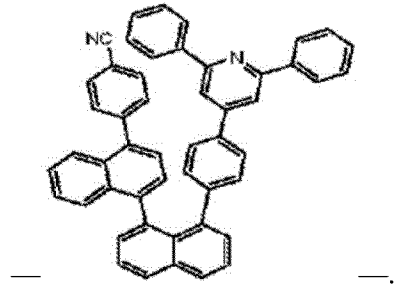

In Claim 6, at Column 113, Lines 1-19, please replace the Chemical Structure with:

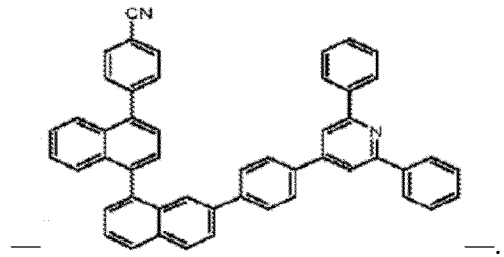

Signed and Sealed this
Eighth Day of November, 2022

Katherine Kelly Vidal
*Director of the United States Patent and Trademark Office*

CERTIFICATE OF CORRECTION (continued)
U.S. Pat. No. 11,453,650 B2

Page 2 of 2

In Claim 6, at Column 154, Lines 1-20, please delete the following Chemical Structure:

"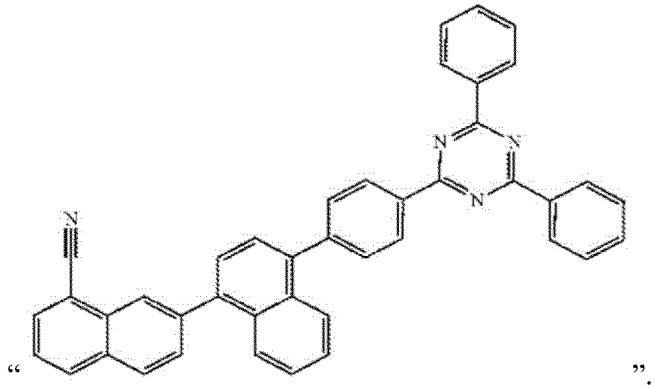".